US012808876B2

(12) United States Patent

Chou et al.

(10) Patent No.: US 12,808,876 B2

(45) Date of Patent: Nov. 24, 2026

(54) RAPID INTRA-CELLULAR ASSAY

(71) Applicant: Essenlix Corporation, Monmouth Junction, NJ (US)

(72) Inventors: Stephen Y. Chou, Princeton, NJ (US); Susan Y. Sun, Basking Ridge, NJ (US); Shengjian Cai, Monmouth Junction, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 537 days.

(21) Appl. No.: 17/787,804

(22) PCT Filed: Dec. 21, 2020

(86) PCT No.: PCT/US2020/066499

§ 371 (c)(1),
(2) Date: Jun. 21, 2022

(87) PCT Pub. No.: WO2021/127664

PCT Pub. Date: Jun. 24, 2021

(65) Prior Publication Data

US 2023/0400469 A1 Dec. 14, 2023

Related U.S. Application Data

(60) Provisional application No. 62/951,949, filed on Dec. 20, 2019.

(51) Int. Cl.

| | |
|---|---|
| ***C12Q 1/68*** | (2018.01) |
| ***G01N 1/30*** | (2006.01) |
| ***G01N 21/64*** | (2006.01) |
| ***G01N 33/58*** | (2006.01) |

(52) U.S. Cl.

CPC ............. *G01N 33/582* (2013.01); *G01N 1/30* (2013.01); *G01N 21/6428* (2013.01); *G01N 2001/302* (2013.01); *G01N 2021/6439* (2013.01); *G01N 2800/26* (2013.01)

(58) Field of Classification Search

USPC .......... 435/6.1, 6.11, 7.1, 91.1, 183; 436/94, 436/501; 536/23.1, 24.3; 530/300, 350

See application file for complete search history.

(56) References Cited

U.S. PATENT DOCUMENTS

| | | | | |
|---|---|---|---|---|
| 11,523,752 | B2 * | 12/2022 | Chou | A61B 5/0022 |
| 11,940,443 | B2 * | 3/2024 | Chou | G01N 33/54313 |
| 2003/0170613 | A1 | 9/2003 | Straus | |

(Continued)

FOREIGN PATENT DOCUMENTS

| | | | | |
|---|---|---|---|---|
| WO | WO-2017048871 A1 * | 3/2017 | | B01L 3/5055 |
| WO | 2018148729 A1 | 8/2018 | | |
| WO | 2019084512 A1 | 5/2019 | | |

OTHER PUBLICATIONS

Pei, How Do Biomolecules Cross the Cell Membrane? Acc. Chem. Res., 55, 309-318, 2022.*

(Continued)

*Primary Examiner* — Frank W Lu

(57) ABSTRACT

The present invention is to provide methods and devices that monitoring health and diagnosing a disease by directly measuring the biomarkers inside a cell (intra-cellular detection) rapidly and easily.

12 Claims, 13 Drawing Sheets

Specification includes a Sequence Listing.

(56) References Cited

U.S. PATENT DOCUMENTS

| | | | |
|---|---|---|---|
| 2010/0034699 A1 | 2/2010 | Chan | |
| 2013/0065788 A1 | 3/2013 | Glezer et al. | |
| 2015/0253321 A1 | 9/2015 | Chou et al. | |
| 2019/0170734 A1 | 6/2019 | Chou et al. | |

OTHER PUBLICATIONS

Jamur et al., Permeabilization of Cell Membranes. Immunocytochemical Methods and Protocols, Methods in Molecular Biology, 588, 63-66, 2010.*

International Search Report and Written Opinion of the International Searching Authority established by the ISA/KR completed on May 10, 2021, for PCT/US2020/066499.

* cited by examiner

| Probe | Scramble ctrl | Mir-16-5p | Let-7a-5p |
|---|---|---|---|
| Average | 9 | 20 | 113 |
| SD | 3 | 6 | 31 |

| Fluorescent intensity | Gr/Mo | Lym |
|---|---|---|
| Let-7a-5p | 85.8±16.4 | 26.5±8.6 |
| Mir-150-5p | 22.7±12.9 | 44.1±13.2 |

* Number in the chart indicates LPS concentration (ug/ml)

| LPS con. ug/ml | No. counted cells | % IL-6 (+) cells | IL6 fluorescent intensity | Total Fluorescence | ELISA IL-6 con. (pg/ml) |
|---|---|---|---|---|---|
| 0 | 52 | 58 | 36 | 2098 | 0 |
| 0.01 | 78 | 71 | 36.7 | 2611 | 405 |
| 0.1 | 81 | 83 | 34 | 2743 | 621 |
| 1 | 37 | 82 | 37 | 3048 | 1113 |
| 5 | 44 | 89 | 60 | 5308 | 1634 |
| 25 | 79 | 96 | 68 | 6515 | 5340 |
| 100 | 49 | 98 | 107 | 10516 | 10444 |

*Total Fluorescence equals to % IL-6(+) cells multiply IL-6 fluorescence intensity

RAPID INTRA-CELLULAR ASSAY

CROSS REFERENCE TO RELATED APPLICATIONS

This application is a National Stage entry (§ 371) application of International Application No. PCT/US2020/066499, filed on Dec. 21, 2020, which claims the benefit of priority of U.S. Provisional Patent Application No. 62/951,949, filed on Dec. 20, 2019, the contents of which are relied upon and incorporated herein by reference in their entirety. The entire disclosure of any publication or patent document mentioned herein is entirely incorporated by reference.

INCORPORATION-BY-REFERENCE OF SEQUENCE LISTING

This application contains a Sequence Listing submitted as an ASCII text file. The ASCII text file is named ESX-132-2-Sequencing-Listing.txt, created on May 15, 2023, and 4.38 KB in size. The information in the Sequence Listing is incorporated by reference in its entirety.

FIELD

The present application relates to, among other things, a method and/or a device for rapid intra-cellular assays and their applications in detection a biomarker in a sample and/or in diagnostic testing a health disorder.

BACKGROUND

There are great needs to have rapid, sensitive, to monitoring health and diagnosing a disease. Many methods used today involve a detection of cell-free biomarkers in a sample.

SUMMARY OF INVENTION

The present invention is to provide methods and devices that monitoring health and diagnosing a disease by directly measuring the biomarkers inside a cell (intra-cellular detection) rapidly and easily. Another aspect of the presentation is to provide the devices and methods that measure that quantify the cell-free biomarkers in a blood using the biomarkers inside the cell.

The present invention provides the device and method that detect a biomarker inside a cell in a sample rapidly and easily (e.g. in 60 seconds or less, in one simple step) and applications in monitoring and diagnostic a health condition. The detection probe comprises protein detection agent or nucleic acid detection probe.

Another objective is to rapid intra-cellular assays for detection of a biomarker in a sample and/or in diagnostic testing a health disorder.

According to the present invention, the instant intra-cellular single-cell assay (INSA) provide a one-step chemical contact with the sample containing at least one cell including 60 sec or less incubation, imaging, analyzing, and reporting the presence and quantity of detected intracellular biomarkers, such as nucleic acids and proteins, directly from a fresh crude biological sample, such as a needle biopsy sample, whole blood, urine, sputum, saliva, swab samples (pap smear), and like samples. The INSA procedure provides advantages in diagnosis of, for example, diseases that have established or discoverable intracellular diagnostic biomarkers, for example: infectious diseases; malignant diseases; autoimmune diseases; metabolic diseases, and inherited genetic disorders. The tabulated listing below provides examples of sample sources (e.g., bodily fluid) or sample retrieval methods, disease categories, and diseases and conditions, where the disclosed INSA methodology can be used for diagnosis in accordance with the disclosed methods.

One aspect of the present disclosure is to provide devices and methods for easy and rapid staining of a biomarker inside a cell by utilizing a pair of plates that are movable to each other to manipulate a tissue sample and/or a small volume of staining liquid, reducing sample/staining liquid thickness, making a contact between the sample and staining reagent, etc.—all of them have beneficial effects on the cell staining (simplify and speed up stain, wash free, and save reagent)

Another aspect of the present disclosure is to provide for easy and rapid intra-cellular staining by coating staining reagents on one or both of the plate(s), which upon contacting the liquid sample and/or the staining liquid, are dissolved and diffuse in the sample and/or the staining liquid, easing the handling of staining reagents with no need of professional training.

Another aspect of the present disclosure is to ensure uniform access of the sample to the staining reagent by utilizing the plates and a plurality of spacers of a uniform height to force the sample and/or staining liquid to forma thin film of uniform thickness, leading to same diffusion distance for the staining reagents across a large lateral area over the sample.

Another aspect of the present disclosure is to provide systems for easy and rapid intra-cellular staining and imaging by combining the pair of plates for staining with a mobile communication device adapted for acquiring and analyzing images of the cells stained by the plates. Optionally, the mobile communication is configured to send the imaging data and/or analysis results to a remote location for storage and/or further analysis and interpretation by professional staff or software.

BRIEF DESCRIPTION OF THE DRAWINGS

The drawings if any, described below, are for illustration purposes only. In some Figures, the drawings are in scale and not to scale in other Figures. For clarity purposes, some elements are enlarged when illustrated in the Figures. The drawings are not intended to limit the scope of the disclosure.

DETAILED DESCRIPTION OF EXEMPLARY EMBODIMENTS

Figure 1A:
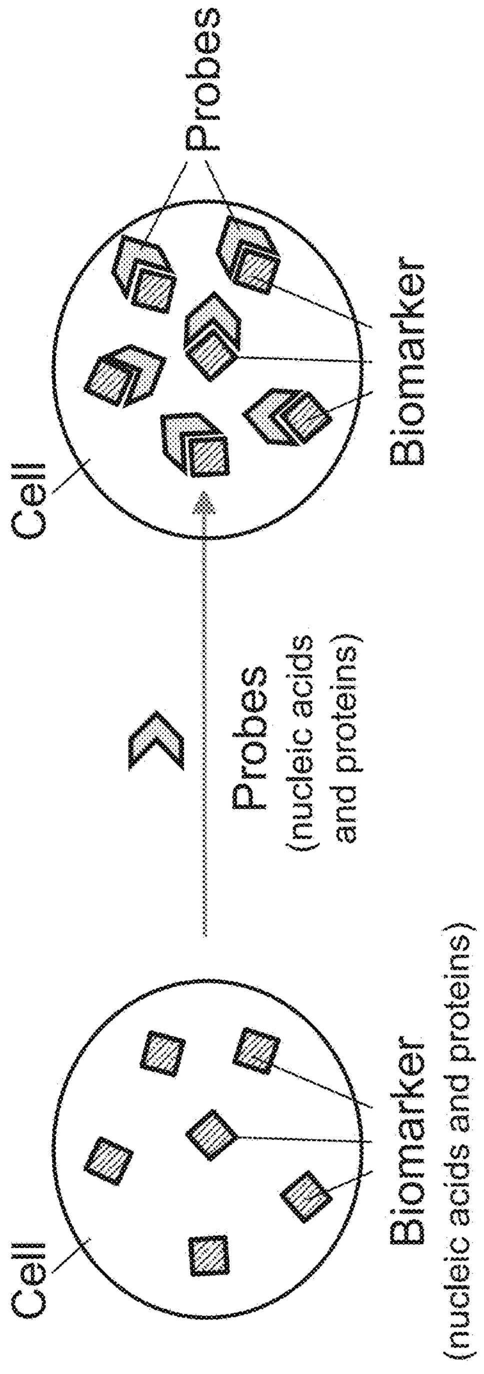
FIGS. 1A and 1B shows schematics of exemplary intra-cellular detection embodiments. Schematic A illustrates the method: the intracellular biomarkers, such as nucleic acids and proteins, are inside the target cell. After making a specific probe get inside the cell, a detectable complex between the specific probe and the intra-cellular biomarker is formed and can be detected or imaged. Schematic B illustrates the above method is happened inside a sample holder comprising two plates, where the cell, biomarker and the probe are sandwiched between the two plates to form a thin layer.

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

Definitions

The term "Stain", "stain formulation", and like terms generally refer to a material or mixture that contains a component that can interact with or react with an intracellular target such as a molecule or a virus to form an intracellular reaction product, and that can enable or enhance for example, the detection, the development, the imaging, the quantification, and like descriptors, that relate to establishing the presence of the target and quantifying the amount of the target present inside a cell.

The term "Q-Card" and "QMAX Card" are interchangeable.

"Probe" and like terms refer to a component that can interact with or react with an intracellular target such as a molecule or a virus (see "stain" definition above).

"Intra-cellular", "intracellular", and like terms refer to "within a cell" or "inside a cell".

"Extra-cellular", "extracellular", and like terms refer to "outside a cell" or "not inside a cell".

"Disease", "condition", and like terms refers to, for example, any harmful deviation from the normal structural or functional state of a cell or an organism having one or more cells, generally associated with certain signs and symptoms and differing in nature from physical injury. A diseased cell or organism commonly exhibits signs or symptoms indicative of its abnormal state. Disease and condition can be used interchangeably.

The term "intracellular biomarker" refers the biomarkers that are inside a cell.

The term "cell-free biomarker" refers to the biomarkers in a sample but outside the cells in the sample.

The terms "cell-free biomarker" and "free biomarker" are interchangeable.

"Plasma" refers to the blood fluid that contains blood clotting agents. Plasma is a clear yellowish fluid part of the blood. Plasma contains clotting factors and water.

The terms "Serum" refers to the liquid part of the blood after the coagulation. Serum is the water fluid from blood without the clotting factors (i.e., serum=plasma−clotting factors). Serum contains proteins like albumin and globulins.

The terms "X-plate" is a top plate for a Qmax card having two opposable plates.

The terms "M-plate" is a bottom plate or substrate, typically having pillars or spacers, for a Qmax card having two opposable plates.

The term "INSA" is an acronym for instant intra-cellular single-cell assay.

The term "INSH" is an acronym for instant intra-cellular single-cell hybridization.

The term "ISIM" is an acronym for instant intra-cellular single-cell immunoassay.

The term "INSA" is an acronym for instant intra-cellular single-cell assay.

The terms "ELISA" is an acronym for enzyme linked immuno-sorbant assay.

The terms "FISH" is an acronym for fluorescent in situ hybridization.

The terms "CMV" is an acronym for cytomegalovirus.

The terms "LPS" is an acronym for lipopolysaccharides.

The terms "IFN" is an acronym for interferon.

The terms "PPD" is an acronym for purified protein derivative.

The terms "HIV" is an acronym for human immunodeficiency virus.

The terms "HPV" is an acronym for human papillomavirus.

The terms "HBV" is an acronym for Hepatitis B virus.

The terms "IL4", "IL-4", and like abbreviations, are acronyms for interleukin 4. IL-4 is a cytokine that induces differentiation of naive helper T cells (Th0 cells) to Th2 cells. When activated by IL-4, Th2 cells subsequently produce additional IL-4 in a positive feedback loop.

The term "intra-cellular staining" refers to stain a biomarkers inside of cell using a detection probe, and the detection probe is initially outside of the cell and then introduced into the cell. In certain embodiments, the detection probe is specific to the biomarkers inside the cell.

The term "staining solution" and "staining liquid" are interchangeable.

The term "inner surface" of the first and second plates are the surfaces that are facing each other in a closed configuration.

1. Instant Intra-Cellular Single-Cell Assay (INSA)

According to the present invention, the instant intracellular single-cell assay (INSA) provide a one-step chemical contact with the sample containing at least one cell including 60 sec or less incubation, imaging, analyzing, and reporting the presence and quantity of detected intracellular biomarkers, such as nucleic acids and proteins, directly from a fresh crude biological sample, such as a needle biopsy sample, whole blood, urine, sputum, saliva, swab samples (pap smear), and like samples. The INSA procedure provides advantages in diagnosis of, for example, diseases that have established or discoverable intracellular diagnostic biomarkers, for example: infectious diseases; malignant diseases; autoimmune diseases;

metabolic diseases, and inherited genetic disorders. The tabulated listing below provides examples of sample sources (e.g., bodily fluid) or sample retrieval methods, disease categories, and diseases and conditions, where the disclosed INSA methodology can be used for diagnosis in accordance with the disclosed methods.

A method of performing an intra-cellular single-cell assay, comprising:

(a) having a first plate and a second plate, each has a sample contact area on its surface, wherein the sample contact surfaces contact a sample comprising a cell that contains or is suspected to contain an analyte inside the cell, (b) having a detection probe that specifically binds the analyte;

(d) sandwiching the sample and the detection probe, and the optical enhancer between the two sample contact areas of the two plates to form a thin layer of a thickness of 200 microns (um) or less; and (e) imaging using an imager the thin layer to detect the cell that has the analyte bound to the detection probe;

wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the two plates are movable relative to each other and the spacers are between the plates to regulate the spacing between the plates.

A device of an intra-cellular single-cell assay, comprising:

(a) a first plate and a second plate, each has a sample contact area on its surface, wherein the sample contact surfaces contact a sample comprising a cell that contains or is suspected to contain an analyte that is inside the cell;

(b) a detection probe that specifically binds the analyte;

wherein the sample contact areas in the first and second plates faces each other and sandwich the sample and the detection probe, wherein the thin layer has a thickness of 200 microns (um) or less; and (c) an imager that images the thin layer to detect the detection probe that has specifically bound to the analyte;

wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (c) of imaging, in the thin layer, the location having the bound detection probe is distinguishable from the locations not having the bound detection probe, wherein the bound detection probe is the detection probe bound to the analyte in the cell.

In some embodiments, the detection probe is coated on at least one of the sample contact areas of the plate.

In some embodiments, the analyte comprises a protein or a nucleic acid (e.g. DNA/RNA) or a combination.

In some embodiments, the method and the devices further comprising a permeabilization reagent that assists the probe penetrate into the cell.

A method of collecting and analyzing a sample using intra-cellular cytology comprising:

obtaining a first plate and a second plate that are movable relative to each other;

depositing a part of the sample on an inner surface of a first plate;

having reagents for staining and penetration of the cell;

bringing the two plate together to a closed configuration, in which, the two inner surfaces of the first and second plates are facing each other and the spacing between the plates is regulated by spacers between the plate, and at least a part of the staining solution is between the sample and the inner surface of the second plate;

having an imager; and imaging the sample for analysis.

A subject comprises a human or animal.

In some embodiments, the reagents are a staining reagents and cell permeabilizing reagent. In some embodiments, the reagents are in solution and mixed with the sample. In some embodiments, the reagents are coated and dried on either (i) surface of the first plate and/or on top of the sample, (ii) inner surface of the second plate, or (iii) both, In some embodiments, the analysis by imaging is cytoanalysis.

In some embodiments, the spacers are fixed on one or both plates. In some embodiments, the spacers are inside of the staining solution.

In some embodiments, the sample is mixed with the staining solution before dropped on the plate.

In some embodiments, the staining solution comprises staining agent (things that stain cells/tissue) in a solution. In some embodiments, the staining solution does not comprises staining dye in a solution, but is configured to transport a staining agent coated on one of the plates into the cells/tissue. In some embodiments, the staining solution comprises staining agent (things that stain cells/tissue) in a solution, and is configured to transport a staining agent coated on one of the plates into the cells/tissue.

In some embodiments, the spacer height is configured to make the stained cells and/or tissues be visible by an imaging device without washing away the staining solution between the second plate and the sample.

In some embodiments, the spacer height is configured to make the stained cells and/or tissues be visible by an imaging device without open the plates after the plates reached a closed configuration.

In some embodiments, a sample was stained without washing away the staining solution between the second plate and the sample, and imaged by an imager, after closing the plates into a closed configuration, in 30 seconds or less, 60 seconds or less, 120 seconds or less, 300 seconds or less, 600 seconds or less, or a range between any of the two.

In some preferred embodiments, a sample was stained without washing away the staining solution between the second plate and the sample, and imaged by an imager, after closing the plates into a closed configuration, in 30 seconds or less, 60 seconds or less, 120 seconds or less, or a range between any of the two.

In some preferred embodiments, a sample was stained without washing away the staining solution between the second plate and the sample, and imaged by an imager, after closing the plates into a closed configuration, in 30 seconds or less, 60 seconds or less, or a range between any of the two.

In some embodiments, the spacer height is 0.2 um (micron) or less, 0.5 um or less, 1 um or less, 3 um or less, 5 um or less, 10 um or less, 20 um or less, 30 um or less, 40 um or less, um or less, or a range between any of the two.

In some preferred embodiments, the spacer height is 3 um or less. In some preferred embodiments, 10 um or less. In some preferred embodiments, 20 um or less. In some preferred embodiments, 30 um or less.

In some preferred embodiments, the staining solution has, after the plates are in a closed configuration, a thickness that is equal or less than sub-noise thickness.

The term "sub-noise thickness" (SNT) reference to the a thickness of a sample or a staining solution, which is thinner than a thickness where the noise in the sample or in the staining solution is below the signal from a specifically bound optical label, making the optical label visible to an imager. Making a staining solution less than the SNT will remove the need to wash away the unbind optical labels.

The terms "detection agent" and "detection probe" are interchangeable

2. Instant Intra-Cellular Single-Cell Assay (INSA) for Diagnosing Diseases

In some embodiments, the present invention provides:

A method for determining the presence and the quantity of one or more intracellular biomarkers indicative of a disease in a sample containing at least one cell, comprising:

contacting the sample containing at least one cell and an intracellular stain formulation for a targeted intracellular biomarker to form an intracellular reaction product within a closed Q-card if the targeted intracellular biomarker is present;

imaging the intracellular reaction product with an imager to generate an image of the intracellular reaction product;

analyzing the image to generate an analysis of the intracellular reaction product to determine the presence and the quantity of one or more intracellular biomarker; and generating at least one disease diagnosis by correlating the determined presence and the quantity of one or more intracellular biomarker measured in the method with a database of correlated biomarker and disease combinations.

The intracellular stain formulation comprising protein detection probe, nucleic acid detection probe (e.g. RNA, DNA), cell permeabilizing reagent, fixing reagent, or any combination.

A method for correlating a measured intracellular biomarker in a first cell with a measured diseased second cell or an organism having the diseased second cell, comprising:

- contacting a sample containing at least one cell and an intracellular stain formulation to form an intracellular reaction product within a closed Q-card;
- imaging the intracellular reaction product with an imager to generate an image of the intracellular reaction product;
- analyzing the image to generate an analysis of the intracellular reaction product to determine the presence and the quantity of the measured intracellular biomarker; and
- generating at least one disease diagnosis by correlating the determined presence and the quantity of the measured intracellular biomarker with a database of correlated biomarkers and disease combinations.

In one or more embodiments, the present invention provides, for example:

A method for determining the presence and the quantity of one or more intracellular biomarkers indicative of a disease in a sample containing at least one cell, comprising:

contacting the sample containing at least one cell and an intracellular stain formulation for a targeted intracellular biomarker to form an intracellular reaction product within a closed Q-card if the targeted intracellular biomarker is present;

- imaging the intracellular reaction product with an imager to generate an image of the intracellular reaction product;
- analyzing the image to generate an analysis of the intracellular reaction product to determine the presence and the quantity of one or more intracellular biomarker; and
- generating at least one disease diagnosis by correlating the determined presence and the quantity of one or more intracellular biomarker measured in the method with a database of correlated biomarker and disease combinations.

A method for correlating a measured intracellular biomarker in a first cell with a measured diseased second cell or an organism having the diseased second cell, comprising:

- contacting a sample containing at least one cell and an intracellular stain formulation to form an intracellular reaction product within a closed Q-card;
- imaging the intracellular reaction product with an imager to generate an image of the intracellular reaction product;
- analyzing the image to generate an analysis of the intracellular reaction product to determine the presence and the quantity of the measured intracellular biomarker; and
  - generating at least one disease diagnosis by correlating the determined presence and the quantity of the measured intracellular biomarker with a database of correlated biomarkers and disease combinations.

Example-A

TB Detection Using INSA

A method for detecting whether a subject having TB, comprising:

a. get a sample (e.g. sputum, swab, etc.) from the subject;

b. detecting, directly in the sample, either a TB bacteria or a subject's cell (e.g. blood cell, epithelial), wherein the detection comprising stain the bacteria and/or the cell;

wherein the staining comprising intra-cellular assay to stain either a TB specific protein or a TB specific nucleic acid inside cell; wherein, in some embodiments, stain the bacteria.

In some embodiments, QMAX card is used in the step (b). In some embodiments, smartphone is used in step (b).

In some embodiments, the step b comprising the steps:

a. dropping a sample on the QMAX card and closing the card;

b. observing, without washing, the staining of TB bacteria and/or the subject's cell.

Example-B

Influenza Detection Using INSA

A method for detecting whether a subject having influenza, comprising:

a. get a sample (e.g. nose secretes, nose swab, etc.) from the subject;

b. detecting, directly in the sample, either an influenza virus or a subject's cell (e.g. blood cell, epithelial), wherein the detection comprising stain the an influenza virus and/or the cell; wherein the staining comprising intra-cellular assay to stain either an influenza virus specific protein or an influenza virus specific nucleic acid inside cell; wherein, in some embodiments, stain the influenza virus using INSA.

In some embodiments, QMAX card is used in the step (b). In some embodiments, smartphone is used in step (b).

In some embodiments, the step b comprising the steps:

a. dropping a sample on the QMAX card and closing the card;

b. observing, without washing, the staining of the influenza virus and/or the subject's cell.

3. Quantification of a Cell-Fee Biomarkers in a Sample Using INSA

Other aspects of the present invention include, not limited to:

Use INSH for detection mRNAs inside cells in undiluted whole blood (e.g. inside white blood cells).

Use instant intra-cellular single-cell assay (ISIM) to detect cytokines inside of cells in whole blood, and converted into the free cytokins outside the cells in the whole blood.

Additional exemplary biomarkers to be detected by INSH and ISIM to identify bacteria infection and viral infection.

A method for quantifying a cell-free biomaker in a whole blood, comprising:

(a) having a blood sample that contains and is suspected of containing the cell-free biomarker;

(b) detecting and quantifying the biomaker inside a cell in the whole blood by specific intra-cellular protein immune-detection;

(c) detecting and counting the cells that contain the biomarker;

(d) calculating a total signal by multiplying the detected signal of the biomarker in each cell (detected and quantified in step (b)) by the total number of the cells that contain the biomarker (detected and counted in step (c)); and (e) related the total signal to the concentration of the biomarker free in the whole blood.

In some embodiments, the whole is undiluted.

In some embodiments, the cells are placed between two plates.

An exemplary method for INSH images analysis, comprising:

a. having a whole blood sample that contains or is suspected of containing a biomaker;

b. performing specific intra-cellular RNA hybridization detection to a labeled RNA detection agent to specifically hybridize the RNA related to the biomaker, wherein the detection comprising imaging using an imager (e.g. microscope);

c. opening microscope images by an image software.

d. Obtaining average fluorescent signals of each cells from the image and background signals(noise);

e. Calculating signal (S) to noise (N) ratio by using formula: (S−N)/N for each images (T), 9-20 images for each assay condition, to ach f. Using B2M house keeping gene as internal control. Running the same analysis for B2M images as targeted genes (C)

g. Normalizing the RNA signal for the biomarker by taking a ratio of the signal to that its own B2M internal control and reported as T/C;

h. Relating the normalized signal with the cell-free biomarker concentration in the whole blood.

An example of Quantification of intracellular protein expression level using ISIM, comprising a. having a whole blood sample that contains or is suspected of containing a biomaker;

b. performing specific intra-cellular protein immuno detection to a labeled protein detection agent to specifically bind to the biomaker, wherein the detection comprising imaging using an imager (e.g. microscope);

c. after 1 min staining of intracellular protein using ISIM, (e.g. 9-20 bright field and correspondent fluorescent images are taken using iPhone or microscope);

d. Images are then analyzed and reported using software with the listed parameters: comprising The blood sample comprising a whole blood, undiluted whole blood, diluted whole blood, or white blood cells.

Nt: total number of pictured cells

Np: number of positively stained cells

% Np/Nt: percentage of Np over Nt

Fn: Fluorescent intensity from each pictured cell

MF: Mean of positive fluorescent intensity from positively stained cells

TF: total positive fluorescent intensity by multiplying MF with % Np/Nt.

3) There are four levels of results representing the quantity of intracellular protein level based on the biological diagnostic feature of the biomarker:

A. % Np/Nt, when percentage of positivity is crucial for diagnosis;

B. Fn, when protein level in any positively stained cells is crucial for diagnosis;

C. MF and TF, when both percentage of positivity and fluorescent intensity are crucial for diagnosis.

D. All parameters, when all parameters are crucial for diagnosis.

Exemplary Biomarkers for identification of bacterial infection and virus infection

| Infectious disease and antibiotic resistance biomarkers | |
|---|---|
| Cytokine | IL-1, IL-2, IL-4, IL-5, IL-6, IL-7, IL-8, IL-9, IL-10, IL-12, IL-13, IL-15, IL-17, IL-18 |
| Interferon | Interferon gamma, Interferon alpha |
| Chemokine | IP-10, PF-4, Eotaxin, MCP-1, MIP-1 alpha, MIP-1 beta, RANTES |

-continued

| Infectious disease and antibiotic resistance biomarkers | |
|---|---|
| Tumor necrosis factors | TNF alpha, TRAIL |
| Other cytokines | GM, VEGF, Ang-1, Ang-2, G-CSF |
| Other biomarkers | CRP, PCT, Calprotectin, sTie-2, CC16, Neopterin, sTie-1, sTREM-1, suPAR, FGF, sVEGF-R, PDGF-BB |
| Genes classifier | ACTR2 IFNGR2 OAS2 AGER ISG15 OAS3 ARAP3 ITGA2B OASL EP300 ITGAM OSBPL8 F13A1 ITGAX OTOF GNG11 ITGB3 PROS1 HERC5 ITGB5 RSAD2 IFI27 MAP2K4 SORL1 IFI6 MT2A SPATS2L IFIT1 MYL9 VHL IFNGR1 OAS1 ZYX; ALPL GYG1 MPO C19orf59 HK3 ORM1 CD247 HLA-DMB PFKFB3 CD3D HP PGYRP1 CD7 IFITM3 PRTN3 CEACAM1 IL18R1* PSTPI2 CKAP4 IL18R1* RETN CSF3R IL1R2 RNF24 DYSF IL1RN S100A12 FCGR1A ITGAM SLC2A3 FFAR2 ITM2A SP11 FGR* LCN2 SRCAP-like FPR2 LIME1 STXBP2 FPR84 LRRN3 TNFAIP6 G4GALT5 MAL TRAJ17 GRAP MMP9 TRBV28 GRINA; BTN3A3 IFIT3 OASL IFI27 KIAA1618 PARP9 IFI44 OAS2 RSAD2 IFIT2; ADAR IFIT1 OAS2 ATF3 IFIT2 OAS3 C13orf18 IFIT3 OASL CCL2 IFIT5 PPIA CTSL1 IL16 PRSS21 CUZD1 ISG15 RPL30 DDX58 LAMP3 RSAD2 ENOSF1 LILRB2 RTP4 GAPDH LILRB1 4-Sep GBP1 LOC26010 SERPING1 GM2A LY6E SIGLEC1 HERC5 MX1 SOCS1 HLA-DOB NDUFA10 SOCS2 IFI27 NLRP3 SOCS5 IFI44 NOD2 TNFAIP6 IFI44L OAS1 XAF1 IFI6. |

Figure 12:
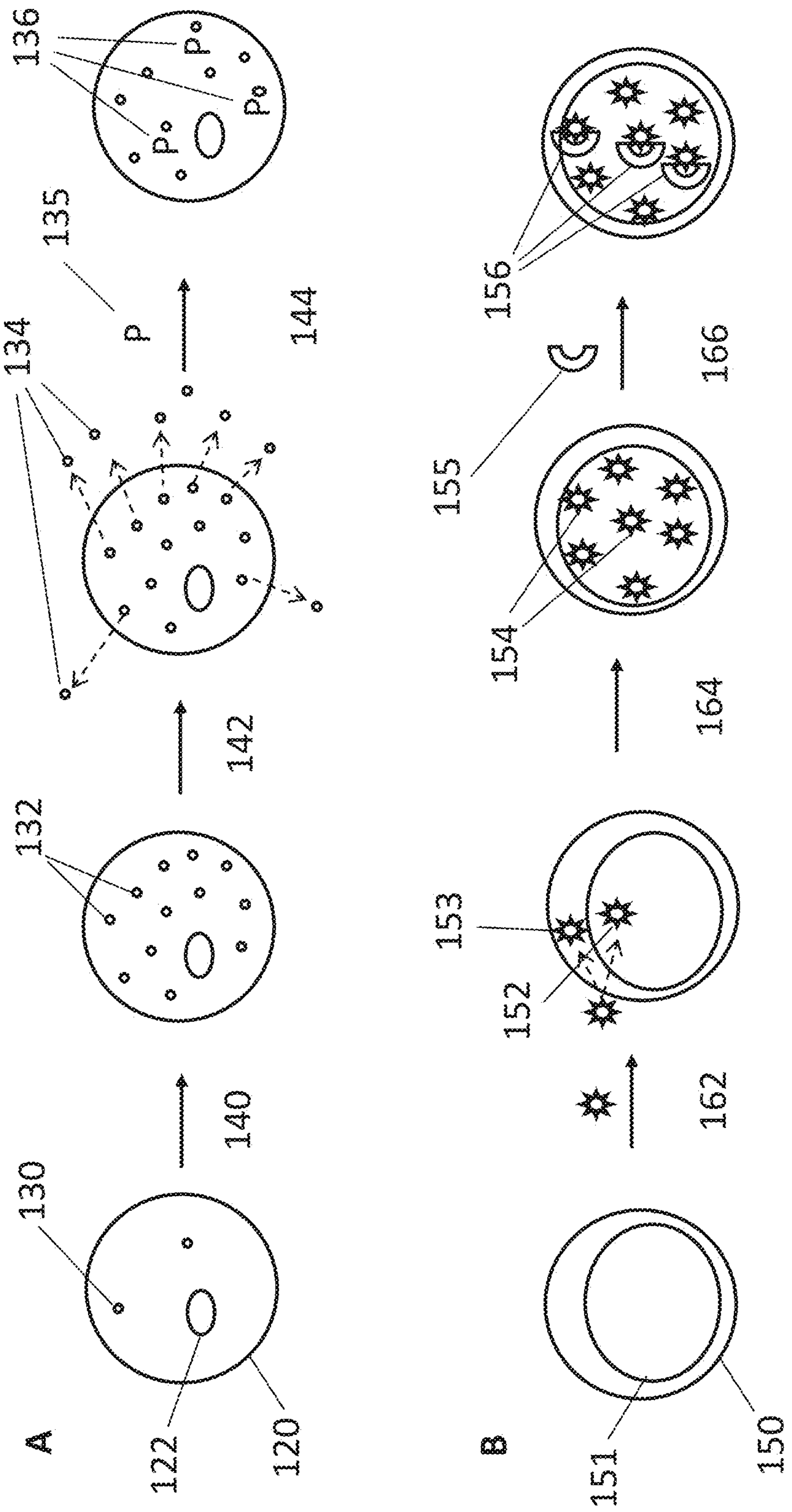
FIG. 12 shows schematics A and B of exemplary intracellular detection embodiments.

FIG. 12 shows schematics A and B of exemplary intracellular detection embodiments.

Schematic A illustrates the antecedent infection of a healthy white blood cell (WBC)(120) having a nucleus (122) and a normal level of a cytokine such as IL-6 (130). The WBC is infected (130) by a disease agent (not shown) which produces a proliferation or production of elevated levels or abnormal levels of IL-6 (132). The infected WBC secretes (134) IL-6 extracellularly into the plasma or the serum surrounding the infected WBC. The proliferation and secretion of the IL-6 can occur close in time or nearly simultaneously. In the present invention a probe ("P"; 135) molecule is added (144) to the sample containing the infected WBC to contact the intracellular IL-6 and form an intracellularly detectable complex or a reaction product ("P°"; 136) between the probe and the IL-6 target biomarker. The intracellular complex ("P°") is detected by an imager to generate an image. The image is analyzed by software to determine the presence and quantity of the IL-6 intracellular biomarker. The determined presence and quantity of the IL-6 intracellular biomarker is correlated with a database of extracellular biomarker and disease combinations, such as a correlated IL-4 and IL-6 extracellular biomarker and a bacterial infection disease (see Example 1). The quantity of the induced intracellular IL-6 positively correlates with the plasma or serum IL-6 level.

Schematic B in FIG. 12 illustrates the antecedent viral infection of a healthy cell (150), e.g., a CD4, a T-cell, a lymphocyte, having a nucleus (151) and a normal level of IL-6 (130). The healthy cell (150) is infected (162) by a virus particle. The viral infection can replicate (164) intra-nuclearly (152) or extra-nuclearly (153) to produce elevated levels or abnormal levels or disease level of virus particles (154). In the present invention a viral specific probe ("C"; 155) is added (166) to the sample containing the infected cell to contact the intracellular virus particles and form a detectable complex ("C*"; 156) between the viral specific probe and the intra-cellular and intra-nuclear target biomarker (see Example 3).

Figure 1B:
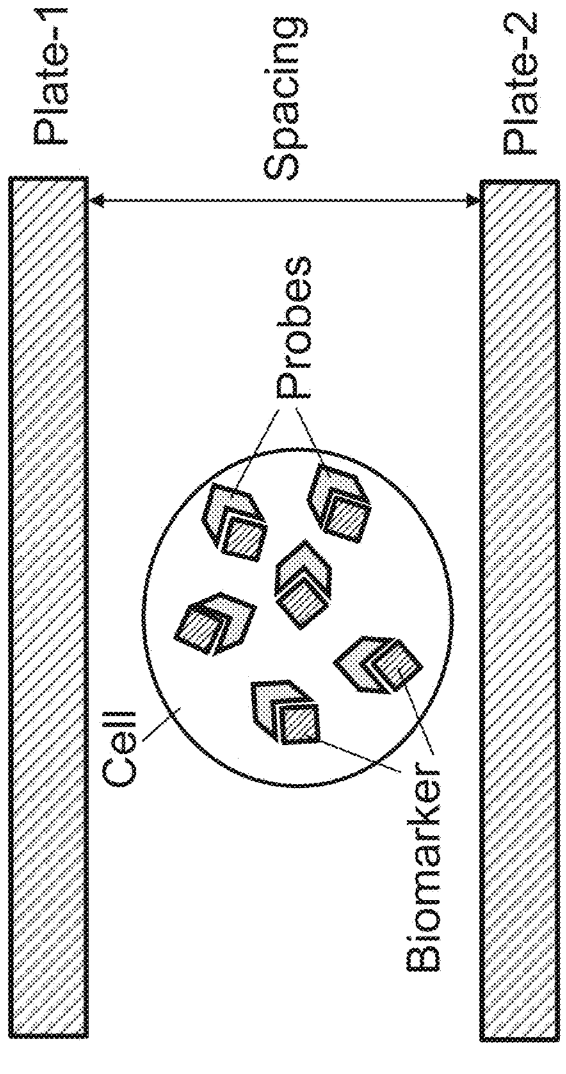
Figure 1C:
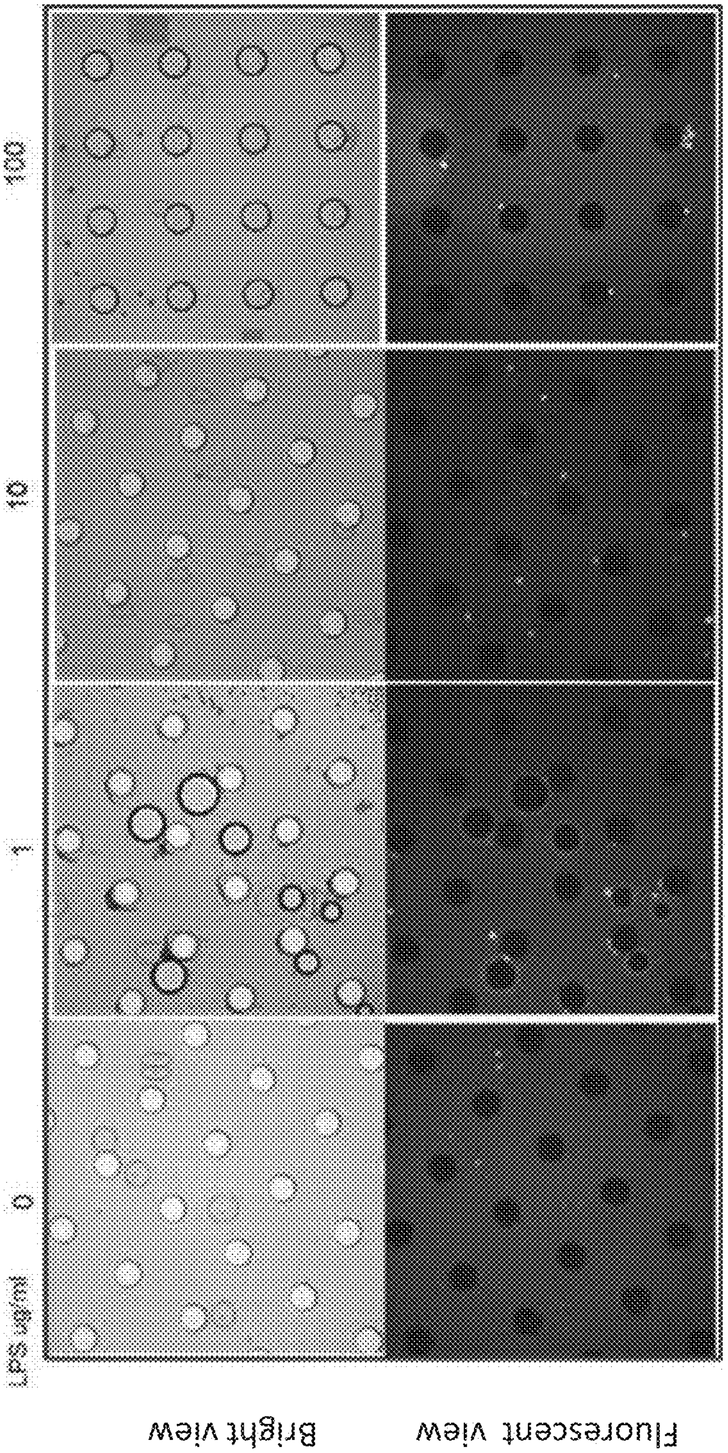
FIG. 1C shows an example result for instant intra-cellular single-cell hybridization (INSH) of Alexa488-IL-6 a 60-mer oligo probe with whole blood.

Referring to the Figures, FIG. 1C. shows an example result for instant intra-cellular single-cell hybridization (INSH) of Alexa488-IL-6 a 60-mer oligo probe with whole blood. Fresh whole blood was stimulated by LPS for 5 hours and hybridized with Alexa488 labeled IL-6 oligo probe in INSH (instant intra-cellular single-cell hybridization) for detection of IL-6 mRNA expression and imaged by a fluorescent microscope with excitation at 490 nm. The red circles in the images indicated white blood cells in the bright view (upper panel). The fluorescent view images showed fluorescent signals of IL-6 positive cells (light spots; lower panel).

Figure 2:
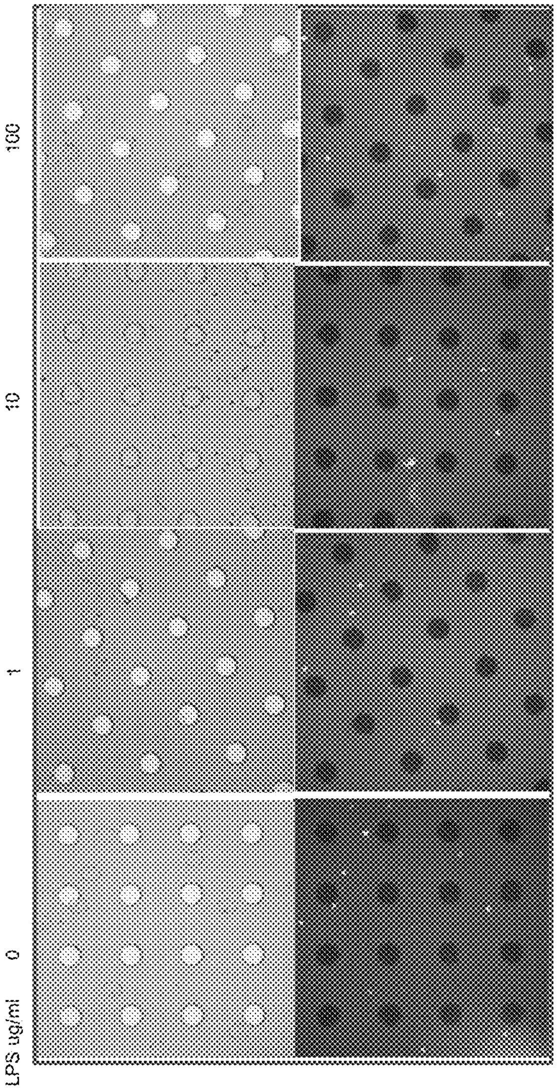
FIG. 2 shows an example result for instant intra-cellular single-cell hybridization (INSH) of Alexa 647-B2M (housekeeping genes) 60-mer oligo probe with whole blood.

FIG. 2 shows an example result for instant intra-cellular single-cell hybridization (INSH) of Alexa 647-B2M (housekeeping genes) 60-mer oligo probe with whole blood. Fresh whole blood was stimulated by LPS for 5 hours and hybridized with an Alexa 647 labeled IL-6 oligo probe in INSH for detection of B2M mRNA expression and imaged by a fluorescent microscope with excitation at 650 nm. The red circles showed white blood cells in the bright view (upper panel). The fluorescent view images showed fluorescent signals of B2M positive cells (light spots; lower panel).

Figure 3:
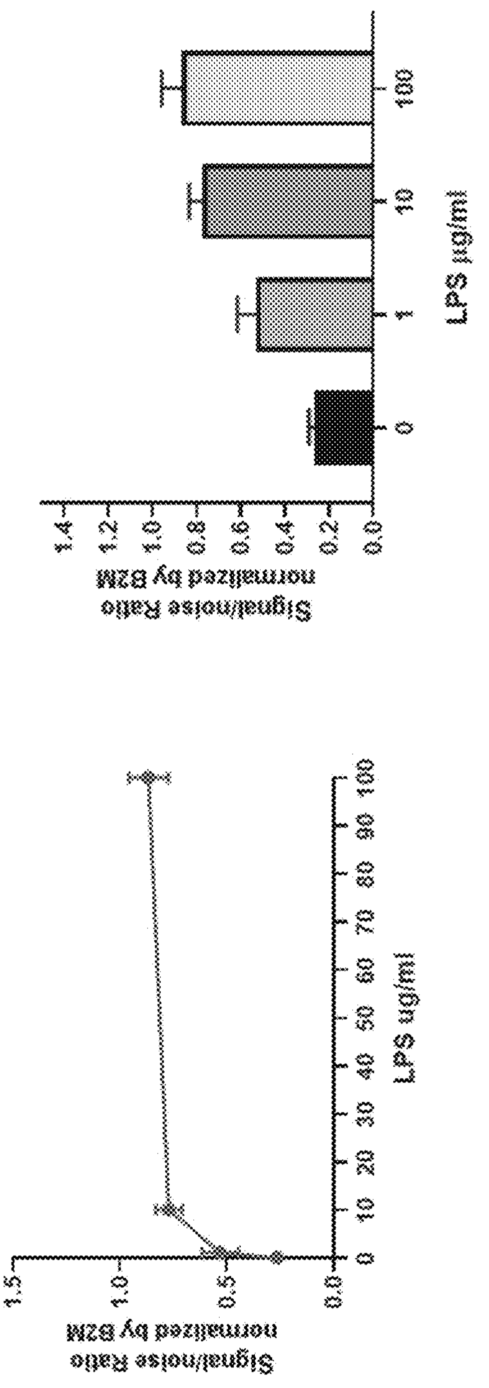
FIG. 3 shows INSH results of IL-6 expression in white blood cells which showed a dose dependent pattern with LPS induction.

FIG. 3 shows INSH results of IL-6 expression in white blood cells which showed a dose dependent pattern with LPS induction. The left panel shows a plot curve of LPS doses dependent IL-6 expression. The right panel shows a bar chart representation of the same data in left panel. The signal/noise ratios of IL-6 were normalized by B2M internal controls.

Figure 4:
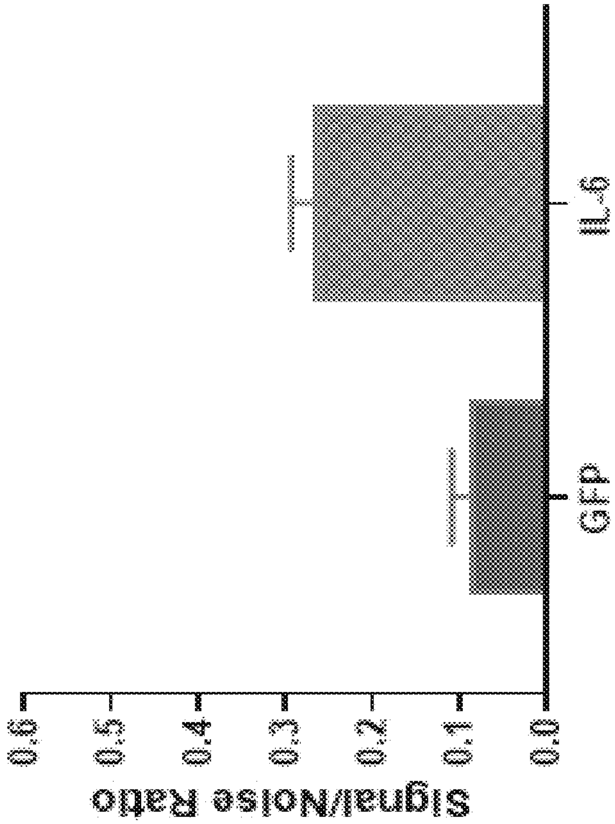
FIG. 4 shows Basal IL-6 expression (mRNA) compared with a negative control GFP (green fluorescent protein) in INSH.

FIG. 4 shows Basal IL-6 expression (mRNA) compared with a negative control GFP (green fluorescent protein) in INSH. The basal level of IL-6 mRNA was significantly higher than the signals of the negative control GFP, indicating that IL-6 was expressed in white blood cells without LPS stimulation.

Figure 5:
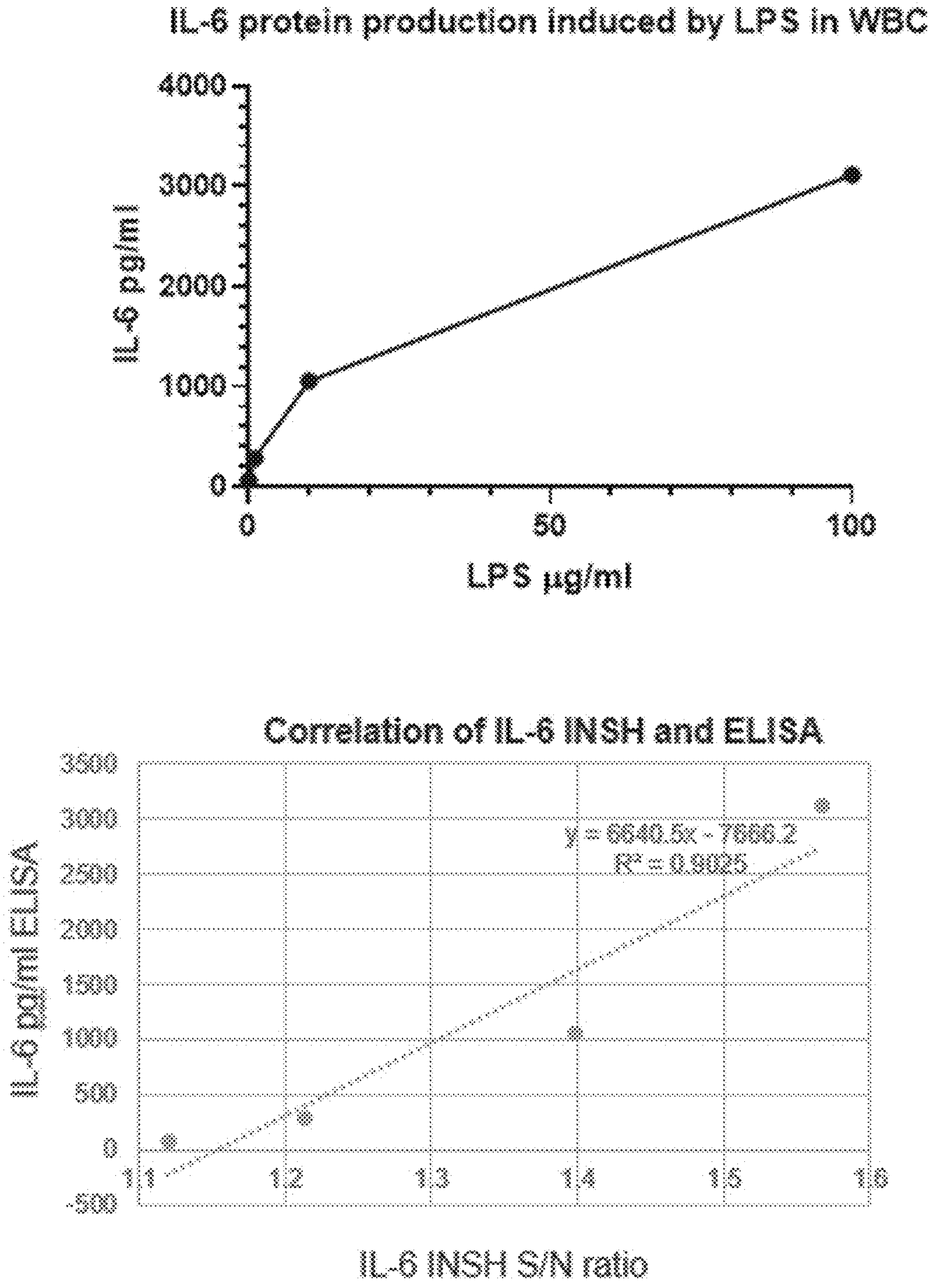
FIG. 5 shows a comparison of IL-6 mRNA expression (INSH) and protein production (ELISA) in white blood cells (WBC) with LPS induction.

FIG. 5 shows a comparison of IL-6 mRNA expression (INSH) and protein production (ELISA) in white blood cells (WBC) with LPS induction. The left panel showed a dose dependent LPS induction of IL-6 protein production detected by ELISA. The right panel showed the comparison of LPS induced IL-6 mRNA expression (INSH) and IL-6 protein production (ELISA). The IL-6 INSH and ELISA data correlated well. The R2 value was 0.9025.

Figure 6:
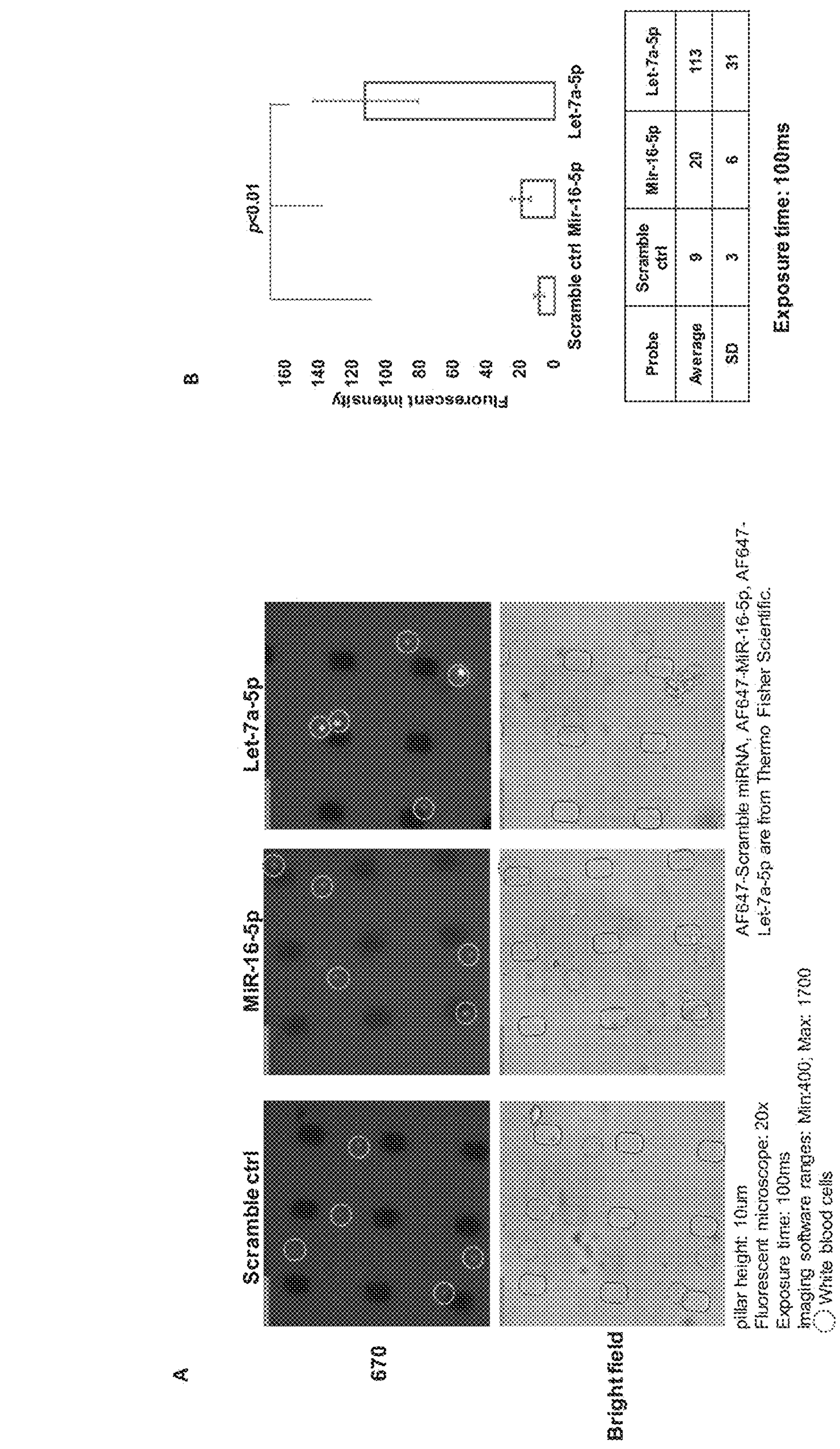
FIGS. 6A and 6B shows INSH miRNA staining results of white blood cells from the fingertip blood of a healthy donor.

FIGS. 6A and 6B show INSH miRNA staining results of white blood cells from the fingertip blood of a healthy donor.

FIG. 6A shows representative images of INSH miRNA staining of white blood cells from the fingertip blood from a healthy human donor. The upper panel shows fluorescent images taken with a filter 670 nm. The lower panel shows the corresponding bright field images of the fluorescent images. From left to right: AF647-scramble control miRNA probe; AF647-Mir-16-5p; and AF647-Let 7-5p miRNA probe stained results of white blood cells indicated by the circles (red). These miRNA probes were from Thermo Fisher Scientific. FIG. 6B shows a bar chart of fluorescent intensities from each condition shown in FIG. 6A and were analyzed using Image J software. Data were collected and listed in the table (lower) and presented as bar chart (upper).

Figure 7:
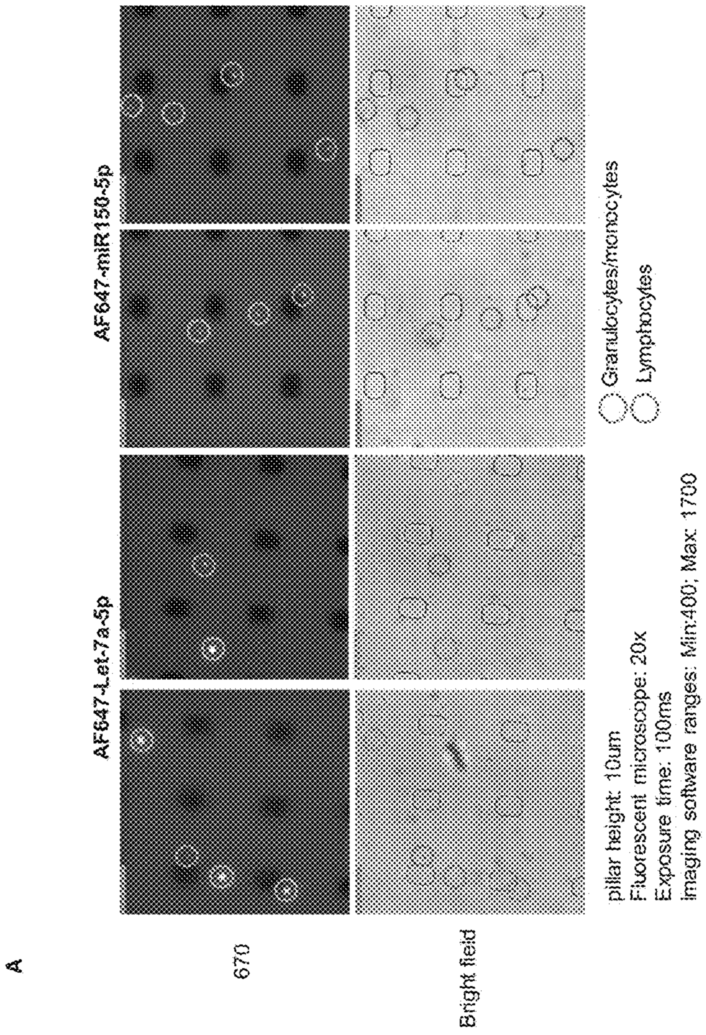
FIGS. 7A and 7B shows INSH AF647-Let-7a-5p and AF647-miR150-5p results of staining white blood cells from fingertip blood from a healthy donor.
Figure 7:
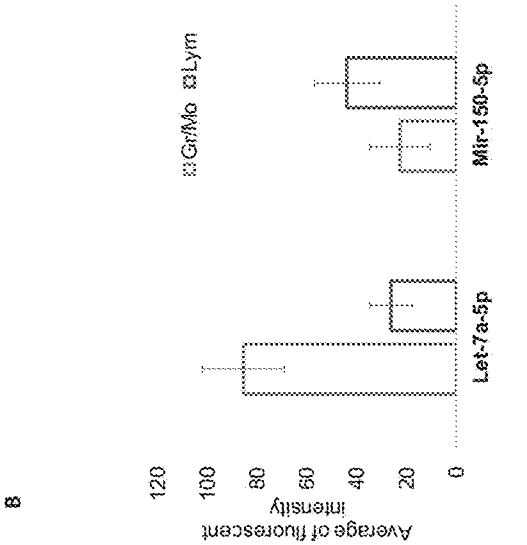

FIGS. 7A and 7B show INSH AF647-Let-7a-5p and AF647-miR150-5p results of staining white blood cells from fingertip blood from a healthy donor. FIG. 7A shows representative images of INSH staining of Let-7a-5p and miR150-5p in granulocytes and monocytes circles (red) and lymphocytes circles (blue) from fingertip blood from a healthy donor. AF647-Let-7a-5p predominantly stained granulocytes/monocytes; AF647-miR150-5p predominantly stained lymphocytes. FIG. 7B shows fluorescent intensities from each condition as shown in FIG. 7A and were analyzed using Image J software. The data were collected and listed in the table (lower) and presented as bar chart (upper). AF647-Let-7a-5p expressed significantly higher in granulocytes/monocytes (left bars). However, AF647-miR150-5p expressed significantly higher in lymphocytes (left bars).

Figure 8:
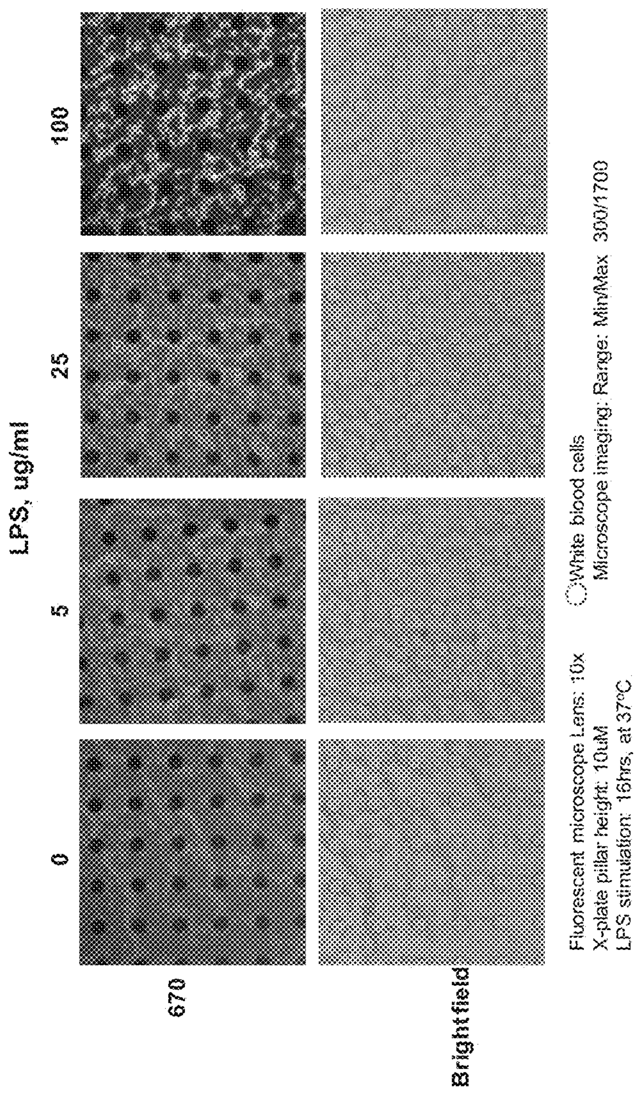
FIG. 8 shows instant intra-cellular single-cell immunoassay (ISIM) AF647-anti-IL6 staining of LPS stimulated white blood cells in fresh human whole blood.

FIG. 8 shows instant intra-cellular single-cell immunoassay (ISIM) AF647-anti-IL6 staining of LPS stimulated white blood cells in fresh human whole blood. After fresh human whole blood was incubated with various concentration of LPS for 16 hrs at 37° C., the white blood cells in LPS stimulated whole blood were stained with AF647-anti-IL6 antibody. Representative fluorescent images (670 nm) are shown in the upper panel, and bright field images corresponding from fluorescent images are shown in the lower panel. White blood cells are indicated in circles (red).

Figure 9:
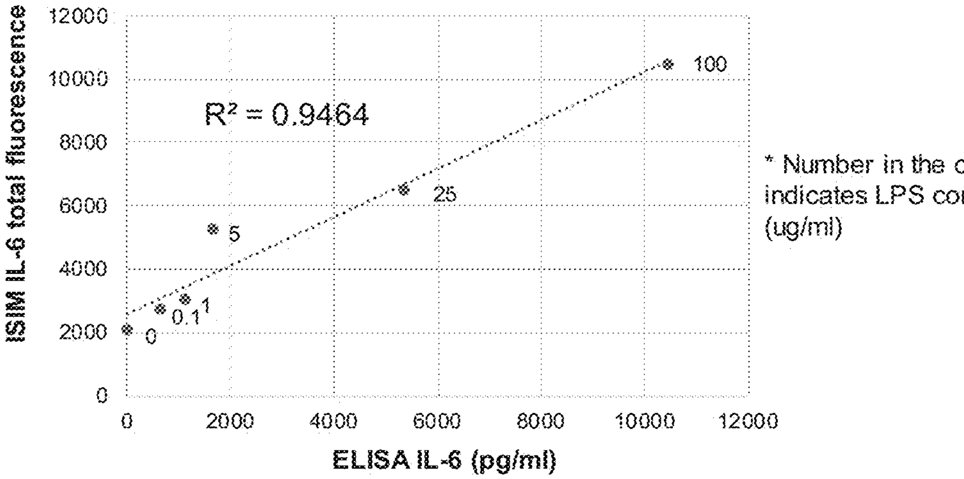
FIG. 9 show experimental results for instant intra-cellular single-cell immunoassay (ISIM) IL-6 staining and a total fluorescence intensity correlation with the ELISA plasma IL-6 level.

FIG. 9 show experimental results for instant intra-cellular single-cell immunoassay (ISIM) IL-6 staining and a total fluorescence intensity correlation with the ELISA plasma IL-6 level. Fluorescent intensity and percentage of IL-6 (+) cells from all images in LPS stimulated experiments (as shown in representative images in FIG. 2) were analyzed using Image J software. The ISIM total fluorescence was multiplied by fluorescence intensity and the % of IL-6 (+) cells as shown in the table listing (lower). Half of the LPS stimulated blood from the experiment in FIG. 2 was centrifuged and the plasma was collected for ELISA analysis of the soluble IL-6 level as shown in the table listing (lower). ISIM total fluorescence and soluble IL-6 level by ELISA were plotted in graph (upper). There is a significant linear correlation of the two parameters ($R^2$=0.9464).

Figure 10:
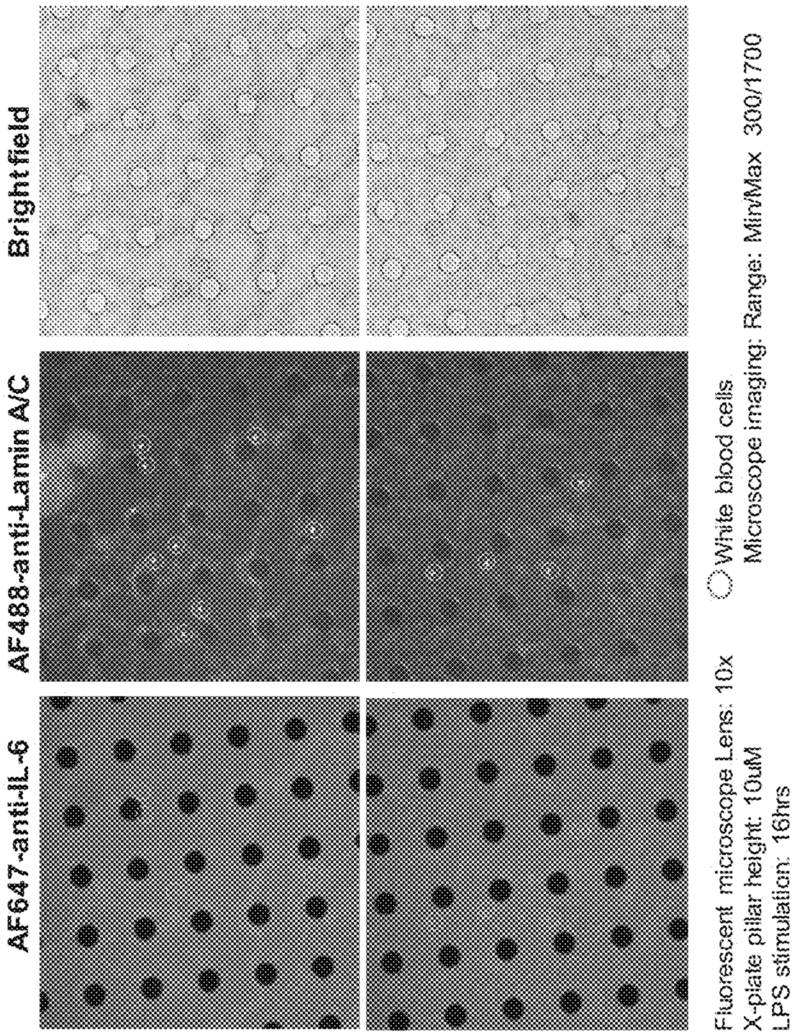
FIG. 10 show experimental results for ISIM double staining of IL-6 and Lamin A/C of white blood cells in fresh human whole blood.

FIG. 10 show experimental results for ISIM double staining of IL-6 and Lamin A/C of white blood cells in fresh human whole blood. Fresh whole blood was co-stained with AF647-anti-IL6 (left panels) and AF488-anti-Lamin A/C (middle panels). AF647-anti-IL6 fluorescent images were taken using a 670 nm filter (left panels); AF488-Lamin A/C fluorescent images were taken using a 495 nm filter (middle panel); and the corresponding bright field images are shown in the right panel. White blood cells are indicated in aperiodic open circles (red). The periodic circles are spacers in the sample Qcard.

Figure 11:
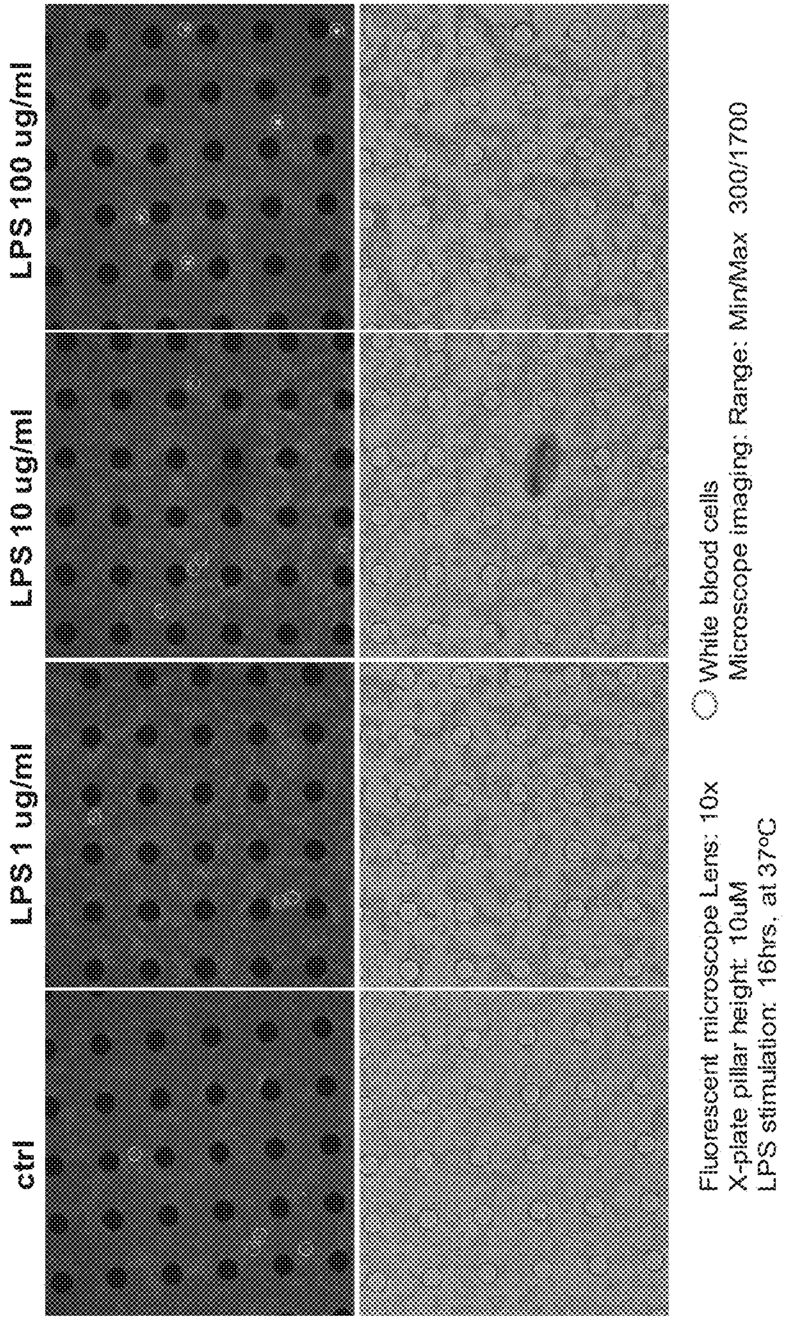
FIG. 11 show experimental results for ISIM AF647-anti-IFN-γ staining of LPS stimulated white blood cells in human whole blood.

FIG. 11 show experimental results for ISIM AF647-anti-IFN-γ staining of LPS stimulated white blood cells in human whole blood. After fresh human whole blood was incubated with various concentrations of LPS for 16 hrs at 37° C., white blood cells in LPS stimulated whole blood were stained with the AF647-anti-IIFN-γ antibody. Representative fluorescent images are shown in upper panels, and the lower panels are bright field images for the corresponding fluorescent images. White blood cells are indicated in aperiodic open circles (red). The periodic circles are spacers in the sample Qcard.

In certain embodiments, machine learning is utilized to analyte the images captured in the INSA. In certain embodiments, the machine learning comprising a use of the spacers and/or monitoring marks in the sample that are captured by the image together with the sample.

Example-C

INSH for mRNA in fresh whole blood

Materials:

1. Obtaining Fresh whole blood samples
2. Performing INSH fluorescence-labeled oligo probes were customer designed and made by Integrated DNA technology

```
2.1. IL-6 Alexa488 60-mer oligo probe:
                                        (SEQ ID NO: 1)
5'Alex488N/TCTGCAGGAACTGGATCAGGACTTTTGTACTCATCTG

CACAGCTCTGGCTTGTTCCTCAC

2.2. B2M Alexa647 60-mer oligo probe:
                                        (SEQ ID NO: 2)
5'Alexa647N/ATC TTCAAACCTCCATGATGCTGCTTACATGTC TCG

ATCCCACTTAACTATCTTGGGCT

2.3 GFP Cy5 60-mer oligo probe:
                                        (SEQ ID NO: 3)
5'Cy5N/ATGGCGGACTTGAAGAAGTCGTGCTGCTTCATG

TGGTCGGGGTAGCGGCTGAAGCACTGC
```

3. Formamide (Sigma Cat #F9037)
4. Zwittergent 3-14 detergent (EMD Millipore, Cat #693017)
5. Lipopolysaccharides (LPS, Sigma, Cat #L-4391)

Methods

1. Qcard preparation: Treat an X-plate (top plate):
    1.1. with 1 M NaOH at 50° C. for 1 hour and briefly washed with 1×PBS two times
    1.2. coat with 4% BSA at room temperature for 2 hours and briefly rinse twice with water
    1.3. dry on paper towel
2. Blade-coating of hybridization solution on the BSA coated X-plate:
    2.1. Preparation of hybridization solution: 2×SSC, lx Denhardt's solution, 50 mM sodium phosphate buffer (pH7.2), 3% formamide, 12 mg/ml Zwittergent, and 1 uM fluorescent-labeled oligo probe
    2.2. Blade-coating: 5 microliters of hybridization solution deposited onto a X-plate and the hybridization solution is spread back and forth over the whole plate once with a blade
    2.3. The blade-coated plates were air-dried for 30 minutes and ready to use
3. LPS (lipopolysaccharides from *E. coli*) stimulation for cytokine release:
    3.1. Fresh whole blood samples were mixed with an equal volume of cell culture medium RPMI (Roswell Park Memorial Institute (RPMI) 1640 Medium)

3.2. LPS was added to indicated concentrations and the samples were incubated at 37° C. with constant rotation for 5 hours

4. INSH:

4.1. Blade-coating X-plate (top plate) with hybridization solution, and let it dried at room temperature.

4.2. 3.5 microliters of a fresh blood sample is deposited on a substrate plate (M-plate base)

4.3. Place pre-coated X-plate on the blood sample on the substrate (bottom plate) and pressed together to close the card. The substrate or M-plate has 10 uM pillar or spacer height.

4.4. The closed card is incubated at room temperature for 2 minutes and then imaged with a microscope

Example-D

INSH miRNA in Fresh Whole Blood (in 60 Seconds)

Materials:

1. Fresh human whole blood.
2. Q-Card: 5 um or 10 um pillar height.
3. Alexa Fluor labelled miRNA probes, 1 uM stock concentration. All probes are from Thermo Fisher Scientific.
4. The FISH hybridization buffer is from BioSearch Technologies.

Procedure: Mix 5 microliters of whole blood with 5 microliters of hybridization buffer and 0.5 microliters Alexa Fluor labelled miRNA probe on the bottom of the Q-Card. Close the Q-Card and incubate at room temperature for −1 min and immediately observe using an iPhone having a Qcard adapter or a fluorescent microscope. The observation includes imaging, recording, and analyzing, an image to generate a disease diagnosis from a correlated biomarker and disease database.

Example-E

Instant Intra-Cellular Single-Cell Assay (ISIM) Cytokines in Fresh Whole Blood Materials:

1. Fresh human whole blood;
2. Q-Card: 5 um or 10 um pillar height.
3. Antibodies, 0.6 mg/ml antibody in PBS.
   3.1 anti-human IL-6 and anti-human IFN-γ from R&D Systems
   3.2 AF647 labelling kit from Thermo Fisher Scientific
   3.3 AF488-anti-Lamin A/C from Cell Signaling
4. Staining solution: 60% ethanol, 5% Zwittergent 3-14, and 1% Tween-20

Procedure:

1. Mix 2 microliters of whole blood with 4 microliters of staining solution and 0.5 microliters antibody on the bottom plate of the Q-Card;
2. Close the Q-Card, incubate at room temperature for −1 min, and immediately ready for observation of using a fluorescent microscope or an iPhone adapted camera. The observation includes imaging, recording, and analyzing, an image to generate a disease diagnosis from a correlated biomarker and disease database.
3.

Examples of QMAX Cards

In some embodiments, the first plate and the second plate are connected by a hinge.

In some embodiments, the staining solution has a volume 2 uL(micro-liter) or less, 2 uL or less, 5 uL or less, 10 uL or less, 15 uL or less, 20 uL or less, 30 uL or less, 50 uL or less, 100 uL or less, or a range between any of the two.

In some preferred embodiments, the staining solution has a volume 2 uL(micro-liter) or less, 2 uL or less, 5 uL or less, 10 uL or less, 15 uL or less, 20 uL or less, 30 uL or less, or a range between any of the two.

In some preferred embodiments, the staining solution has a volume 2 uL(micro-liter) or less, 2 uL or less, 5 uL or less, 10 uL or less, 15 uL or less, or a range between any of the two.

4. Examples of INSA Applicable Diseases

The instant intra-cellular single-cell assay (INSA) provide a one-step chemical contact with the sample containing at least one cell including 60 sec or less incubation, imaging, analyzing, and reporting the presence and quantity of detected intracellular biomarkers, such as nucleic acids and proteins, directly from a fresh crude biological sample, such as a needle biopsy sample, whole blood, urine, sputum, saliva, swab samples (pap smear), and like samples. The INSA procedure provides advantages in diagnosis of, for example, diseases that have established or discoverable intracellular diagnostic biomarkers, for example: infectious diseases; malignant diseases; autoimmune diseases; metabolic diseases, and inherited genetic disorders. The tabulated listing below provides examples of sample sources (e.g., bodily fluid) or sample retrieval methods, disease categories, and diseases and conditions, where the disclosed INSA methodology can be used for diagnosis in accordance with the disclosed methods.

Some of INSA Biomarkers and/or process are given below.

INSA Biomarkers in whole blood samples:

| | |
|---|---|
| Blood cancer | Leukemia: Acute lymphocytic leukemia (ALL), Acute myeloid leukemia (AML), Chronic lymphocytic leukemia (CLL), Chronic myelogenous leukemia (CML); Lymphoma: Hodgkin's lymphoma, Non-Hodgkin's lymphoma; Multiple myeloma. |
| Infectious Disease | Inflammation symptom (cytokine storm), Virus infection (EBV, CMV, HIV, HBV, HCV, Influenza, yellow fever virus), Bacterial Neutropenia (Gram-negative aerobic bacteria (e.g., *Escherichia coli*, Klebsiella species, Pseudomonas aeruginosa), Viral Neutropenia (EBV, HBV, Yellow fever virus, CMV, influenza), Coronavirus (Sars, Mers, COVID-19) |
| Autoimmune disease | systemic lupus erythematosus (SLE), Rheumatoid Arthritis, Lupus, Dermatomyositis, Graves Disease, Psoriasis, Coeliac Disease. |

-continued

| | |
|---|---|
| Primary immunodeficiency (PID) | Cytokines deficiency (IFN-γ, interleukins and other), X-linked agammaglobulinemia (BTK protein), LRBA (LRBA protein), DOCK8 deficiency (DOCK8 protein) |
| Genetic diseases | Leukocyte adhesion deficiency, Myeloperoxidase deficiency |

urine samples:

| | |
|---|---|
| Benign urinary tract diseases and conditions | Lithiasis (stones); cystitis (most common infection caused by *E. Coli.*), special infections (human polyomavirus, cytomegalovirus (CMV), herpesvirus, human papillomavirus (HPV), tuberculosis (TB), fungus, parasites (schistosomiasis) miscellaneous organisms), other types of cystitis (eosinophilic cystitis, malakoplakia)]; intravenous and retrograde pyelogram effect (radiologic contrast material); heavy metal poisoning; renal transplant; therapeutic effects (chemotherapy: cyclophosphamide (cytoxan), busulfan, thiotepa, mitomycin, cyclosporine, nephrogenic adenoma |
| Urinary tract cancer | Urothelial neoplasia (papilloma), urothelial carcinoma (bladder cancer, papillary, flat/nodular, low grade and high grade, carcinoma in situ), leukoplakia, bladder condylomas, squamous cell carcinoma, adenocarcinoma, small cell carcinoma, sarcoma, mixed urothelial carcinoma, lymphoma/leukemia, mesenchymal tumors, secondary tumors (renal cell carcinoma, prostatic adenocarcinoma, melanoma, other metastasis from lung and breast) |

Biomarkers in Swab Samples:

| | |
|---|---|
| Benign diseases and conditions | Infectious diseases:<br>throat swab: strep throat, pneumonia, tonsillitis, whooping cough, and meningitis, HPV<br>nasal swab: upper respiratory infections (influenza respiratory syncytial virus, Bordetella pertussis infection (whooping cough) *Staphylococcus aureus* infections of the nose and throat), TB, virus infections (metapneumovirus, influenza A virus, parainfluenza virus, or respiratory syncytial virus), and Coronavirus (Sars, Mers, COVID-19).<br>Vaginal, cervix and uterus swabs: sexual transmitted diseases (Neisseria gonorrhoeae, Chlamydia trachomatis, and Trichomonas vaginalis), Pap test for HPV, Herpes virus, Candida albicans, Gardnerella vaginalis, Prevotella spp, Treponema pallidum.<br>Genetic diseases |
| Malignant diseases | hypopharyngeal cancer, nasopharyngeal cancer, oropharyngeal cancer, laryngeal cancer, lung cancer, nasal and sinus tumors (squamous cell carcinoma, adenocarcinoma, lymphoma, melanoma, esthesioneuroblastomas, osteomas), cervical cancers (squamous cell carcinomas, adenocarcinoma, small cell cancer), virginal cancers (squamous cell carcinomas, adenocarcinoma, clear cell carcinoma, melanoma), Urinary tract cancers (see urine samples) |

The following eight examples are the experiments being tested, as a part of embodiments of the present invention.

Example 1

Co-staining of IL-4 and IL-6 in white blood cells and white blood cells count in fresh human whole blood differentiates a bacterial infection from a virus infection. This experimental example illustrates instant intra-cellular single-cell immunoassay (ISIM), which is a simple assay that can accomplish a blood test that involves, for example, IL-4 and IL-6 staining and quantification. The method can differentiate, for example, a bacterial infection from a virus infection. An increase of IL-4 and IL-6 in blood is a significant biomarker for early bacterial infection. Increased IL-6 in blood shows a 50 to 64.3% sensitivity and an 82.8 to 97.1% specificity. An increased IL-4 in blood shows a 100% sensitivity and a 76.5% specificity of bacterial infection. Co-staining of IL-4 and IL-6 in white blood cells can significantly increase both sensitivity and specificity for differentiating a bacterial infection from other pathogens.

Sampling:

Deposit a drop of whole blood onto a Q-Card.

Staining and Imaging:

Mix the blood with a staining solution including PBS, Zwittgent 3-14, ethanol and AF488-anti-IL-4, and AF647-anti-IL6 antibodies.

Close Q-Card and incubate blood sample with staining solution at room temperature for less than 1 min.

Image white blood cells in the closed Q-Card using an iPhone having an adapter or a fluorescent microscope.

Experimental Results: An IL-4 level higher than 9 pg/ml or an IL-6 level higher than 0.15 pg/ml to <74.5 ng/ml, an increase of the total WBC count and high granulocytes, or both, are significant biomarkers for bacterial infection.

Example 2

Co-staining of IFN-γ and IL-2 in white blood cells from fresh human whole blood to determine an active Tuberculosis (TB) infection. A distinct profile of IFN-γ and IL-2 is an immunological marker of a mycobacterial load and a clinical status of tuberculosis. Receiver operator characteristics (ROC) analysis revealed that frequencies of purified protein derivative (PPD) specific IFN-γ/I L-2 dual-positive T cells below 56% were an accurate marker for active TB (specificity 100%, sensitivity 70%) enabling effective discrimination from non-active states.

Sampling: Deposit a drop of whole blood onto a Q-Card.

Staining and Imaging:

Mix blood with staining solution including PBS, Zwittergent 3-14, ethanol, and the antibodies AF488-anti-IFN-γ, AF647-anti-IL2, and AF590-anti-CD16.

Close the Q-Card and the incubate blood sample with the staining solution at room temperature for less than 1 min.

Image the white blood cells in the closed Q-Card using an iPhone having an adapter or a fluorescent microscope.

Experimental Results: IFN-γ/I L-2 dual-positive CD16(−) mononuclear cells below 56% indicates an active Tuberculosis (TB) infection.

Example 3

HIV Gag p24 antigen staining in white blood cells from fresh human whole blood to diagnose HIV infection. The percentage of HIV p24 antigen-positive cells detected in the peripheral blood of HIV-seropositive individuals is highly correlated with the clinical stage and an inverse correlation with the total number of T4 cells. Combination of detection of p24 in peripheral blood mononuclear cells and the total number of T4 cells are significant biomarkers to determining disease progression in HIV-seropositive individuals.

Sampling: Deposit a drop of whole blood onto a Q-Card.

Staining and Imaging:

Mix the blood with the staining solution including PBS, Zwittergent 3-14, ethanol, and antibodies AF488-anti-p24 and AF647-anti-CD4.

Close the Q-Card and incubate blood sample with staining solution at room temperature for less than 1 min.

Image the white blood cells in the closed Q-Card using an iPhone having an adapter or a fluorescent microscope.

Experimental Results: p24 (+) mononuclear cells higher than 4%, and/or decreased CD4 (+) cells can be diagnosed as an HIV-seropositive blood sample.

Example 4

INSH HIV RNA Gag-Pol Sequence Staining in White Blood Cells from Fresh Human Whole Blood to Diagnose HIV Infection.

Sampling and pre-printed Staining: Deposit a drop of whole blood onto a Q-Card. that comprises printed/coated dry staining material (AF488-HIV RNA Gag-pol probes and AF647-scramble control probes) on the Qcard top plate (X-plate).

Imaging: Close the Q-Card and incubate the blood sample in the microvolume embodiment at room temperature for less than 1 min;

Image the white blood cells in the closed Q-Card using an iPhone having an adapter or a fluorescent microscope.

Experimental Results: The percentage of HIV RNA Gap pol probes (+) mononuclear cells higher than 0.01% can be diagnosed as HIV-seropositive blood sample.

Example 5

HBsAg and HBcAg Staining in White Blood Cells from Fresh Human Whole Blood to Diagnose Hepatitis B (HBV) Infection.

Sampling: Deposit a drop of whole blood onto a Q-Card.

Staining and Imaging:

Mix the blood with the staining solution including PBS, Zwittergent 3-14, ethanol, and antibodies AF488-anti-HBsAg and AF647-anti-HBcAg.

Close the Q-Card and the incubate blood sample with the staining solution at room temperature for less than 1 min;

Image the white blood cells in the closed Q-Card using an iPhone having an adapter or a fluorescent microscope.

Experimental Results: HBsAg and HBcAg (+) peripheral blood mononuclear cells (PBMCs) higher than 5% can be diagnosed as HBV-positive patient sample.

Example 6

INSH HPV E6/E7 mRNA in Liquid-Based Cervical Cytology Specimen to Diagnose HPV Infection.

Sampling and Staining: Drop a liquid-based cervical cytology specimen onto the bottom plate of a Q-Card with dry print/coat HPV E6/E7 mRNA probes on the top plate of the Q-Card (X-plate);

Close the Q-Card and incubate the specimen sample with the staining solution at room temperature for less than 1 min; and Image, record, and analyze, the white blood cells in the closed Q-Card using an iPhone having an adapter or a fluorescent microscope.

Experimental Results: Observation of HPV E6/E7 mRNA (+) epithelial cells can be diagnosed as an HPV infection.

Example 7

ISIM HPV E6/E7 Protein in Liquid-Based Cervical Cytology Specimen to Diagnose HPV Infection Sampling and Staining:

1. Mix the liquid-based cervical cytology specimen with a staining solution including PBS, Zwittergent 3-14, ethanol, and AF488-anti HPV E6/E7 antibody;
2. Close the Q-Card and incubate the blood sample with the staining solution at room temperature for less than 1 min;
3. Image, record, and analyze, the white blood cells in the closed Q-Card using an iPhone having an adapter or a fluorescent microscope.

Experimental Results: Percentage of HPV E6/E7 protein (+) epithelial cells higher than 2% can be diagnosed as HPV positive specimen.

Example 8

ISIM CMV-Specific Early Antigen (Pp65) Staining in Peripheral Polymorphonuclear Leukocytes (PMNLs) to Diagnose CMV Infection.

Sampling: Repeat the sampling steps 1 to 3 of Example 1.

Staining and Imaging:

Mix blood with staining solution including PBS, Zwittgent 3-14, ethanol, and AF488-anti-pp65 antibody;

Close Q-Card and incubate blood sample with staining solution at room temperature for less than 1 min; and Image, record, and analyze, the white blood cells in the closed Q-Card using an iPhone having an adapter or a fluorescent microscope.

Experimental Results: pp65 (+) peripheral blood mononuclear cells (PBMCs) higher than 5% can be diagnosed as a CMV-positive patient sample.

Example 9

INSH Sars-Cov-2 Specific mRNA Probes Staining of Nasopharyngeal Epithelial Cells to Diagnose COVID-19

The genome of human SARS-CoV-2 shares 88% similarity with human SARS-CoV-1, 29% with human MERS, and 99% with Bat coronavirus RaTG13 as shown in FIG. 1. To specific diagnose COVID-19 using iMOST, I designed 11 listed probes targeting Orf1ab, Orf3 and Spike mRNAs of SARS-COV-2.

```
Orflab 5289-5349
                                          (SEQ ID NO: 4)
tagagcaggtggattaaacttcaactctatttgttggagtgttaacaatg

cagtggcaag

Orflab 6262-6322
                                          (SEQ ID NO: 5)
caactggttttgtgctccaaagacaacgtatacaccaggtatttggttta

tacgtggctt

Orflab 6702-6762
                                          (SEQ ID NO: 6)
agtacaaacacggtttaaacaccgtgtaactatgttagtagttgtactaa

caactttgtt

Orflab 20344 - 20404
                                          (SEQ ID NO: 7)
Ggtgattccttaaaacgtttagctagtccaatcagtagatgtaaaccacc

taactgacta

Orflab 1550 - 1607
                                          (SEQ ID NO: 8)
Ttgtcattaagaccttcggaaccttctccaacaacacctgtatggttaca

acctatgtta

Orf3a 25687-25746
                                          (SEQ ID NO: 9)
Ttatactctgcaagaagtagactaaagcataaagatagagaaaaggggct

tcaaggccag

Orf3a 25409-25469
                                         (SEQ ID NO: 10)
Tgaaggagtagcatccttgatttcaccttgcttcaaagttacagttccaa

ttgtgaagat

Spike 21750-21756
                                         (SEQ ID NO: 11)
Cctcttagtaccattggtcccagagacatgtatagcatggaaccaa

Spike 21995-22053
                                         (SEQ ID NO: 12)
Ttcgcactagaataaactctgaactcactttccatccaacttttgttgtt

tttgtggta
```

-continued

```
Spike 22276-22336
                                         (SEQ ID NO: 13)
Ccaacctgaagaagaatcaccaggagtcaaataacttctatgtaaagcaa

gtaaagtttg

Spike 22291-22349
                                         (SEQ ID NO: 14)
cagcaccagctgtccaacctgaagaagaatcaccaggagtcaaataactt

ctatgtaaa
```

Sampling and Staining:

Mix nasopharyngeal cytology swab with 100 ul of saline in a clean eppendorf tube.

Add 3-10 ul of nasopharyngeal saline mix onto the bottom plate of a Q-Card with dry print/coat Sars-cov-2 specific mRNA probes on the top plate of the Q-Card (X-plate);

Close the Q-Card and incubate the specimen sample with the staining solution at room temperature for less than 1 min; and Image, record, and analyze, the nasopharyngeal epithelial cells in the closed Q-Card using an iPhone having an adapter or a fluorescent microscope.

Experimental Results: Observation of Sars-cov-2 mRNA (+) epithelial cells can be diagnosed as COVID-19.

Example 10

ISIM Sars-Cov-2 Specific Antibody Staining of Nasopharyngeal Epithelial Cells to Diagnose COVID-19

Sampling and Staining:

Mix nasopharyngeal cytology swab with staining solution, for example, including PBS, Zwittgent 3-14, ethanol, and AF488-anti-Spike or AF488-anti-Nucleocapsid protein antibody;

Close the Q-Card and incubate the specimen sample with the staining solution (in some embodiments at room temperature for less than 1 min); and Image, record, and analyze, the nasopharyngeal epithelial cells in the closed Q-Card using an iPhone having an adapter or a fluorescent microscope.

Experimental Results: Observation of AF488-anti-Spike (+) or AF488-anti-Nucelocapsid protein (+) epithelial cells can be diagnosed as COVID-19.

Biomarkers

Tables 1 to 3 provide lists of biomarkers that can be detected in accordance with the present invention and their associated diseases or conditions.

A biomarker, as listed in the accompanying tables, can be for example, a protein or a nucleic acid (e.g., mRNA) biomarker, unless specified otherwise. The diagnosis can be associated with an increase or a decrease in the level of a biomarker in the sample, unless specified otherwise.

TABLE 1

Diagnostic Markers

| Marker (bodily fluid source) | Disease |
|---|---|
| Aβ42, amyloid beta-protein (cerebral spinal fluid; CSF) | Alzheimer's disease (AD). |
| fetuin-A (CSF) | multiple sclerosis. |
| tau (CSF) | niemann-pick type C. |
| secretogranin II (CSF) | bipolar disorder. |
| prion protein (CSF) | Alzheimer disease, prion disease |
| Cytokines (CSF) | HIV-associated neurocognitive disorders |
| Alpha-synuclein (CSF) | parkinsonian disorders (neuordegenerative disorders) |
| tau protein (CSF) | parkinsonian disorders |
| neurofilament light chain (CSF) | axonal degeneration |
| parkin (CSF) | neuordegenerative disorders |

TABLE 1-continued

| Diagnostic Markers | |
|---|---|
| Marker (bodily fluid source) | Disease |
| PTEN induced putative kinase 1 (CSF) | neuordegenerative disorders |
| DJ-1 (CSF) | neuordegenerative disorders |
| leucine-rich repeat kinase 2 (CSF) | neuordegenerative disorders |
| mutated ATP13A2 (CSF) | Kufor-Rakeb disease |
| Apo H (CSF) | parkinson disease (PD) |
| ceruloplasmin (CSF) | PD |
| Peroxisome proliferator-activated receptor gamma coactivator-1 alpha (PGC-1α)(CSF) | PD |
| transthyretin (CSF) | CSF rhinorrhea (nasal surgery samples) |
| Vitamin D-binding Protein (CSF) | Multiple Sclerosis Progression |
| proapoptotic kinase R (PKR) and its phosphorylated PKR (pPKR) (CSF) | AD |
| CXCL13 (CSF) | multiple sclerosis |
| IL-12p40, CXCL13 and IL-8 (CSF) | intrathecal inflammation |
| Dkk-3 (semen) | prostate cancer |
| p14 endocan fragment (blood) | Sepsis: Endocan, specifically secreted by activated-pulmonary vascular endothelial cells, is thought to play a key role in the control of the lung inflammatory reaction. |
| Serum (blood) | neuromyelitis optica |
| ACE2 (blood) | cardiovascular disease |
| autoantibody to CD25 (blood) | early diagnosis of esophageal squamous cell carcinoma |
| hTERT (blood) | lung cancer |
| CAI25 (MUC 16) (blood) | lung cancer |
| VEGF (blood) | lung cancer |
| sIL-2 (blood) | lung cancer |
| Osteopontin (blood) | lung cancer |
| Human epididymis protein 4 (HE4) (blood) | ovarian cancer |
| Alpha-Fetal Protein (blood) | pregnancy |
| Albumin (urine) | diabetics |
| albumin (urine) uria | albuminuria |
| microalbuminuria | kidney leaks |
| AFP (urine) | mirror fetal AFP levels |
| neutrophil gelatinase-associated lipocalin (NGAL) (urine) | Acute kidney injury |
| interleukin 18 (IL-18) (urine) | Acute kidney injury |
| Kidney Injury Molecule-1 (KIM-1) (urine) | Acute kidney injury |
| Liver Fatty Acid Binding Protein (L-FABP) (urine) | Acute kidney injury |
| LMP1 (saliva) | Epstein-Barr virus oncoprotein (nasopharyngeal carcinomas) |
| BARF1 (saliva) | Epstein-Barr virus oncoprotein (nasopharyngeal carcinomas) |
| IL-8 (saliva) | oral cancer biomarker |
| carcinoembryonic antigen (CEA) (saliva) | oral or salivary malignant tumors |
| BRAF, CCNI, EGRF, FGF19, FRS2, GREB1, and LZTS1 (saliva) | Lung cancer |
| alpha-amylase (saliva) | cardiovascular disease |
| carcinoembryonic antigen (saliva) | Malignant tumors of the oral cavity |
| CA 125 (saliva) | Ovarian cancer |
| IL8 (saliva) | spinalcellular carcinoma. |
| thioredoxin (saliva) | spinalcellular carcinoma. |
| beta-2 microglobulin levels - monitor activity of the virus (saliva) | HIV |
| tumor necrosis factor-alpha receptors - monitor activity of the virus (saliva) | HIV |
| CA15-3 (saliva) | breast cancer |

TABLE 2

| Diagnostic Markers | | |
|---|---|---|
| Disease/Condition | Source | Biomarker |
| HPA axis activity (Cushing's disease, Adrenal cortex diseases, etc.) | Saliva | Cortisol |

TABLE 2-continued

Diagnostic Markers

| Disease/Condition | Source | Biomarker |
|---|---|---|
| Pregnancy/fetal development | Saliva | progesterone |
| | urine | human chorionic gonadotropin, Levonorgestrel, alpha-fetoprotein, early conception factor, Unconjugated Estriol |
| | serum | Estradiol, interleukin-6, Unconjugated Estriol, Inhibin-A |
| Infant development | urine | NGAL, KIM-1, Cys-C, and B2mG, AFP S100B, MBP |
| Menopause | Saliva | Follicle stimulating hormone (FSH) Estrogen and progesterone, testosterone, free testosterone, and dehydroepiandrosterone sulfate (DHEAS), cortisol and dehydroepiandrosterone (DHEA) |
| Polycystic ovary syndrome | saliva | testosterone |
| Andropause | saliva | testosterone; testosterone precursors such as pregnenolone, progesterone, 17-hydroxypregnenolone, 17-hydroxyprogesterone, dehydroepiandrosterone (DHEA) and delta-4-androstene-3,17-dione; testosterone and dihydrotestosterone metabolites such as the 17-ketosteroids androsterone and etiocholanolone, polar metabolites in the form of diols, triols, and conjugates, as well estradiol, estrogens, androsteindione, cortisol, DHEA, FSH (follicle stimulating hormone), LH (luteinizing hormone), and GnRH (gonadotropin-releasing hormone) |
| Coagulation status/disorders | miscellaneous | b-Thromboglobulin, Platelet factor 4, Von Willebrand factor, Factor I: Fibrinogen, Factor II: Prothrombin, Factor III: Tissue factor, Factor IV: Calcium, Factor V: Proaccelerin, Factor VI, Factor VII: Proconvertin, Factor VIII:, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1) |
| Autism | miscellaneous | miR-484, miR-21, miR-212, miR-23a, miR-598, miR-95, miR-129, miR-431, miR-7, miR-15a, miR-27a, miR-15b, miR-148b, miR-132, or miR-128; miR-93, miR-106a, miR-539, miR-652, miR-550, miR-432, miR-193b, miR-181d, miR-146b, miR-140, miR-381, miR-320a, or miR-106b; GM1, GD1a, GD1b, or GT1b Ceruloplasmin, Metalothioneine, Zinc, Copper, B6, B12, Glutathione, Alkaline phosphatase, and Activation of apo-alkaline phosphatases |
| Alzheimer's Disease | miscellaneous | miR-107, miR-29a, miR-29b-1, or miR-9; miR-128; HIF-1α, BACE1, Reelin, CHRNA7, or 3Rtau/4Rtau; BACE1, Reelin, Cystatin C, Truncated Cystatin C, Amyloid Beta, C3a, t-Tau, Complement factor H, or alpha-2-macroglobulin |
| | CSF, serum, saliva | β-amyloid(1-42), β-amyloid(1-40), tau, phosphor-tau-181 |
| | Saliva | cTnl, myoglobin, MMP-9, MMP-8, MMP-2, sICAM-1, myeloperoxidase [MPO], IL-4, and/or IL-5; B-type natiuretic peptide [BNP], IL-1α, IL-11, IL-10, TNF-α, IFN-γ, VEGF, insulin, GLP-1 (active), GLP-1 (total), TREM1, Leukotriene E4, Akt1, Aβ-40, Aβ-42, Fas ligand, PSA, G-CSF, MIP-1α, IL-22, IL-8, IL-21, IL-15, IL-6, IL-7, GM-CSF, IL-2, IL-12, IL-17α, IL-1β, MCP, IL-32 or RANTES, apolipoproteins A1, D and E, ischemia-modified albumin (IMA), fibronectin, s. alpha-amylase, aspartate aminotransferase, lactate dehydrogenase, tissue factor activity, MCP-1, sVCAM-1, sCD-40, insulin-like growth factor I (IGF-I), IGF-II acetylcholinesterase enzyme (AChE), |

TABLE 2-continued

| Diagnostic Markers | | |
|---|---|---|
| Disease/Condition | Source | Biomarker |
| | Serum/CSF | β-amyloid(1-42), β-amyloid(1-40), tau, phosphor-tau-181, GSK-3, PKC, VCAM-1 and ICAM-1, macrophage inflammatory proteins-1δ and -4 (MIP1δ and MIP4), regulated upon activation normal T-cell (RANTES), tumor necrosis factor-alpha (TNFα), midregional pro-atrial natriuretic peptide (MR-proANP) AD-associated neuronal thread protein (AD7c-NTP) |
| Parkinson's Disease | miscellaneous | miR-133b; Nurr1, BDNF, TrkB, gstm1, or 5100 beta; apo-H, Ceruloplasmin, BDNF, IL-8, Beta2-microglobulin, apoAll, tau, ABeta1-42, DJ-1 |
| | Saliva | cTnl, myoglobin, MMP-9, MMP-8, MMP-2, SICAM-1, myeloperoxidase [MPO], IL-4, and/or IL-5; B-type natiuretic peptide [BNP], IL-1α, IL-11, IL-10, TNF-α, IFN-γ, VEGF, insulin, GLP-1 (active), GLP-1 (total), TREM1, Leukotriene E4, Akt1, Aβ-40, Aβ-42, Fas ligand, PSA, G-CSF, MIP-1α, IL-22, IL-8, IL-21, IL-15, IL-6, IL-7, GM-CSF, IL-2, IL-12, IL-17α, IL-1β, MCP, IL-32 or RANTES, apolipoproteins A1, D and E, ischemia-modified albumin (IMA), fibronectin, s. alpha-amylase, aspartate aminotransferase, lactate dehydrogenase, tissue factor activity, MCP-1, sVCAM-1, sCD-40, insulin-like growth factor I (IGF-I), IGF-II |
| Schizophrenia | miscellaneous | miR-181b; miR-7, miR-24, miR-26b, miR-29b, miR-30b, miR-30e, miR-92, or miR-195; IFITM3, SERPINA3, GLS, or ALDH7A1BASP1; TP5B, ATP5H, ATP6V1B, DNM1, NDUFV2, NSF, PDHB |
| Bipolar disease | miscellaneous | FGF2, ALDH7A1, AGXT2L1, AQP4, or PCNT2 |
| Mood disorder | (blood) | Mbp, Edg2, Fgfr1, Fzd3, Mag, Pmp22, Ugt8, Erbb3, Igfbp4, Igfbp6, Pde6d, Ptprm, Nefh, Atp2c1, Atxn1, Btg1, C6orf182, Dicer1, Dnajc6, and Ednrb |
| Major Depressive Disorder | miscellaneous | FGFR1, FGFR2, FGFR3, or AQP4 Secretogranin, VGF |
| | serum | Cortisol; EGF; GCS; PPY; ACTH; AVP; CRH; A1AT; A2M; ApoC3; CD40L; IL-6; IL-13; IL-18; IL-1ra; MPO; PAI-1; TNFA; ACRP30; ASP; FABP; INS; LEP; PRL; RETN; Testosterone; TSH; BDNF; S100B; NTF3; GDNF; ARTN |
| Prion disease | miscellaneous | Amyloid B4, App, IL-1R1, or SOD1; PrP(c), 14-3-3, NSE, S-100, Tau, AQP-4 |
| Inflammation | miscellaneous | TNF-α, IL-6, IL1β, Rheumatoid factor (RF), Antinuclear Antibody (ANA), acute phase markers including C-reactive protein (CRP), Clara Cell Protein (Uteroglobin) |
| Multiple sclerosis | miscellaneous | 14-3-3 protein epsilon; Isoform Long of Protocadherin alpha C2 precursor; Insulin-like growth factor IA precursor; Isoform 1 of Protocadherin-8 precursor; Isoform 1 of Sodium/potassium/calcium exchanger 2 precursor; Complement factor H-related 5; Di-N-acetylchitobiase precursor; Isoform 1 of Protein NDRG2; N-acetylglucosamine-6-sulfatase precursor; Isoform 1 of Semaphorin-3B precursor; Cadherin-5 precursor; UPF0454 protein C12orf49 precursor; Dihydrolipoyl dehydrogenase, mitochondrial precursor; Metallothionein-3; Fas apoptotic inhibitory molecule 2; Coactosin-like protein; Isoform Long of Platelet-derived growth factor A chain Precursor; Isoform Long of Endothelin-3 precursor; HLA class I histocompatibility antigen, A-1 alpha chain Precursor; Neuronal pentraxin-2 precursor; retbindin isoform 2; Neuroendocrine convertase 2 precursor; 15 kDa selenoprotein isoform 1 precursor; Phospholipase D4; Isoform 1 of CD109 antigen precursor; Ectonucleotide pyrophosphatase/phosphodiesterase family; member 6 precursor; Fascin; Golgi phosphoprotein 2; Isoform Delta 6 of Calcium/calmodulin-dependent protein kinase type II delta chain; Isoform 1 of FRAS1-related extracellular matrix protein 2 Precursor; Putative uncharacterized protein LOC130576; Isoform 1 of L-lactate dehydrogenase A chain; Isoform 1 of |

TABLE 2-continued

| Diagnostic Markers | | |
|---|---|---|
| Disease/Condition | Source | Biomarker |
| | | Polypeptide N-acetylgalactosaminyltransferase 13; Papilin; Protein DJ-1; Beta-mannosidase precursor; Protein YIPF3; Isoform 1 of Receptor-type tyrosine-protein phosphatase N2 Precursor; Cell growth regulator with EF hand domain protein 1; Sulfhydryl oxidase 2 precursor; Ig lambda chain V-II region TRO; Ig lambda chain V-VI region AR; Ig heavy chain V-III region WEA; Ig heavy chain V-III region CAM; Ig heavy chain V-III region BUR; Myosin-reactive immunoglobulin kappa chain variable region (Fragment); Microfibrillar protein 2 (Fragment); Ig kappa chain V-III region IARC/BL41 precursor; Ig kappa chain V-I region Kue; Ig kappa chain V-I region Scw; Ig kappa chain V-III region B6; IGLV6-57 protein; hypothetical protein LOC402665; Isoform 1 of Proline-rich acidic protein 1 precursor; Rheumatoid factor RF-ET13; Rheumatoid factor D5 heavy chain (Fragment); Uncharacterized protein ENSP00000375027; Uncharacterized protein ENSP00000375043; Uncharacterized protein ENSP00000375019; Isoform 1 of Protocadherin-1 precursor; Isoform 1 of Epithelial discoidin domain-containing receptor 1 precursor; Serine protease HTRA1 precursor; Isoform Delta of Poliovirus receptor-related protein 1 Precursor; chemokine (C—X—C motif) ligand 16; Plastin-2; 14-3-3 protein zeta/delta; Apolipoprotein C-II precursor; Brain-specific angiogenesis inhibitor 1 precursor; Semaphorin-3G precursor; Follistatin-related protein 3 precursor; Hepatocyte growth factor activator precursor; Isoform 1 of Contactin-associated protein-like 2 precursor; Phosphoglycerate kinase 1; Gamma-enolase; Phosphoglycerate mutase 2; Low affinity immunoglobulin gamma Fc region receptor III-A precursor; Isoform Beta of Poliovirus receptor precursor; Serine protease inhibitor Kazal-type 6 precursor; Isoform 1 of Chordin precursor; Out at first protein homolog precursor; Isoform 1 of Carboxypeptidase B2 precursor; ROBO2 isoform a Ig kappa chain V-III region POM; Isoform 1 of Protein-L-isoaspartate(D-aspartate) O-Methyltransferase CDNA FLJ45296 fis, clone BRHIP3003340, moderately similar to Actin, alpha skeletal muscle 2; Isoform 1 of RGM domain family member B precursor; Carboxypeptidase N subunit 2 precursor; Hypothetical LOC284297 |
| | miscellaneous | L-6, IL-17, PAR-3, IL-17, T1/ST2, JunD, 5-LO, LTA4H, MBP, PLP, or alpha-beta crystallin antithrombin III; α-2 glycoprotein 1, zinc; transthyretin (prealbumin); NADH dehydrogenase (ubiquinone) 1 beta subcomplex, 2; neurotrimin; orosomucoid 1 precursor (α-1-acid glycoprotein-1); leucine-rich α-2-glycoprotein; leucine-rich repeat protein; α-1-antitrypsin |
| Chronique fatigue syndrome | saliva | cortisol |
| | saliva | Ig alpha-1 chain C region; Polymeric immunoglobulin receptor; Protein S100-A7; Cystatin-C; Cystatin-B; 14-3-3 protein zeta/delta; Zinc-alpha-2-glycoprotein (ZAG) |
| Sjogren's | saliva | IgA, IgG, IgM autoantibodies; IgA, lactoferrin and beta2-microglobulin; lysozyme C, and cystatin C, amylase and carbonic anhydrase |
| syndrome | miscellaneous | Autoantibodies (SSA/Ro; LA/SS-B) |
| Systemic lupus erythematosus (SLE) | miscellaneous | Autoantibodies (CDC25B, APOBEC3G, ARAF, BCL2A1, CLK1, CREB1, CSNK1G1, CSNK2A1, CWC27, DLX4, DPPA2, EFHD2, EGR2, ERCC2, EWSR1, EZH2, FES, FOS, FTHL17, GEM, GNA15, GNG4, HMGB2, HNRNPUL1, HOXB6, ID2, IFI35, IGF2BP3, IGHG1, JUNB, KLF6, LGALS7, LIN28A, MLLT3, NFIL3, NRBF2, PABPC1, PATZ1, PCGF2, PPP2CB, PPP3CC, PRM1, PTK2, PTPN4, PYGB, RET, RPL18A, RPS7, RRAS, SCEL, SH2B1, SMAD2, STAM, TAF9, TIE1, UBA3, VAV1, WT1, ZAP70, or ZNRD1) |

TABLE 2-continued

| Diagnostic Markers | | |
|---|---|---|
| Disease/Condition | Source | Biomarker |
| | miscellaneous | Autoantibodies ((i) KIT, (ii) C6orf93, (iii) RPL34, (iv) DOM3Z, (v) COPG2, (vi) DNCL12, (vii) RRP41, (viii) FBXO9, (ix) RALBP1, (x) PIAS2, (xi) EEF1D, (xii) CONI, (xiii) KATNB1, (xiv) POLR2E, (xv) CCT3, (xvi) KIAA0643, (xvii) RPL37A, (xviii) GTF2H2, (xix) MAP2K5, (xx) CDK3, (xxi) RPS6KA1, (xxii) MARK4, (xxiii) MTO1, (xxiv) MGC42105, (XXV) NFE2L2, (xxvi) WDR45L, (xxvii) STK4, (xxviii) PFKFB3, (xxix) NTRK3, (xxx) MLF1, (xxXi) TRIM37, (xxxii) ACTL7B, (xxxiii) RPL18A, (xxxiv) CKS1B, (XXXV) TUBA1, (xxxVi) NME6, (xxxvii) SUCLA2, (xxxviii) IGHG1, (xxxix) PRKCBP1, (xl) BAG3, (xli) TCEB3, (xlii) RPL15, (xliii) SSX4, (xliv) MAP2K7, (xlv) EEF1G, (xlvi) RNF38, (xlvii) PHLDA2, (xlviii) KCMF1, (xlix) NUBP2, (I) VPS45A) |
| | miscellaneous | Autoantibodies (SSA/Ro; dsDNA; Smith; histones; thrombin) |
| CREST syndrome | | Autoantibodies (centromere) |
| Systemic sclerosis | miscellaneous | Autoantibodies (Type I topoisomerase) |
| Primary biliary cirrhosis | miscellaneous | Autoantibodies (nucleoporin 62, Sp100 nuclear antigen, nucleoporin 210 kDa, mitochondria) |
| cirrhosis | miscellaneous | NLT; NLT, HBSAG, AST, YKL-40, Hyaluronic acid, TIMP-1, alpha 2 macroglobulin, a-1-antitrypsin P1Z allele, haptoglobin, or acid phosphatase ACP AC |
| autoimmune hepatitis | miscellaneous | Autoantibodies (Liver kidney microsomal type 1, smooth muscle) |
| Celiac disease | miscellaneous | Autoantibodies (tTG, actin) |
| Celiac disease | saliva | Anti-IgA gliadin |
| Irritable Bowel Syndrome (IBS) | miscellaneous | REG1A, MMP3 |
| Inflammatory bowel disease (IBD) | miscellaneous | Trypsinogen IV, SERT; II-16, II-1beta, II-12, TNF-alpha, interferon gamma, 11-6, Rantes, MCP-1, Resistin, or 5-HT |
| Ulcerative colitis | miscellaneous | IFITM1, IFITM3, STAT1, STAT3, TAP1, PSME2, PSMB8, HNF4G, KLF5, AQP8, APT2B1, SLC16A, MFAP4, CCNG2, SLC44A4, DDAH1, TOB1, 231152_at, MKNK1, CEACAM7*, 1562836_at, CDC42SE2, PSD3, 231169_at, IGL@*, GSN, GPM6B, CDV3*, PDPK1, ANP32E, ADAM9, CDH1, NLRP2, 215777_at, OSBPL1, VNN1, RABGAP1L, PHACTR2, ASH1L, 213710_s_at, CDH1, NLRP2, 215777_at, OSBPL1, VNN1, RABGAP1L, PHACTR2, ASH1, 213710_s_at, ZNF3, FUT2, IGHA1, EDEM1, GPR171, 229713_at, LOC643187, FLVCR1, SNAP23*, ETNK1, LOC728411, POSTN, MUC12, HOXA5, SIGLEC1, LARP5, PIGR, SPTBN1, UFM1, C6orf62, WDR90, ALDH1A3, F2RL1, IGHV1-69, DUOX2, RAB5A, or CP; (P)ASCA |
| Hyperplastic Polyp | miscellaneous | SLC6A14, ARHGEF10, ALS2, IL1RN, SPRy4, PTGER3, TRIM29, SERPINB5, 1560327 at, ZAK, BAG4, TRIB3, TTL, FOXQ1 |
| Psoriasis | miscellaneous | miR-146b, miR-20a, miR-146a, miR-31, miR-200a, miR-17-5p, miR-30e-5p, miR-141, miR-203, miR-142-3p, miR-21, or miR-106a; miR-125b, miR-99b, miR-122a, miR-197, miR-100, miR-381, miR-518b, miR-524, let-7e, miR-30c, miR-365, miR-133b, miR-10a, miR-133a, miR-22, miR-326, or miR-215; IL-20, VEGFR-1, VEGFR-2, VEGFR-3, or EGR1; |
| Dermatitis herpetiformis | miscellaneous | Autoantibodies (eTG) |
| Miller-Fisher Syndrome | miscellaneous | Autoantibodies (ganglioside GQ1B) |

TABLE 2-continued

| Diagnostic Markers | | |
|---|---|---|
| Disease/Condition | Source | Biomarker |
| Wegener's granulomatosis | miscellaneous | Autoantibodies (c-ANCA) |
| Neuropathies | miscellaneous | Autoantibodies (ganglioside GD3, ganglioside GM1) |
| microscopic polyangiitis | miscellaneous | Autoantibodies (p-ANCA) |
| Polymyositis | miscellaneous | Autoantibodies (Signal recognition particles) |
| scleromyositis | miscellaneous | Autoantibodies (exosome complex Signal recognition particles) |
| myasthenia gravis | miscellaneous | Autoantibodies (nicotinic acetylcholine receptor Signal recognition particles, muscle-specific kinase (MUSK) Signal recognition particles) |
| Lambert-Eaton myasthenic syndrome | miscellaneous | Autoantibodies (voltage-gated calcium channel (P/Q-type)) |
| Hashimoto's thyroiditis | miscellaneous | Autoantibodies (thyroid peroxidase) |
| Graves' disease | miscellaneous | Autoantibodies (TSH receptor) |
| paraneoplastic cerebellar syndrome | miscellaneous | Autoantibodies (Hu, Yo (cerebellar Purkinje Cells), amphiphysin) |
| encephalitis | miscellaneous | Autoantibodies (voltage-gated potassium channel (VGKC), N-methyl-D-aspartate receptor (NMDA)) |
| Sydenham's chorea | miscellaneous | Autoantibodies (basal ganglia neurons) |
| Neuromyelitis | miscellaneous | Autoantibodies (aquaporin-4) |
| Allergies | saliva | Allergen-specific IgAs |
| Rheumatic disease | miscellaneous | miR-146a, miR-155, miR-132, miR-16, or miR-181; HOXD10, HOXD11, HOXD13, CCL8, LIM homeobox2, or CENP-E; TNFα |
| Rheumatoid arthritis | miscellaneous | Autoantibodies (Rheumatoid factor, cyclic citrullinated protein) |
| Rheumatoid arthritis | miscellaneous | ATP-binding cassette, sub-family A, member 12 isoform b; ATP-binding cassette A12; apolipoprotein; B-100 precursor - human; complement component 3 precursor; alpha-2-glycoprotein 1,zinc; Alpha-2-glycoprotein, zinc; serine (or cysteine) proteinase inhibitor, clade A (alpha-1 antiproteinase, antitrypsin), member 2; Protease inhibitor 1-like; protease inhibitor 1 (alpha-1-antitrypsin)-like; group-specific component (vitamin D binding protein); hDBP; serine (or cysteine) proteinase inhibitor, clade A (alpha-1 antiproteinase, antitrypsin), member 1; Protease inhibitor (alpha-1-antitrypsin); protease inhibitor 1 (anti-elastase), alpha-1-antitrypsin; Vitronectin precursor V65 subunit; A kinase anchor protein 9 isoform 2; retrovirus-related hypothetical protein II -human retrotransposon LINE-1; nuclear receptor coactivator RAP250; peroxisome proliferator-act; nuclear receptor coactivator RAP2; Ig kappa chain NIG26 precursor - human; Vitamin D-binding protein precursor (DBF)(Group-specific component)(GC-globulin)(VDB) complement C4A precursor [validated] Human; guanine nucleotide binding protein (G protein), gamma transducing activity polypeptide 1; nucleoporin 98 kD isoform 4; nucleoporin 98 kD; Nup98-Nup96 precursor; GLFG-repeat containing; nucleoporin; vitronectin precursor; serum spreading factor; somatomedin B; complement S-protein; Alpha-1-antitrypsin precursor; HMG-BOX transcription; factor BBX; x 001; protein; hect domain and RLD 2; calcium channel, voltage-dependent, L |

TABLE 2-continued

| Diagnostic Markers | | |
|---|---|---|
| Disease/Condition | Source | Biomarker |
| | | type, alpha 1C subunit; Alpha-2-antiplasmin precursor (Alpha-2-plasmin inhibitor)(Alpha-2-PI)(Alpha-2-AP); Neuronal PAS domain protein 2 (Neuronal PAS2) (Member of PAS protein 4)(MOP4); Retinoic acid receptor gamma-2 (RAR-gamma-2) alpha-1-B-glycoprotein - human; Heparin cofactor II precursor (HC-II)(Protease inhibitor leuserpin 2)(HLS2); lg gamma-1 chain C region; isocitrate dehydrogenase 3 (NAD+) alpha precursor; H-IDH alpha; isocitric dehydrogenase; isocitrate dehydrogenase [NAD] sub-unit alpha, mitochondrial; NAD+-specific ICDH; NAD(H)-specific isocitrate dehydrogenase alpha subunit precursor; isocitrate dehydrogenase (NAD+) alpha chain precursor; ferroxidase (EC 1.16.3.1) precursor [validated] - human; similar to zona pellucida binding protein; N-acetylneuraminic acid phosphate synthase; sialic acid synthase; sialic acid phosphate synthase; triple functional domain (PTPRF interacting); deleted in bladder cancer chromosome region candidate 1; ceruloplasmin (ferroxidase); Ceruloplasmin; RAB3A interacting protein (rabin3)-like 1; talin 2; similar to Ceruloplasmin precursor (Ferroxidase); orosomucoid 1 precursor; Orosomucoid-1 (alpha-1-acid glycoprotein-1); Ig lambda chain precursor - human; cold autoinflammatory syndrome 1; chromosome 1 open reading frame 7; angio-tensin/vasopressin receptor; similar to KIAA0913 protein; sodium channel, voltage-gated, type V, alpha polypeptide; hypothetical protein FLJ10379; orosomucoid 2; alpha-1-acid glycoprotein, type 2; Ig alpha-1 chain C region; corticosteroid binding globulin precursor; corticosteroid binding globulin; alpha-1 anti-proteinase, antitrypsin; KV3M_HUMAN IG KAPPA CHAIN V-III REGION HIC PRECURSOR; MUC_HUMAN Ig mu chain C region; similar to Ig gamma-2 chain C region; alpha-1-antichymotrypsin, precursor; alpha-1-antichymotrypsin; Antichymotrypsin; thyroid hormone receptor-associated protein, 240 kDa subunit; Ig heavy chain - human; Alpha-1-antichymotrypsin precursor (ACT) hypothetical protein XP_173158; hypothetical protein DKFZp434G2226; haptoglobin; Plasma protease C1 inhibitor precursor (C1 Inh)(C1Inh) Haptoglobin-1 precursor; leucine-rich alpha-2-glycoprotein; S-arrestin; S-antigen; NAD(P)H dehydrogenase, quinone 2; NAD(P)H menadione oxidoreductase-1, di-oxin-inducible-2; NAD(P)H menadione oxi-doreductase 2, dioxin-inducible; angiotensin precursor [validated] - human; similar to KIAA1902 protein; similar to KIAA1728 protein; calpain 3 isoform d; calpain, large polypep- tide L3; calpain p94, large [catalytic] subunit; muscle-specific calcium-activated neutral protease 3 large subunit; asp (abnormal spindle)-like, microcephaly associated; haptoglobin-related protein; Haptoglobin-related locus; Ig alpha-2 chain C region; hypothetical protein DKFZp434P1818.1 - human (fragment); GC3_HUMAN Ig gamma-3 chain C region (Heavy chain disease protein)(HDC) |
| Organ Rejection | miscellaneous | miR-658, miR-125a, miR-320, miR-381, miR-628, miR-602, miR-629, or miR-125a; miR-324-3p, miR-611, miR-654, miR-330_MM1, miR-524, miR-17-3p_MM1, miR-483, miR-663, miR-5,6-5p, miR-326, miR-197_MM2, or miR-346; matix metalloprotein-9, proteinase 3, or HNP |
| Bone turnover/ Osteoporosis | Urine | Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b |
| | saliva | deoxypyridinium (D-PYR) and osteocalcin (OC), hepatocyte growth factor and interleukin-1 beta |
| | Serum | Osteocalcin, alkaline phosphatase, bone-specific alkaline phosphatase, serum type 1 procollagen (C1NP, P1NP) |

TABLE 2-continued

| Diagnostic Markers | | |
|---|---|---|
| Disease/Condition | Source | Biomarker |
| Jaw osteonecrosis | miscellaneous | PTH, insulin, TNF-α, leptin, OPN, OC, OPG and IL6 |
| Gaucher's disease | (serum)<br>urine | lyso-Gb1, Chitotriosidase and CCL18<br>CCL18 |
| Traumatic brain injury | Miscellaneous<br>urine<br>serum | apoA-1, S-100B, isoprostane<br>GFAP, NGAL<br>neuron-specific enolase (NSE) |
| Septic shock | Miscellaneous | 15-Hydroxy-PG dehydrogenase (up), LAIR1 (up), NFKB1A (up), TLR2, PGLYPR1, TLR4, MD2, TLR5, IFNAR2, IRAK2, IRAK3, IRAK4, PI3K, PI3KCB, MAP2K6, MAPK14, NFKB1A, NFKB1, IL1R1, MAP2K1IP1, MKNK1, FAS, CASP4, GADD45B, SOCS3, TNFSF10, TNFSF13B, OSM, HGF, or IL18R1 |
| Septic shock | Miscellaneous | IL-6, Protein-C, IL-1beta |
| Cancer | miscellaneous | FEN-1; CEA, NSE, CA 19-9, CA 125, PSA, proGRP, SCC, NNMT, anti-p53 autoantibodies, Separase and DPPFV/Separase<br>SERPINA3; ACTB; AFM; AGT; AMBP; APOF; APOA2; APOC1; APOE; APOH; SERPINC1; C1QB; C3; C4BPA; C8G; C9; SERPINA6; CD14; CP; CRP; CSK; F9; FGA; FGG; FLNA; FN1; GC; HRG; IF; IGFALS; ITGA1; ITIH1; ITIH2; ITIH4; KLKB1; LPA; MLL; MRC1; MYL2; MYO6; ORM1; SERPINF1; SERPINA1; SERPINA4; PROS1; QSCN6; RGS4; SAA4; SERPINA7; TF; TFRC; TTN; UBC; ALMS1; ATRN; PDCD11; KIAA0433; SERPINA10; BCOR; C10orf18; YY1AP1; FLJ10006; BDP1; SMARCAD1; MKL2; CHST8; MCPH1; MYO18B; MICAL-L1; PGLYRP2; KCTD7; MGC27165; A1BG; A2M; ABLIM1; ACTA1; AHSG; ANK3; APCS; APOA1; APOA4; APOB; APOC3; APOL1; AZGP1; B2M; BF; C1R; C1S; C2; C4B; C5; C6; C7; C8A; C8B; CDK5RAP2/CDK5RA2; CHGB; CLU; COMP; CORO1A; CPN1; CUL1; DET1; DSC1; F13A1; F2; F5; FGB; GOLGA1; GSN; HBA1; HBB; HP; HPX; HSPA5; HUNK; IGFBP5; IGHG1; IGLV4-3; KIF5C; KNG1; KRT1; KRT10; KRT9; LBP; LGALS3BP; LRG1; LUM; MMP14; MYH4; NEB; NUCB2; ORM2; PF4V1; PIGR; PLG; PON1; PPBP; RBP4; RIMS1; RNF6; SAA1; SEMA3D; SERPIND1; SERPINF2; SERPING1; SF3B1; SPINK1; SPP1; SPTB; SYNE1; TAF4B; TBC1D1; TLN1; TMSB4X; TRIP11; TTR; UROC1; VTN; VWF; ZFHX2; ZYX;<br>PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine; Zinc α2-glycoprotein (ZAG) |
| Adenoma | miscellaneous | SI, DMBT1, CFI*, AQP1, APOD, TNFRSF17, CXCL10, CTSE, IGHA1, SLC9A3, SLC7A1, BATF2, SOCS1, DOCK2, NOS2A, HK2, CXCL2, IL15RA, POU2AF1, CLEC3B, ANI3BP, MGC13057, LCK*, C4BPA, HOXC6, GOLT1A, C2orf32, IL10RA, 240856_at, SOCS3, MEIS3P1, HIPK1, GLS, CPLX1, 236045_x_at, GALC, AMN, CCDC69, CCL28, CPA3, TRIB2, HMGA2, PLCL2, NR3C1, EIF5A, LARP4, RP5-1022P6.2, PHLDB2, FKBP1B, INDO, CLDN8, CNTN3, |

TABLE 2-continued

| Diagnostic Markers | | |
|---|---|---|
| Disease/Condition | Source | Biomarker |
| | | PBEF1, SLC16A9, CDC25B, TPSB2, PBEF1, ID4, GJB5, CHN2, LIMCH1, or CXCL9; ABCA8, KIAA1199, GCG, MAMDC2, C2orf32, 229670_at, IGF1, PCDH7, PRDX6, PCNA, COX2, or MUC6 |
| Head and Neck cancer | saliva | IL-1, IL-6, IL-8, VEGF, MMP-9, TGF-β, TNF-α, MMP-7, plasminogen activated (PA), uPA, IGF, or INF-2 |
| Barrett's esophagus | miscellaneous | miR-21, miR-143, miR-145, miR-194, or miR-215; S100A2, S100A4; p53, MUC1, MUC2 |
| Lung cancer | miscellaneous | miR-21, miR-205, miR-221 (protective), let-7a (protective), miR-137 (risky), miR-372 (risky), or miR-122a (risky); miR-17-92, miR-19a, miR-92, miR-155, miR-191, or miR-210; EGFR, PTEN, RRM1, RRM2, ABCB1, ABCG2, LRP, VEGFR2, VEGFR3, class III b-tubulin; KRAS, hENT1; RLF-MYCL1, TGF-ALK, or CD74-ROS1 |
| | saliva | CCNI, EGFR, FGF19, FRS2, and GREB1 LZTS, BRAF, FRS2, ANXA1, Haptoglobin Hp2, Zinc Alpha2-Glycoprotein, Calprotectin, Porphyromonas catoniae 16S rRNA, Campylobacter showae 16S rRNA, *Streptocococcus salivaris* 16S rRNA, *Campylobacter rectus* 16S rRNA, *Veillonella parvula* 16S rRNA, *Kigella oralis* 16S rRNA, and *Granulicatella adiacens* 16S rRNA |
| Pancreatic cancer | miscellaneous | miR-221, miR-181a, miR-155, miR-210, miR-213, miR-181b, miR-222, miR-181b-2, miR-21, miR-181b-1, miR-220, miR-181d, miR-223, miR-100-1/2, miR-125a, miR-143, miR-10a, miR-146, miR-99, miR-100, miR-199a-1, miR-10b, miR-199a-2, miR-221, miR-181a, miR-155, miR-210, miR-213, miR-181b, miR-222, miR-181b-2, miR-21, miR-181b-1, miR-181c, miR-220, miR-181d, miR-223, miR-100-1/2, miR-125a, miR-143, miR-10a, miR-146, miR-99, miR-100, miR-199a-1, miR-10b, miR-199a-2, miR-107, miR-103, miR-103-2, miR-125b-1, miR-205, miR-23a, miR-221, miR-424, miR-301, miR-100, miR-376a, miR-125b-1, miR-21, miR-16-1, miR-181a, miR-181c, miR-92, miR-15, miR-155, let-7f-1, miR-212, miR-107, miR-024-1/2, miR-18a, miR-31, miR-93, miR-224, or let-7d; miR-148a, miR-148b, miR-375, miR-345, miR-142, miR-133a, miR-216, miR-217 or miR-139; KRAS, CTNNLB1, AKT, NCOA3, or B-RAF; BRCA2, PALB2, or p16 |
| | saliva | MBD3L2, KRAS, STIM2, DMXL2, ACRV1, DMD and CABLES1, TK2, GLTSCR2, CDKL3, TPT1 and DPM1 |
| Breast cancer | miscellaneous | miR-21, miR-155, miR-206, miR-122a, miR-210, miR-155, miR-206, miR-210, or miR-21; let-7, miR-10b, miR-125a, miR-125b, miR-145, miR-143, miR-16, miR-10b, miR-125a; hsp70, MART-1, TRP, HER2, hsp70, MART-1, TRP, HER2, ER, PR, Class III b-tubulin, or VEGFA; GAS5; ETV6-NTRK3 |
| | Saliva | CAH6 (Carbonic anhydrase VI), K2C4 (Cytokeratin 4), CYTA (Cystatin A), FABP4 (Epid. Fatty acid binding prot.), IGHGI (lg gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1 ra (Interleukin-1 receptor anatagonist protein precursor), S10A7 (S100 calcium-binding protein A7), and SPLC2 (Short palate, lung and nasel epith Carc. assoc. protein 2) |
| Ovarian cancer | Saliva | c-erbB-2, cancer antigen 15-3, p53 |
| | urine | HER2/neu (c-erbB-2) |
| | | 47D10 antigen, PTCD2, SLC25A20, NFKB2, RASGRP2, PDE7A, MLL, PRKCE, GPATC3, PRIC285 and GSTA4 |
| | | MIPEP, PLCB2, SLC25A19, DEF6, ZNF236, C18orf22, COX7A2, DDX11, TOP3A, C9orf6, UFC1, PFDN2, KLRD1, LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, |

TABLE 2-continued

| Diagnostic Markers | | |
|---|---|---|
| Disease/Condition | Source | Biomarker |
| | | LOC284184, FLJ23235, GPATC3, CPSF4, CREM, HIST1H1D, HPS4, FN3KRP, ANKRD16, C8 orf16, ATF71P2, PRIC285 |
| | Miscellaneous | miR-200a, miR-141, miR-200c, miR-200b, miR-21, miR-200a, miR-200b, miR-200c, miR-203, miR-205, miR-214, miR-199", or miR-215; miR-199a, miR-140, miR-145, miR-100, miR-let-7 cluster, or miR-125b-1; ERCC1, ER, TOPO1, TOP2A, AR, PTEN, HER2/neu, CD24 or EGFR; VEGFA, VEGFR2, or HER2 |
| Ovarian cancer | Saliva | CA 125 |
| Prostate cancer | Saliva | AGPAT1, B2M, BASP2, IER3, and IL1B |
| | Miscellaneous | miR-9, miR-21, miR-141, miR-370, miR-200b, miR-210, miR-155, or miR-196a; miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-71, miR-188, miR-25, miR-106b, miR-449, miR-99b, miR-93, miR-92-1/2, miR-125a, or miR-141; let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b; miR-15a, miR-16-1, miR-143 or miR-145; AR, PCA3; FASLG or TNFSF10; U50; ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4 kallikrein-2 (KLK2), C reactive protein (CRP), cysteine-rich secretory protein 3 (CRISP3) and chromogranin A (CHGA), comprises prostatic acid phosphatase (PAP), lactate dehydrogenase (LDH), alkaline phosphatase (ALP) |
| | saliva | PSA |
| Esophageal Cancer | urine | PCA3, GOLPH2, SPINK1, TMPRSS2:ERG |
| | miscellaneous | miR-192, miR-194, miR-21, miR-200c, miR-93, miR-342, miR-152, miR-93, miR-25, miR-424, or miR-151; miR-27b, miR-205, miR-203, miR-342, let-7c, miR-125b, miR-100, miR-152, miR-192, miR-194, miR-27b, miR-205, miR-203, miR-200c, miR-99a, miR-29c, miR-140, miR-103, or miR-107; |
| Gastric cancer | miscellaneous | miR-106a, miR-21, miR-191, miR-223, miR-24-1, miR-24-2, miR-107, miR-92-2, miR-214, miR-25, or miR-221; let-7a; RRM2, or surviving; EphA4 |
| Gastrointestinal Stromal Tumor (GIST) | miscellaneous | DOG-1, PKC-theta, KIT, GPR20, PRKCQ, KCNK3, KCNH2, SCG2, TNFRSF6B, or CD34; PDGFRA, c-kit |
| Colorectal carcinoma | miscellaneous | miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p; miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR- |

TABLE 2-continued

Diagnostic Markers

| Disease/Condition | Source | Biomarker |
| --- | --- | --- |
| | | 192, miR-1, miR-34b, miR-215, miR-192, miR-301, miR-324-5p, miR-30a-3p, miR-34c, miR-331, or miR-148b; EFNB1, ERCC1, HER2, VEGF, or EGFR; AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, or TOPO1; GREM1, DDR2, GUCY1A3, TNS1, ADAMTS1, FBLN1, FLJ38028, RDX, FAM129A, ASPN, FRMD6, MCC, RBMS1, SNA12, MEIS1, DOCK10, PLEKHC1, FAM126A, TBC1D9, VWF, DCN, ROBO1, MSRB3, LATS2, MEF2C, IGFBP3, GNB4, RCN3, AKAP12, RFTN1, 226834_at, COL5A1, GNG2, NR3C1*, SPARCL1, MAB21L2, AXIN2, 236894_at, AEBP1, AP1S2, C10orf56, LPHN2, AKT3, FRMD6, COL15A1, CRYAB, COL14A1, LOC286167, QKI, WWTR1, GNG11, PAPPA, or ELDT1; 227458_at, INDO, CXCL9, CCR2, CD38, RARRES3, CXCL10, FAM26F, TNIP3, NOS2A, CCRL1, TLR8, IL18BP, FCRL5, SAMD9L, ECGF1, TNFSF13B, GBPS, or GBP1; TMEM37*, IL33, CA4, CCDC58, CLIC6, VERSUSNL1, ESPN, APCDD1, C13orf18, CYP4X1, ATP2A3, LOC646627, MUPCDH, ANPEP, C1orf115, HSD3B2, GBA3, GABRB2, GYLTL1B, LYZ, SPC25, CDKN2B, FAM89A, MOGAT2, SEMA6D, 229376_at, TSPAN5, IL6R, or SLC26A2 |
| Melanoma | miscellaneous | miR-19a, miR-144, miR-200c, miR-211, miR-324-5p, miR-331, or miR-374; miR-9, miR-15a, miR-17-3p, miR-23b, miR-27a, miR-28, miR-29b, miR-30b, miR-31, miR-34b, miR-34c, miR-95, miR-96, miR-100, miR-104, miR-105, miR-106a, miR-107, miR-122a, miR-124a, miR-125b, miR-127, miR-128a, miR-128b, miR-129, miR-135a, miR-135b, miR-137, miR-138, miR-139, miR-140, miR-141, miR-149, miR-154, miR-154#3, miR-181a, miR-182, miR-183, miR-184, miR-185, miR-189, miR-190, miR-199, miR-199b, miR-200a, miR-200b, miR-204, miR-213, miR-215, miR-216, miR-219, miR-222, miR-224, miR-299, miR-302a, miR-302b, miR-302c, miR-302d, miR-323, miR-325, let-7a, let-7b, let-7d, let-7e, or let-7g; MUM-1, beta-catenin, or Nop/5/Sik; DUSP-1, Alix, hsp70, Gib2, Gia, moesin, GAPDH, malate dehydrogenase, p120 catenin, PGRL, syntaxin-binding protein 1 & 2, septin-2, or WD-repeat containing protein 1; H/ACA (U1071), SNORA11D |
| Head and neck cancer | miscellaneous | miR-21, let-7, miR-18, miR-29c, miR-142-3p, miR-155, miR-146b, miR-205, or miR-21; miR-494; HPV E6, HPV E7, p53, IL-8, SAT, H3FA3; EGFR, EphB4, or EphB2; CHCHD7-PLAG1, CTNNB1-PLAG1, FHIT-HMGA2, HMGA2-NFIB, LIFR-PLAG1, or TCEA1-PLAG1 |
| Oral squamous cell carcinoma | saliva | p53 autoantibodies, defensing-1, IncRNAs (MEG-3, MALAT-1, HOTAIR, NEAT-1, UCA) Cortisol, lactate dehydrogenase, Transferrin, cyclin D1, Maspin, alpha-amylase, IL-8, TNF-α, IL-1, IL-6, Basic fibroblast growth factor, Statherin, Cyfra 21.1, TPA, CA125, Endothelin-1, IL-1β, CD44, IGF-1, MMP-2, MMP-9, CD59, Catalase, Profilin, S100A9/MRP14, M2BP, CEA, Carcinoma associated antigen CA-50, Salivary carbonyls, Maspin, 8-oxoguanine DNA glycosylase, OGG1, Phosphorylated-Src, Ki-67, Zinc finger protein 501 peptide, Hemopexin, Haptoglobin, Complement C3, Transthyretin, α1-antitrypsin, Peroxidase, GST, SOD, 8-OHdG, Glutathione, MDA, miR-125a, miR-200a, miR-31 |
| Salivary gland tumors | miscellaneous | Fibroblast growth factor 2 (FGF2) and fibroblast growth factor receptor 1 (FGFR1) |
| Hepatocellular carcinoma | miscellaneous | miR-221; et-7a-1, let-7a-2, let-7a-3, let-7b, let-7c, let-7d, let-7e, let-7f-2, let-fg, miR-122a, miR-124a-2, miR-130a, miR-132, miR-136, miR-141, miR-142, miR-143, |

TABLE 2-continued

| Diagnostic Markers | | |
|---|---|---|
| Disease/Condition | Source | Biomarker |
| | | miR-145, miR-146, miR-150, miR-155(BIC), miR-181a-1, miR-181a-2, miR-181c, miR-195, miR-199a-1-5p, miR-199a-2-5p, miR-199b, miR-200b, miR-214, miR-223, or pre-miR-594; miR-122, miR-100, or miR-10a; miR-198 or miR-145 |
| Renal cell carcinoma | miscellaneous | miR-141, miR-200; miR-28, miR-185, miR-27, miR-let-7f-2; laminin receptor 1, betaig-h3, Galectin-1, a-2 Macroglobulin, Adipophilin, Angiopoietin 2, Caldesmon 1, Class II MHC-associated invariant chain (CD74), Collagen IV-al, Complement component, Complement component 3, Cytochrome P450, subfamily IIJ polypeptide 2, Delta sleep-inducing peptide, Fc g receptor 111a (CD16), HLA-B, HLA-DRa, HLA-DRb, HLA-SB, IFN-induced transmembrane protein 3, IFN-induced transmembrane protein 1, or Lysyl Oxidase; IF1 alpha, VEGF, PDGFRA; ALPHA-TFEB, NONO-TFE3, PRCC-TFE3, SFPQ-TFE3, CLTC-TFE3, or MALAT1-TFEBf |
| Renal cell carcinoma | miscellaneous | Akt, total Erk1/2, total Met, total GSK3b, total Hif1a, total p21, total AMPKa1, total VEGF, total PIGF, total VEGFR-1/FIt-1, phosphorylated Akt, phosphorylated Erk1/2, phosphorylated. Met, phosphorylated STAT3, phosphorylated GSK3b, and phosphorylated AMPKa1 |
| Cervical cancer | miscellaneous | HPV E6, HPV E7, or p53 |
| Thyroid cancer | miscellaneous | AKAP-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET; PAX8-PPARγ |
| Neuroblastoma | Urine | Neuron-specific enolase (NSE) |
| Glioblastoma | serum | GFAP |
| Brain cancer | miscellaneous | miR-21, miR-10b, miR-130a, miR-221, miR-125b-1, miR-125b-2, miR-9-2, miR-21, miR-25, or miR-123; miR-128a, miR-181c, miR-181a, or miR-181b; GOPC-ROS1; MGMT; EGFR |
| Blood Cancers | miscellaneous | HOX11, TAL1, LY1, LMO1, or LMO2; TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, for acute lymphocytic leukemia (ALL); BCL11B-TLX3, IL2-TNFRFS17, NUP214-ABL1, NUP98-CCDC28A, TAL1-STIL, or ETV6-ABL2, for T-cell acute lymphocytic leukemia (T-ALL); ATIC-ALK, KIAA1618-ALK, MSN-ALK, MYH9-ALK, NPM1-ALK, TGF-ALK or TPM3-ALK, for anaplastic large cell lymphoma (ALCL); BCR-ABL1, BCR-JAK2, ETV6-EVI1, ETV6-MN1 or ETV6-TCBA1, for chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, for AML; CCND1-FSTL3, for chronic lymphocytic leukemia (CLL); and FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, for hyper eosinophilia/chronic eosinophilia; miR-23b, miR-24-1, miR-146, miR-155, miR-195, miR-221, miR-331, |

TABLE 2-continued

| Diagnostic Markers | | |
|---|---|---|
| Disease/Condition | Source | Biomarker |
| | | miR-29a, miR-195, miR-34a, or miR-29c; miR-15a, miR-16-1, miR-29 or miR-223; miR-128b, miR-204, miR-218, miR-331, miR-181b-1, miR-17-92 |
| B-Cell Chronic Lymphocytic Leukemia | miscellaneous | miR-183-prec, miR-190, miR-24-1-prec, miR-33, miR-19a, miR-140, miR-123, miR-10b, miR-15b-prec, miR-92-1, miR-188, miR-154, miR-217, miR-101, miR-141-prec, miR-153-prec, miR-196-2, miR-134, miR-141, miR-132, miR-192, or miR-181b-prec; miR-213, miR-220; ZAP70, AdipoR1; BCL3-MYC, MYC-BTG1, BCL7A-MYC, BRWD3-ARHGAP20 or BTG1-MYC |
| B-cell lymphoma | miscellaneous | miR-17-92 polycistron, miR-155, miR-210, or miR-21, miR-19a, miR-92, miR-142 miR-155, miR-221 miR-17-92, miR-21, miR-191, miR-205, U50; miR-17-92, miR-155, miR-210, or miR-21; A-myb, LMO2, JNK3, CD10, bcl-6, Cyclin D2, IRF4, Flip, or CD44; CITTA-BCL6, CLTC-ALK, IL21R-BCL6, PIM1-BCL6, TFCR-BCL6, IKZF1-BCL6 or SEC31A-ALK |
| Burkitt's lymphoma | miscellaneous | pri-miR-155; MYC, TERT, NS, NP, MAZ, RCF3, BYSL, IDE3, CDC7, TCL1A, AUTS2, MYBL1, BMP7, ITPR3, CDC2, BACK2, TTK, MME, ALOX5, or TOP1; BCL6, KI-67; IGH-MYC, LCP1-BCL6 |
| Endometrial cancer | miscellaneous | miR-185, miR-106a, miR-181a, miR-210, miR-423, miR-103, miR-107, or let-7c; miR-71, miR-221, miR-193, miR-152, or miR-30c; NLRP7, AlphaV Beta6 integrin |
| uterine leiomyomas | miscellaneous | let-7 family member, miR-21, miR-23b, miR-29b, or miR-197 |
| myelofibrosis | miscellaneous | miR-190; miR-31, miR-150 and miR-95; miR-34a, miR-342, miR-326, miR-105, miR-149, miR-147 |
| Pheochromocytoma | Urine | Catecholamines (epinephrine, norepinephrine, adrenaline) |
| Kidney disease/injury | miscellaneous | ADBP-26, NHE3, KIM-1, glutamyltransferase, N-acetyl-beta-D-glucosaminidase, lysozyme, NGAL, L-FABP, bikunin, urea, prostaglandins, creatinine, alpha-1-microglobulin, retinol binding protein, glutathione-S-transferases, adiponectin, beta-2-macroglobuin, calbindin-D, cysteine-rich angiogenic inducer 61, endothelial/epithial growth factors, alpha-1-acid glycoprotein (orosomucoid), prealbumin, modified albumin, albumin, transferrin, alpha-1-lipoprotein, alpha-1-antitrypsin matrix metalloproteinases (MMPs), alpha-1-fetoprotein, Tamm Horsfall protein, homoarginine, interleukin 18, monocyte chemotactic protein-1 (MCP-1), Lipocalin, VCAN, NRP1, CCL2, CCL19, COL3A1, GZMM, alpha-galactosidase, casein kinase 2, IP-10, Mig, I-TAC, MIP-1α, MIP-3α, and MIP-1β, alpha-2-glycoprotein-Zinc, leucine-rich alpha-2-glycoprotein, uromodulin, Pacsin 2, hepcidin-20, hepcidin-25, AIF-2, urinary type-IV collagen, lipocalin-type prostaglandin D synthase (L-PGDS), urinary neutrophil gelatinase-associated lipocalin (uNGAL), Annexin A1, Rab23, Shh, Ihh, Dhh, PTCH1, PTCH2, SMO, Gli1, Gli2, Gli3, TLR4, cystatin C, AQPI, AQP2, AQP3, NKCC2, NaPi11, DAHKSEVAHRFKD [RNA:] SLC12A1, UMOD, vWF, MMPI, MMP3, SLC22A6, SLC22A 8, SLC22A 12, podocin, cubulin, LRP2, AQP9, and albumin, carcinoembryonic antigen (CEA), mucin, alpha-fetoprotein, tyrosinase, melanoma associated antigen, mutated tumor protein 53, p21, PUMA, prostate-specific antigen (PSA) or thyroglobulin, von Willebrand factor (VWF), thrombin, factor VIII, plasmin, fibrin, osteopontin (SPP1), Rab23, Shh, Ihh, Dhh, PTCH1, PTCH2, SMO, Gli1, Gli2, Gli3 |
| | urine | L-FABP, NGAL |
| Liver failure/disease | saliva | Lactoferrin, uric acid, cortisol, alpha-amylase |
| | miscellaneous | Carnitine; Cholic Acid; Chenodeoxycholic, Deoxycholic, Lithocholic, Glycocholic; Prostaglandin |

TABLE 2-continued

| Diagnostic Markers | | |
|---|---|---|
| Disease/Condition | Source | Biomarker |
| | | $E_2$; 13, 14-dihydro-15-keto Prostaglandin A2; Prostaglandin B2; Prostaglandin F2a; 15-keto-Prostaglandin F2α; 6-keto-Prostaglandin F1α; Thromboxane B2; 11-dehydro-Thromboxane B2; Prostaglandin D2; Prostaglandin J2; 15-deoxy-Δ12, 14-Prostaglandin J2; 11β-Prostaglandin F2α; 5(S)-Hydroxyeicosatetraenoic acid; 5(S)-Hydroxyeicosapentaenoic acid; Leukotriene B4; Leukotriene B5; Leukotriene C4; Leukotriene D4; Leukotriene E4; Leukotriene F4; 12(S)-Hydroxyeicosatetraenoic acid; 12(S)-Hydroxyeicosapentaenoic acid; 15(S)-Hydroxyeicosatetraenoic acid; 15(S)-Hydroxyeicosapentaenoic acid; Lipoxin A4; 8(S)-Hydroxyeicosatetraenoic acid; 9-Hydroxyeicosatetraenoic acid; 11-Hydroxyeicosatetraenoic acid; 8-iso-Prostaglandin F2α; 9-Hydroxyoctadecadienoic acid; 13-Hydroxyoctadecadienoic acid; 20(S)-Hydroxyeicosatetraenoic acid; 9,10-Epoxyoctadecenoic acid; 12,13-Epoxyoctadecenoic acid; 12,13-Dihydroxyoctadecenoic acid; 5,6-Epoxyeicosatrienoic acid; 11,12-Epoxyeicosatrienoic acid; 14,15-Epoxyeicosatrienoic acid; 5,6-Dihydroxyeicosatrienoic acid; 8,9-Dihydroxyeicosatrienoic acid; 11,12-Dihydroxyeicosatrienoic acid; 14,15-Dihydroxyeicosatrienoic acid; 14,15-Epoxyeicosatetraenoic acid; 17,18-Epoxyeicosatetraenoic acid; 14,15-Dihydroxyeicosatetraenoic acid; 17,18-Dihydroxyeicosatetraenoic acid; 19,20-Dihydroxydocosapentaenoic acid; diacetylspermine, hemopexin, TLR4 |
| Stroke | miscellaneous | MMP9, S100-P, S100A12, SI00A9, coag factor V, Arginasel, CA-IV, monocarboxylic acid transporter, ets-2, EIF2alpha, cytoskeleton associated protein 4, N-formylpeptide receptor, Ribonuclease2, N-acetylneuraminate pyruvate lyase, BCL-6, or Glycogen phosphorylase |
| Heart failure/ Cardiovascular health | urine | 8-iso-prostaglandin F2α (8-iso-PGF2α) |
| | miscellaneous | miR-195, miR-208, miR-214, let-7b, let-7c, let-7e, miR-15b, miR-23a, miR-24, miR-27a, miR-27b, miR-93, miR-99b, miR-100, miR-103, miR-125b, miR-140, miR-145, miR-181a, miR-191, miR-195, miR-199a, miR-320, miR-342, miR-451, or miR-499; miR-1, miR-10a, miR-17-5p, miR-19a, miR-19b, miR-20a, miR-20b, miR-26b, miR-28, miR-30e-5p, miR-101, miR-106a, miR-126, miR-222, miR-374, miR-422b, or miR-423; MRP14, CD69; CK-MB, cTnl (cardiac troponin), CRP, BPN, IL-6, MCSF, CD40, CD40L |
| | miscellaneous | SFRP-3, NT-proBNP, troponin T, SKITHRIHWESASLL (SEQ ID NO: 20), AHKSEVAHRFK (SEQ ID NO: 21), uroguanylin, BNP |
| | saliva | miR-378, miR-497, miR-21, miR-15b, miR-99a, miR 29a, miR-24, miR-30b, miR-29c, miR-331.3p, miR-19a, miR-22, miR-126, let-7b, miR-502.3, and miR-652; IL-16, sFas, Fas ligand, MCP-3, HGF, CTACK, EOTAXIN, adiponectin, IL-18, TIMP.4, TIMP.1, CRP, VEGF, and EGF C-reactive protein (CRP); myoglobin (MYO), creatinine kinase myocardial band (CK-MB), cardiac troponins (cTn), and myeloperoxidase; TNF-a, and MMP-9; CD40 |
| Vulnerable plaque | saliva | Amylase |
| | miscellaneous | L-6, MMP-9, PAPP-A, D-dimer, fibrinogen, Lp-PLA2, SCD40L, II-18, oxLDL, GPx-1, MCP-1, P1GF, or CRP |
| High blood pressure | saliva | lysozyme |
| Fibromyalgia | miscellaneous | NR2D |

TABLE 2-continued

| Diagnostic Markers | | |
|---|---|---|
| Disease/Condition | Source | Biomarker |
| Neuropathic Pain | miscellaneous | CCR2/4, CNP; ICAM-1, CGRP, TIMP-1, CLR-1, HSP-27, FABP, or apolipoprotein D; OX42, ED9 |
| Tiredness/fatigue | saliva | PPGKPQGPPPQGGNQPQGPPPPPGKPQ (SEQ ID NO: 15); GNPQGPSPQGGNKPQGPPPPPGKPQ (SEQ ID NO: 16); SPPGKPQGPPQQEGNKPQGPPPPGKPQ (SEQ ID NO: 17) |
| | urine | endorepellin<br>human herpesvirus 6, human herpesvirus 7, human cytomegalovirus, and Epstein-Barr virus (EBV) |
| | miscellaneous | GGHPPPP (SEQ ID NO: 18), ESPSLIA (SEQ ID NO: 19); |
| Stress | saliva | Cortisol, chromogranin A, alpha-amylase, secretary IgA, lysozyme<br>dehydro-androsteronesulfate; 17-ketosteroidsulfate; dehydro-epiandrostronesulfate; corticosteroid, 17-hydroxycorticosteroid, growth hormone, oxytocin |
| | miscellaneous | aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide |
| Malnutrition | Saliva | slgA |
| Nutritional status | miscellaneous | Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor) |
| Energy balance (protein excretion) / energy status / metabolic state | Serum | AMPK |
| | Urine, sweat, feces | pre-albumin, retinol binding protein, urea |
| | miscellaneous | cholesterol, lipoproteins, insulin, insulin C peptide, IGF binding proteins, e.g. IGF-BPI, liver enzymes |
| Diabetes | Miscellaneous | 11-8, CTSS, ITGB2, HLA-DRA, CD53, PLAG27, or MMP9; RBP4; |
| | Urine | 8-iso-prostaglandin F2a (8-iso-PGF2α), 11-dehydro-thromboxane $B_2$ (TXM) |
| | Urine | C-peptide |
| | Miscellaneous | Advanced glycosylation end products (AGEs), 1,5-anhydroglucitol, NGPTL3 and 4<br>autoantibodies (Zn transporter 8, glutamic acid decarboxylase (GAD)) |
| | Urine (serum, etc.) - miscellaneous | ATP-binding cassette, sub-family C (CFTR/MRP), member 8; ATP-binding cassette, sub-family C (CFTR/MRP), member 9; angiotensin \| converting enzyme (peptidyl-dipeptidase A) 1; adenylate cyclase |

TABLE 2-continued

| Diagnostic Markers | | |
|---|---|---|
| Disease/Condition | Source | Biomarker |
| | | activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like |

TABLE 2-continued

Diagnostic Markers

| Disease/Condition | Source | Biomarker |
|---|---|---|
| | | growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta-melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, |

TABLE 2-continued

| Diagnostic Markers | | |
|---|---|---|
| Disease/Condition | Source | Biomarker |
| | | plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |
| Metabolic syndrome/ prediabetes | Serum | GFAP autoantibodies |
| Alcohol abuse/dependence | saliva | aminotransferases, gamma-glutamyltransferase, ethanol, ethyl glucuronide, sialic acid, β-hexosaminidase A, oral peroxidase, methanol, diethylene/ethylene glycol, α-amylase, clusterin, haptoglobin, heavy/light chains of immunoglobulins and transferrin; α-fucosidase (FUC), a-mannosidase (MAN), β-galactosidase (GAL), and β-glucuronidase (GLU) |

TABLE 2-continued

| Diagnostic Markers | | |
|---|---|---|
| Disease/Condition | Source | Biomarker |
| Non-alcoholic fatty liver disease | miscellaneous | cytokeratin CK-18 (M65 antigen), caspase-cleaved CK-18 (M30-antigen), resistin, adiponectin, visfatin, insulin, tumor necrosis factor-alpha (TNF-α), interleukin 6 (IL-6), or interleukin 8 (IL-8) |
| | Serum | aspartate aminotransferase (AST) and alanine aminotransferase (ALT); gamma-glutamyltransferase (GGT), immunoglobulin A, carbohydrate-deficient transferrin (CDT), glutamic oxaloacetic transaminase (GOT), glutamic pyruvic transaminase (GPT), bilirubin |
| Cystic fibrosis | saliva | amylase<br>cathepsin-D, lactate dehydrogenase |
| Ectodermal dysplasia | saliva | alpha-amylase |
| sarcoidosis | serum | IL-6, TNF-α, IFN-α, IL-17, IP-10, MIG, HGF, VEGF, TNF-RII, G-CSF, IFN-γ, MCP-1, RANTES and IL-5 |
| Asthma | Saliva | eotaxin-1/CCL11, RANTES/CCL5, and IL-5; IL-1β, IL-6, MCP-1/CCL2, and IL-8/CXCL8; IP-10/CXCL10 |
| Periodontitis/dental caries | | aspartate aminotransferase (AST) and alkaline phosphatase (ALP), uric acid and albumin; 12-HETE; MMP-8, TIMP-1, and ICTP |
| Muscle damage | Serum, urine | Myoglobin, creatine kinase (CK), lactate dehydrogenase (LDH), aldolase, troponin, carbonic anhydrase type 3 and fatty acid-binding protein (FABP), transaminases |
| Infection (*Mycobacterium tuberculosis*) | miscellaneous | IL-32, NXNL1, PSMA7, C6orf61, EMP1, CLIC1, LACTB and DUSP3, LOC389541, MIDI IP 1, KLRC3, KLF9, FBXQ32, C50RF29, CHUK, LOC652062, C6ORF60, MTMR II, sCD170; IFN-gamma; IL-Iβ, IL-6, IL-8, IL-10, IL-12p70, sCD4, SCD25, SCD26, sCD32b/c, SCD50, SCD56, sCD66a, SCD83, sCD85j, SCD95, SCD106, sCD120b, sCD121b, SCD127, SCD154, SCD222, SCD226, sCDw329 and TNF alpha; VEGF, AAT, CRP, IL-IRA, TIMP-1, IL- 18, A2Macro, Haptoglobin ICAM-1, VCAM- 1, SCF, IL-17, Fibrinogen, beta-2-macroglobulin, TNF-alpha, C3 and TNFR2, GPR117, TAZ, HSDL I, HIP 1 (host); |
| Infection (*Helicobacter pylori*) | saliva | MUC-5B and MUC 7 |
| Infection (*Candida species*) | saliva | Hsp70, calprotectin, histatins, mucins, basic proline rich proteins and peroxidases (host); |
| Infection (influenza) | miscellaneous | Hemagglutinin (H1), neuraminidase (N1); C-reactive protein, [RNA:] DNA cross-link repair 1A, PSO2 homolog, synaptonemal complex protein 3, v-maf musculoaponeurotic fibrosarcoma oncogene family, chitinase 3-like 3, matrix metalloproteinase 12, ATP-binding cassette, sub-family E (OABP), member 1, ATP-binding cassette, sub-family F (GCN20), member 1, feminization 1 homolog a (*C. elegans*), general transcription factor II H. polypeptide 2, forkhead box P1, zinc finger protein 282, arginyl-tRNA synthetase-like, Mitochondrial ribosomal protein L48, ribosomal protein S4, X-linked, eukaryotic translation elongation factor 1 alpha 1, proteaseome (prosome, macropain) 28 subunit 3, GLE1 RNA export mediator-like (yeast), small nuclear ribonucleoprotein polypeptide A', cleavage and polyadenylation specific factor 2, ribosomal protein L27a,, thioredoxin domain containing 4 (endoplasmic reticulum), flap structure specific endonuclease 1, ADP-ribosylation factor-like 6 interacting protein 2, cytidine 5'-triphosphate synthase 2, glutathione S-transferase, mu 5, phospholipase D1, aspartate-beta-hydroxylase, leukotriene A4 hydrolase, cytochrome P450 family 17, subfamily a, polypeptide 1, thioredoxin interacting protein, carbonyl reductase 2, |

TABLE 2-continued

| Diagnostic Markers | | |
|---|---|---|
| Disease/Condition | Source | Biomarker |
| | | alpha globin regulatory element containing gene, male-specific lethal-2 homolog (*Drosophila*), RAB1, member RAS oncogene family, protein tyrosine phosphatase, non-receptor type 21, potassium voltage-gated channel, Isk-related subfamily, gene 3, Bcl2-associated athanogene 3, lymphocyte cytosolic protein 2, pore forming protein-like, tumor necrosis factor receptor superfamily, member 19, filamin beta, microtubule-actin crosslinking factor 1, keratin complex 1, acidic, gene 18, keratin complex 1, acidic, gene 19, mesoderm development candidate 2, tubulin, alpha 4,, glutathione peroxidase 1, integrin linked kinase, guanine nucleotide binding protein, alpha inhibiting 2, cyclin L2, tubulin, alpha 2, DEAD (Asp-Glu-Ala-Asp) box polypeptide 5, programmed cell death 4, proteasome (prosome, macropain) 26S subunit, non-ATPase 8, signal sequence receptor, beta, RAD23b homolog (host); |
| Infection (HIV-1) | Urine, serum | p24, gp41, gp120 |
| Infection (Hepatitis B virus) | miscellaneous | Core, Envelope, Surface (Ay), |
| Infection (Hepatitis C virus) | miscellaneous | Core, NS3, NS4, NS5, |
| Infection (Hepatitis E virus) | miscellaneous | orf2 3 KD, orf2 6 KD, orf3 3 KD |
| Infection (*Vibrio cholerae*) | miscellaneous | Cholera Toxin |
| Infection (*Corynebacterium diphtheria*) | miscellaneous | Diphtheria toxin |
| Infection (Epstein-Barr virus) | miscellaneous | EA, VCA, NA |
| Infection (Herpes simplex virus HSV-1) | miscellaneous | gD |
| Infection (Herpes simplex virus HSV-2) | miscellaneous | gG |
| Infection (*Clostridium tetani*) | miscellaneous | Tetanus toxin |
| Infection (*Treponema pallidum*) | miscellaneous | 15 kd, p47 |
| Infection (*Entamoeba histolytica*) | saliva | M17 |
| Infection (*Toxoplasma gondii*) | serum | a2-HS glycoprotein and apB glycoprotein (host); TGME49 052280, TGME49_021500, TGME49J) 19630, TGME49_061720 and TGME49_076220; |
| Infection (Dengue virus) | miscellaneous | IL-10, fibrinogen, C4A, immunoglobulin, tropomyosin, albumin, SCSb-9 complement complex (host); NS-1 |
| Infection (*Streptococcus pneumonia*) | miscellaneous | stratifin, cullin 1, selenoprotein K, metal response element binding transcription factor 2, prostaglandin E synthase 2, HLA-B associated transcript 4, zinc finger protein (C2H2 type) 276, GCIP-interacting protein p29, mitochondrial ribosomal protein L20, aryl hydrocarbon receptor nuclear translocator-like, secretory carrier membrane protein 1, nuclear receptor subfamily 5, group A, member 2, NIMA (never in mitosis gene a)-related expressed, kinase 7, ribosomal protein L28, ribosomal protein S25, lysosomal-associated protein |

TABLE 2-continued

| Diagnostic Markers | | |
|---|---|---|
| Disease/Condition | Source | Biomarker |
| | | transmembrane 5, neural precursor cell expressed, developmentally, down-regulted gene 4, alpha glucosidase 2, alpha neutral subunit, coatomer protein complex, subunit beta 2 (beta prime), ribosomal protein L3, NADH dehydrogenase (ubiquinone) 1 alpha, subcomplex, assembly factor 1, isoprenylcysteine carboxyl methyltransferase,, cytoplasmic polyadenylation element binding protein 3, mannoside acetylglucosaminyltransferase 1, RNA-binding region (RNP1, RRM) containing 1,, folate receptor 4 (delta), ATPase, H+ transporting, lysosomal 50/57 kDa, V1, subunit H, zinc finger, DHHC domain containing 6, phosphoribosyl pyrophosphate synthetase-associated, protein 2, choline/ethanolaminephosphotransferase 1,, solute carrier family 38, member 1, ATP synthase, H+ transporting, mitochondrial F0, complex, subunit f, isoform 2, glucose phosphate isomerase 1, 2'-5' oligoadenylate synthetase 1A, tyrosine hydroxylase, hemoglobin alpha, adult chain 1, selenoprotein P, plasma, 1, acetyl-Coenzyme A dehydrogenase, long-chain, mannosidase, beta A, lysosomal,, deltex 3 homolog (*Drosophila*), ras homolog gene family, member AB, estrogen receptor 1 (alpha), phosphoglycerate kinase 1,, keratin complex 2, basic, gene 8, emerin, nucleoporin 153, formin 2, prothymosin alpha, synapsin I,,cullin 4B, regulator of chromosome condensation (RCC1) and, BTB (POZ) domain containing protein 1,, immediate early response 5, SAM domain and HD domain, 1, tumor rejection antigen gp96, lymphocyte antigen 6 complex, locus E,, DAZ associated protein 2, general transcription factor II I, RNA polymerase II transcriptional coactivator, SWI/SNF-related, matrix-associated actin-dependent, regulator of chromatin, subfamily a, containing DEAD/H, box 1, structure specific recognition protein 1, ankyrin repeat and FYVE domain containing 1, SET translocation, myocyte enhancer factor 2A, homeo box D9, H2A histone family, member Z, cellular nucleic acid binding protein,, golgi reassembly stacking protein 2, cathepsin L, eukaryotic translation initiation factor 5, ubiquitin specific protease 9, X chromosome, proteasome (prosome, macropain) subunit, alpha type 7, pescadillo homolog 1, containing BRCT domain, (zebrafish), heterogeneous nuclear ribonucleoprotein K, DEAD (Asp-Glu-Ala-Asp) box polypeptide 52, sorting nexin 5, cathepsin B, DnaJ (Hsp40) homolog, subfamily B, member 9, ribosomal protein S3a,, cytoplasmic polyadenylation element binding protein 4, 5'-3' exoribonuclease 2, small nuclear ribonucleoprotein polypeptide F,, arachidonate 5-lipoxygenase activating protein, cytochrome c oxidase, subunit Vlc, RIKubiquinol cytochrome c reductase core protein 2, lactate dehydrogenase 2, B chain, ubiquinol-cytochrome c reductase core protein 1, ATP synthase, H+ transporting, mitochondrial F0, complex, subunit b, isoform 1, microsomal glutathione S-transferase 1, ras homolog gene family, member A, RAB7, member RAS oncogene family, EGF-like module containing, mucin-like, hormone, receptor-like sequence 1, annexin A6, mitogen activated protein kinase 3, tyrosine kinase, non-receptor, 2, villin 2, tubulin, beta 5, catenin src (host); Pneumolysin, pneumococcal histidine triad D (PhtD), pneumococcal histidine triad E (PhtE), LytB, and pneumococcal choline-binding protein A (PcpA) |
| Infection (*Mycoplasma pneumonia*) | miscellaneous | Dnak, L7/L12, P1, exotoxin |
| Infection (*Campylobacter jejuni*) | miscellaneous | gyrA, 16S rDNA, or flaA/flaB |

TABLE 2-continued

| Diagnostic Markers | | |
|---|---|---|
| Disease/Condition | Source | Biomarker |
| Infection (*Bacillus anthracis*) | miscellaneous | Lethal factor, HtrA (BA3660), NlpC/P60-domain endopeptidase (BA1952), BA0796 locus (BA0796), SAP |
| Infection (West Nile virus) | miscellaneous | |
| Infection (Human papilloma virus) | miscellaneous | E6, E7 |
| Infection | urine | RNase 7 (host); |
| Infection (coronavirus :Sars, Mers, Sars-cov-2/COVID-19) | Nasal swab | spike, nucleocapsid, orf1a, orf1ab, orf3a, orf6, orf7a, orf7b, orf10, membrane glycoprotein, envelop protein |
| | Saliva | spike, nucleocapsid, orf1a, orf1ab, orf3a, orf6, orf7a, orf7b, orf10, membrane glycoprotein, envelop protein |
| | Blood | spike, nucleocapsid, orf1a, orf1ab, orf3a, orf6, orf7a, orf7b, orf10, membrane glycoprotein, envelop protein |

The following Table 3 provides a list of biomarkers that can be detected and quantified using the disclosed method, and correlated to associated diseases or health conditions.

TABLE 3

| Diagnostic Biomarkers | | |
|---|---|---|
| Health Condition | Source | Biomarkers |
| Diabetes | Saliva | plgR, Arp 3, CA VI, and IL-1Ra; PLS-2, LEI, and IGJ chain, resistin |
| | miscellaneous | ATP-binding cassette, sub-family C (CFTR/MRP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine |

TABLE 3-continued

| Diagnostic Biomarkers | | |
|---|---|---|
| Health Condition | Source | Biomarkers |
| | | palmitoyltransferase I; carnitine palmitoyltransferase Il; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; |

TABLE 3-continued

| Diagnostic Biomarkers | | |
|---|---|---|
| Health Condition | Source | Biomarkers |
| | | nuclear respiratory factor 1; oxytocin, prepro- (neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta-melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth |

TABLE 3-continued

| Diagnostic Biomarkers | | |
|---|---|---|
| Health Condition | Source | Biomarkers |
| | | factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |
| Metabolic syndrome/ prediabetes | Serum | GFAP autoantibodies |
| Kidney failure/disease | saliva<br>miscellaneous | Lactoferrin, uric acid, cortisol, alpha-amylase<br>ADBP-26, NHE3, KIM-1, glutamyltransferase, N-acetyl-beta-D-glucosaminidase, lysozyme, NGAL, L-FABP, bikunin, urea, prostaglandins, creatinine, alpha-1-microglobulin, retinol binding protein, glutathione-S-transferases, adiponectin, beta-2-macroglobuin, calbindin-D, cysteine-rich angiogenic inducer 61, endothelial/epithial growth factors, alpha-1-acid glycoprotein (orosomucoid), prealbumin, modified albumin, albumin, transferrin, alpha-1-lipoprotein, alpha-1-antitrypsin matrix metalloproteinases (MMPs), alpha-1-fetoprotein, Tamm Horsfall protein, homoarginine, interleukin 18, monocyte chemotactic protein-1 (MCP-1), Lipocalin, VCAN, NRP1, CCL2, CCL19, COL3A1, GZMM, alpha-galactosidase, casein kinase 2, IP-10, Mig, I-TAC, MIP-1α, MIP-3α, and MIP-1β, alpha-2-glycoprotein-Zinc, leucine-rich alpha-2-glycoprotein, uromodulin, Pacsin 2, hepcidin-20, hepcidin-25, AIF-2, urinary type-IV collagen, lipocalin-type prostaglandin D synthase (L-PGDS), urinary neutrophil gelatinase-associated lipocalin (uNGAL), Annexin A1, Rab23, Shh, Ihh, Dhh, PTCH1, PTCH2, SMO, Gli1, Gli2, Gli3, TLR4, cystatin C, AQPI, AQP2, AQP3, NKCC2, NaPill, DAHKSEVAHRFKD [RNA:] SLC12A1, UMOD, vWF, MMPI, MMP3, SLC22A6, SLC22A 8, SLC22A 12, podocin, cubulin, LRP2, AQP9, and albumin, carcinoembryonic antigen (CEA), mucin, alpha-fetoprotein, tyrosinase, melanoma associated antigen, mutated tumor protein 53, p21, PUMA, prostate-specific antigen (PSA) or thyroglobulin, von Willebrand factor (VWF), thrombin, factor VIII, plasmin, fibrin, osteopontin (SPP1), Rab23, Shh, Ihh, Dhh, PTCH1, PTCH2, SMO, Gli1, Gli2, Gli3 |
| Liver failure/disease | miscellaneous | Carnitine; Cholic Acid; Chenodeoxycholic, Deoxycholic, Lithocholic, Glycocholic; Prostaglandin $E_2$; 13,14-dihydro-15-keto Prostaglandin A2; Prostaglandin B2; Prostaglandin F2a; 15-keto-Prostaglandin F2α; 6-keto-Prostaglandin F1α; Thromboxane B2; 11-dehydro-Thromboxane B2; Prostaglandin D2; Prostaglandin J2; 15-deoxy-Δ12, 14-Prostaglandin J2; 11β-Prostaglandin F2a; 5(S)-Hydroxyeicosatetraenoic acid; 5(S)-Hydroxyeicosapentaenoic acid; Leukotriene B4; Leukotriene B5; Leukotriene C4; Leukotriene D4; Leukotriene E4; Leukotriene F4; 12(S)-Hydroxyeicosatetraenoic acid; 12(S)-Hydroxyeicosapentaenoic acid; 15(S)-Hydroxyeicosatetraenoic acid; 15(S)-Hydroxyeicosapentaenoic acid; Lipoxin A4; 8(S)-Hydroxyeicosatetraenoic acid; 9-Hydroxyeicosatetraenoic acid; 11- |

TABLE 3-continued

Diagnostic Biomarkers

| Health Condition | Source | Biomarkers |
|---|---|---|
| | | Hydroxyeicosatetraenoic acid; 8-iso-Prostaglandin F2α; 9-Hydroxyoctadecadienoic acid; 13-Hydroxyoctadecadienoic acid; 20(S)-Hydroxyeicosatetraenoic acid; 9,10-Epoxyoctadecenoic acid; 12,13-Epoxyoctadecenoic acid; 12,13-Dihydroxyoctadecenoic acid; 5,6-Epoxyeicosatrienoic acid; 11,12-Epoxyeicosatrienoic acid; 14,15-Epoxyeicosatrienoic acid; 5,6-Dihydroxyeicosatrienoic acid; 8,9-Dihydroxyeicosatrienoic acid; 11,12-Dihydroxyeicosatrienoic acid; 14,15-Dihydroxyeicosatrienoic acid; 14,15-Epoxyeicosatetraenoic acid; 17,18-Epoxyeicosatetraenoic acid; 14,15-Dihydroxyeicosatetraenoic acid; 17,18-Dihydroxyeicosatetraenoic acid; 19,20-Dihydroxydocosapentaenoic acid; diacetylspermine, hemopexin, TLR4 |
| Heart failure | miscellaneous | SFRP-3, NT-proBNP, troponin T, SKITHRIHWESASLL (SEQ ID NO: 20), AHKSEVAHRFK (SEQ ID NO: 21), uroguanylin, BNP |
| Cardiovascular health | miscellaneous | miR-378, miR-497, miR-21, miR-15b, miR-99a, miR29a, miR-24, miR-30b, miR-29c, miR-331.3p, miR-19a, miR-22, miR-126, let-7b, miR-502.3, and miR-652 IL-16, sFas, Fas ligand, MCP-3, HGF, CTACK, EOTAXIN, adiponectin, IL-18, TIMP.4, TIMP.1, CRP, VEGF, and EGF |
| | saliva | C-reactive protein (CRP); myoglobin (MYO), creatinine kinase myocardial band (CK-MB), cardiac troponins (cTn), and myeloperoxidase; TNF-α, and MMP-9; CD40 |
| High blood pressure | saliva | lysozyme |
| Tiredness/fatigue | urine | endorepellin |
| | saliva | PPGKPQGPPPQGGNQPQGPPPPPGKPQ (SEQ ID NO: 15); GNPQGPSPQGGNKPQGPPPPPGKPQ (SEQ ID NO: 16); SPPGKPQGPPQQEGNKPQGPPPPGKPQ (SEQ ID NO: 17) |
| | urine | human herpesvirus 6, human herpesvirus 7, human cytomegalovirus, and Epstein-Barr virus (EBV) |
| | miscellaneous | GGHPPPP (SEQ ID NO: 18), ESPSLIA (SEQ ID NO: 19); |
| Malnutrition | Saliva | slgA |
| Depressive disorder | miscellaneous | Secretogranin, VGF |
| Alzheimer's disease | CSF, serum, saliva | β-amyloid(1-42), β-amyloid(1-40), tau, phosphor-tau-181 |
| Stress | saliva | Cortisol, dehydro-androsteronesulfate; 17-ketosteroidsulfate; dehydro-epiandrostronesulfate; corticosteroid, 17-hydroxycorticosteroid, chromogranin A, alpha-amylase, secretary IgA, lysozyme, growth hormone, oxytocin |
| | miscellaneous | aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione S-transferase p, GroEL, heat shock protein 25/27, heat shock protein 40, heat shock protein 60, heat shock protein 70, heat shock protein 90, heat shock transcription factor-1, heme oxygenase-1, interleukin 1β, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, |

TABLE 3-continued

| Diagnostic Biomarkers | | |
|---|---|---|
| Health Condition | Source | Biomarkers |
| | | transforming growth factor β, tumor suppressor p53, and vasoactive intestinal peptide |
| Circadian rhythm | saliva | melatonin |
| Bone turnover/ Osteoporosis | Urine | Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b |
| | saliva | deoxypyridinium (D-PYR) and osteocalcin (OC), hepatocyte growth factor and interleukin-1 beta |
| Muscle damage | Serum, urine | Myoglobin, creatine kinase (CK), lactate dehydrogenase (LDH), aldolase, troponin, carbonic anhydrase type 3 and fatty acid-binding protein (FABP), transaminases |
| Exercise/athletic activity | sweat | urea |
| | serum | Myostatin, follistatin-like related gene |
| | saliva | testosterone |
| Performance enhancement | miscellaneous | interleukin-6, interleukin-1 beta, G-CSF, interferon-gamma, interleukin-8, interleukin-9, MCP-1, MIP-beta, and/or TNF alpha |
| Energy balance (protein excretion)/ energy status / metabolic state | Serum | AMPK |
| | Urine, sweat, feces | pre-albumin, retinol binding protein, urea |
| | miscellaneous | cholesterol, lipoproteins, insulin, insulin C peptide, IGF binding proteins, e.g. IGF-BPI, liver enzymes |
| Growth | Saliva | IGF-1 |
| Andropause | saliva | testosterone; testosterone precursors such as pregnenolone, progesterone, 17-hydroxypregnenolone, 17-hydroxyprogesterone, dehydroepiandrosterone (DHEA) and delta-4-androstene-3,17-dione; testosterone and dihydrotestosterone metabolites such as the 17-ketosteroids androsterone and etiocholanolone, polar metabolites in the form of diols, triols, and conjugates, as well estradiol, estrogens, androsteindione, cortisol, DHEA, FSH (follicle stimulating hormone), LH (luteinizing hormone), and GnRH (gonadotropin-releasing hormone) |
| Menopause | Saliva | Follicle stimulating hormone (FSH) Estrogen and progesterone, testosterone, free testosterone, and dehydroepiandrosterone sulfate (DHEAS), cortisol and dehydroepiandrosterone (DHEA) |
| Pregnancy/fetal development | Saliva | progesterone |
| | urine | human chorionic gonadotropin, Levonorgestrel, alpha-fetoprotein |
| | serum | estradiol |
| Breast cancer | urine | 47D10 antigen, PTCD2, SLC25A20, NFKB2, RASGRP2, PDE7A, MLL, PRKCE, GPATC3, PRIC285 and GSTA4, MIPEP, PLCB2, SLC25A19, DEF6, ZNF236, C18orf22, COX7A2, DDX11, TOP3A, C9orf6, UFC1, PFDN2, KLRD1, LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, LOC284184, FLJ23235, GPATC3, CPSF4, CREM, HIST1H1D, HPS4, FN3KRP, ANKRD16, C8 orf16, ATF71P2, PRIC285 |
| Prostate cancer | Serum/saliva | Prostate specific antigen (PSA) |
| | Urine | PCA3, GOLPH2, SPINK1, TMPRSS2: ERG |
| Infections | | See Table 2 |
| Dental caries/periodontal disease | Saliva | aspartate aminotransferase (AST) and alkaline phosphatase (ALP), uric acid and albumin; 12-HETE; MMP-8, TIMP-1, and ICTP |

TABLE 3-continued

| Diagnostic Biomarkers | | |
|---|---|---|
| Health Condition | Source | Biomarkers |
| Heavy metal poisoning | saliva | lead, cadmium |
| Drugs/drug | saliva | marijuana, Cocaine (crystalline tropane alkaloid), methamphetamine, amphetamine, heroin, methyltestosterone, mesterolone, morphine, cyclophosphamide metabolites, Haloperidol, barbiturates; antipyrine, caffeine, cisplatin, cyclosporine, diazepam, digoxin, methadone, phenytoin, theophylline, tolbutamide. Nicotine/cotinine, cannabis |
| metabolites | urine | trichloroethanol glucuronide, Anabolic steroids, Androstenedione, Benzodiazepines, Chlordiazepoxide, Lorazepam, Zidovudine |
| Allergies | saliva | Allergen-specific IgAs (see Tables 7 and 9) |

In some instances, the biomarker to be detected using the present method is a micro RNA (miRNA) biomarker that is associated with a disease or a health condition. The following Table 7 provides a list of miRNA biomarker that can be detected using the present method.

TABLE 7

| Diagnostic miRNA Markers | |
|---|---|
| Disease/Condition | Biomarker* |
| Breast cancer | miR-10b, miR-21, miR-125b, miR-145, miR-155, miR-191, miR-382, MiR-1, miR-133a, miR-133b, miR-202, miR-1255a, miR-671-3p, miR-1827, miR-222, miR-744, miR-4306, miR-151-3p, miR-130, miR-149, miR-652, miR-320d, miR-18a, miR-181a, miR-3136, miR-629, miR-195, miR-122, miR-375, miR-184, miR-1299, miR381, miR-1246, miR-410, miR-196a, miR-429, miR-141, miR-376a, miR-370, miR-200b, miR-125a-5p, miR-205, miR-200a, miR-224, miR-494, miR-216a, miR-654-5p, miR-217, miR-99b, miR-885-3p, miR-1228, miR-483-5p, miR-200c, miR-3065-5p, miR-203, miR-1308, let-7a, miR-17-92, miR-34a, miR-223, miR-150, miR-15b, miR-199a-5p, miR-33a, miR-423-5p, miR-424, let-7d, miR-103, miR-23b, miR-30d, miR-425, miR-23a, miR-26a, miR-339-3p, miR-127-3p, miR-148b, miR-376a, miR-376c, miR-409-3p, miR-652, miR- 801, (miR-92a, miR-548d-5p, miR-760, miR-1234, miR-18b, miR-605, miR-193b, miR-29) |
| Leukemia | miR-98, miR-155, miR-21, let-7, miR-126, miR-196b, miR-128, miR-195, miR-29a, miR-222, miR-20a, miR-150, miR-451, miR-135a, miR-486-5p, miR-92, miR-148a, miR-181a, miR-20a, miR-221, miR-625, miR-99b<br>(miR-92a, miR-15, miR-16, miR-15a, miR-16-1, miR-29) |
| Multiple myeloma | miR-15a, miR-16, miR-193b-365, miR-720, miR-1308, miR-1246, miR-1, miR-133a, miR-221, miR-99b, Let-7e, miR-125a-5p, miR-21, miR-181a/b, miR-106b-25, miR-32, miR-19a/b, miR-17-92, miR-17, miR-20, miR-92, miR-20a, miR-148a, miR-153, miR-490, miR-455, miR-642, miR-500, miR-296, miR-548d, miR-373, miR-554, miR-888, miR-203, miR-342, miR-631, miR-200a, miR-34c, miR-361, miR-9*, miR-200b, miR-9, miR-151, miR-218, miR-28-3p, miR-200c, miR-378, miR-548d-5p, miR-621, miR-140-5p, miR-634, miR-616, miR-130a, miR-593, miR-708, miR-200a*, miR-340, miR-760, miR-188-5p, miR-760, miR-885-3p, miR-590-3p, miR-885-5p, miR-7, miR-338, miR-222, miR-99a, miR-891a, miR-452, miR-98, miR-629, miR-515-3p, miR-192, miR-454, miR-151-3p, miR-141, miR-128b, miR-1227, miR-128a, miR-205, miR-27b, miR-608, miR-432, miR-220, miR-135a, miR-34a, miR-28, miR-412, miR-877, miR-628-5p, miR-532-3p, miR-625, miR-34b, miR-31, miR-106b, miR-146a, miR-210, miR-499-5p, miR-140, miR-188, miR-610, miR-27a, miR-142-5p, miR-603, miR-660, miR-649, miR-140-3p, miR-300, miR-335, miR-206, miR-20b, miR-130b, miR-183, miR-652, miR-133b, miR-191, miR-212, miR-194, miR-100m miR-1234m miR-182m miR-888, miR-30e-5p, miR-574, miR-135b, miR-125b, miR-502m miR-320, miR548-421, miR-129-3p, miR-190b, miR-18a, miR-549, 338-5p, miR-756-3p, miR-133a, miR-521, miR-486-3p, miR-553, miR-452*, miR-628-3p, miR-620, miR-566, miR-892a, miR- miR-339-5p, miR- |

TABLE 7-continued

| Diagnostic miRNA Markers | |
|---|---|
| Disease/Condition | Biomarker* |
| | 628, miR-520d-5p, miR-297, miR-213, miR-519e*, miR-422a, miR-198, miR-122a, miR-1236, miR-548c-5p, miR-191*, miR-583, miR-376c, miR-34c-3p, miR-453, miR-509, miR-124a, miR-505, miR-208, miR-659, miR-146b, miR-518c, miR-665, miR-324-5p, miR-152, miR-548d, miR-455-3p (miR-15a, miR-373*, miR-378*, miR-143, miR-337, miR-223, miR-369-3p, miR-520g, miR-485-5p, miR-524, miR-520h, miR-516-3p, miR-519d, miR-371-3p, miR-455, miR-520b, miR-518d, miR-624, miR-296, miR-16) |
| monoclonal gammopathy of undetermined significance | miR-21, miR-210, miR-9*, miR-200b, miR-222, miR-376 (miR-339, miR-328) |
| Myelodisplastic syndrome | (Let-7a, miR-16) |
| Lymphoma | miR-155, miR-210, miR-21, miR-17-92, miR-18a, miR-181a, miR-222, miR-20a/b, miR-194, miR-29, miR-150, miR-155, miR-223, miR-221, let-7f, miR-146a, miR-15, miR-16-1, miR-34b/c, miR-17-5p (miR-20b, miR-184, miR-200a/b/c, miR-205, miR-34a, miR-29a, miR-29b-1, miR-139, miR-345, miR-125a, miR-126, miR-26a/b, miR-92a, miR-20a, miR-16, miR-101, miR-29c miR-138, miR-181b) |
| Lung cancer | let-7c, miR-100, miR-10a, miR-10b, miR-122a, miR-125b, miR-129, miR-148a, miR-150, miR-17-5p, miR-183, miR-18a*, miR-18b, miR-190, miR-192, miR-193a, miR-196b, miR-197, miR-19a, miR-19b, miR-200c, miR-203, miR-206, miR-20b, miR-210, miR-214, miR-218, miR-296, miR-30a-3p, miR-31, miR-346, miR-34c, miR-375, miR-383, miR-422a, miR-429, miR-448, miR-449, miR-452, miR-483, miR-486, miR-489, miR-497, miR-500, miR-501, miR-507, miR-511, miR-514, miR-516-3p, miR-520d, miR-527, miR-7, miR-92, miR-93, miR-99a, miR-25, miR-223, miR-21, miR-155, miR-556, miR-550, miR-939, miR-616*, miR-146b-3p and miR-30c-1*, miR-142-5p, miR-328, miR-127, miR-151, miR-451, miR-126, miR-425-5p, miR-222, miR-769-5p, miR-642, miR-202, miR-34a (let-7a, let-7d, let-7e, let-7g, let-7i, miR-1, miR-103, miR-106a, miR-125a, miR-130a, miR-130b, miR-133a, miR-145, miR-148b, miR-15a, miR-15b, miR-17-3p, miR-181d, miR-18a, miR-196a, miR-198, miR-199a, miR-199a*, miR-212, miR-22, miR-221, miR-23a, miR-23b, miR-26a, miR-27a, miR-27b, miR-29b, miR-30b, miR-30d, miR-30e-3p, miR-320, miR-323, miR-326, miR-331, miR-335, miR-339, miR-374, miR-377, miR-379, miR-410, miR-423, miR-433, miR-485-3p, miR-485-5p, miR-487b, miR-490, miR-491, miR-493, miR-493-3p, miR-494, miR-496, miR-502, miR-505, miR-519d, miR-539, miR-542-3p, miR-98) |
| Colorectal cancer | miR-29a, miR-17-3p, miR-92, miR-21, miR-31, miR-155, miR-92a, miR-141, mir-202, mir-497, mir-3065, mir-450a-2, mir-3154, mir-585, mir-3175, mir-1224, mir-3117, mir-1286 (miR-34) |
| Prostate cancer | miR-141, miR-375, miR-16, miR-92a, miR-103, miR-107, miR-197, miR-485-3p, miR-486-5p, miR-26a, miR-92b, miR-574-3p, miR-636, miR-640, miR-766, miR-885-5p, miR-141, miR-195, miR-375, miR-298, miR-346, miR-1-1, miR-1181, miR-1291, miR-133a-I, miR-133b, miR-1469, miR-148*, miR-153, miR-182, miR-182*, miR-183, miR-183*, miR-185, miR-191, miR-192, miR-1973, miR-200b, miR-205, miR-210, miR-33b*, miR-3607-5p, miR-3621, miR-378a, miR-429, miR-494, miR-582, miR-602, miR-665, miR-96 , miR-99b*, miR-100, miR-125b, miR-143, miR-200a, miR-200c, miR-222, miR-296, and miR-425-5p |
| Ovarian cancer | miR-21, miR-92, miR-93, miR-126, miR-29a, miR-141, miR-200a/b/c, miR-203, miR-205, miR-214, miR-221, miR-222, miR-146a, miR-150, miR- 193a-5p, miR-31, miR-370, let-7d, miR-508-5p, miR-152, miR-509-3-5p, miR-508-3p, miR-708, miR-431, miR-185, miR-124, miR-886-3p, hsa-miR-449, hsa-miR-135a, hsa-miR-429, miR-205, miR-20b, hsa-miR-142-5p, miR-29c, miR-182 (miR-155, miR-127, miR-99b) |
| Cervical cancer | miR-21, miR-9, miR-200a, miR-497 (miR-143, miR-203, miR-218) |
| Esophageal carcinoma | miR-21, hsa-miR-200a, hsa-miR-345, hsa-miR-373*, hsa-miR-630, hsa-miR-663, hsa-miR-765, hsa-miR-625, hsa-miR-93, hsa-miR-106b, hsa-miR-155, hsa-miR-130b, hsa-miR-30a, hsa-miR-301a, hsa-miR-15b (miR-375) |
| Gastric cancer | miR-17-5p, miR-21, miR-106a, miR-106b, miR-187, miR-371-5p, miR-378 (let-7a, miR-31, miR-192, miR-215, miR-200/141) |
| Pancreatic cancer, ductal adenocarcinoma | miR-210, miR-21, miR-155, miR-196a, miR-1290, miR-20a, miR-24, miR-25, miR-99a, miR-185, miR-191, miR-18a, miR-642b-3p, miR-885-5p, miR-22-3p, miR-675, miR-212, miR-148a*, miR-148, miR- |

TABLE 7-continued

| Diagnostic miRNA Markers | |
|---|---|
| Disease/Condition | Biomarker* |
| | 187, let-7g*, miR-205, miR-944, miR-431, miR-194*, miR-769-5p, miR-450b-5p, miR-222, miR-222*, miR-146, miR-23a*, miR-143*, miR-216a, miR-891a, miR-409-5p, miR-449b, miR-330-5p, miR-29a*, miR-625 |
| Hepatocellular carcinoma | miR-500, miR-15b, miR-21, miR-130b, miR-183, miR-122, miR-34a, miR-16, miR-221, miR-222 |
| Melanoma | miR-150, miR-15b, miR-199a-5p, miR-33a, miR-423-5p, miR-424, miR- let-7d, miR-103, miR-23b, miR-30d, miR-425, miR-222, miR-23a, miR-26a, miR-339-3p |
| Squamous cell carcinoma | miR-184a |
| Bladder cancer | miR-126, miR-182 (urine), miR-16, miR-320 (miR-143, miR-145, miR-200/141) |
| Renal cancer | miR-1233, miR-199b-5p, miR-130b (miR-10b, miR-139-5p) |
| Oral cancer | miR-31, miR-24, miR-184; miR-34c; miR-137; miR-372; miR-124a; miR-21; miR-124b; miR-31; miR-128a; miR-34b; miR-154; miR-197; miR-132; miR-147; miR-325; miR-181c; miR-198; miR-155; miR-30a-3p; miR-338; miR-17-5p; miR-104; miR-134; miR-213 (miR-200a, miR-125a, miR-133a; miR-99a; miR-194; miR-133; miR-219; miR-100; miR-125; miR-26b; miR-138; miR-149; miR-195; miR-107; and miR-139 (saliva)) |
| Head and neck cancer | miR-455-3p, miR-455-5p, miR-130b, miR-130b*, miR-801, miR-196a, miR-21, miR-31 |
| Endometrial cancer | miR-503, miR-424, miR-29b, miR-146a, miR-31 |
| Testicular cancer | miR-372, miR-373 |
| Glioblastoma | miR-21, miR-221, miR-222 |
| Thyroid cancer | miR-187, miR-221, miR-222, miR-146b, miR-155, miR-224, miR-197, miR-192, miR-328, miR-346, miR-512-3p, miR-886-5p, miR-450a, miR-301 b, miR-429, miR-542-3p, miR-130a, miR-146b-5p, miR-199a-5p, miR-193a-3p, miR-152, miR-199a-3p/miR-199b-3p, miR-424, miR-22, miR-146a, miR-339-3p, miR-365, let-7i*, miR-363*, miR-148a, miR-299-3p, let-7a*, miR-200b, miR-200c, miR-375, miR-451 , miR-144, let-7i, miR-1826, miR-1201 , miR-140-5p, miR-126, miR-126*, let-7f-2*, miR-148b, miR-21 *, miR-342- 3p, miR-27a, miR-145*, miR-513b, miR-101 , miR-26a, miR-24, miR-30a*, miR-377, miR-518e7, miR-519a7, miR-519b-5p, miR-519c-5p, miR-5227, miR-523*, miR-222*, miR-452, miR-665, miR-584, miR-492, miR-744, miR-662, miR-219-2-3p, miR-631 and miR-637, miRPlus-E1078, miR-19a, miR-501-3p, miR-17, miR-335, miR-106b, miR-15a, miR-16, miR-374a, miR-542-5p, miR-503, miR-320a, miR-326, miR-330-3p,<br>miR-1, miR-7b, miR-26b, miR-106a, miR-139, miR-141, miR-143, miR-149, miR-182, miR-190b, miR-193a, miR-193b, miR-211, miR-214, miR-218, miR-302c*, miR-320, miR-324, miR-338, miR-342, miR-367, miR-378, miR-409, miR-432, miR-483, miR-486, miR-497, miR-518f, miR-574, miR-616, miR-628, miR-663b, miR-888, miR-1247, miR-1248, miR-1262, and miR-1305<br>miR-21, miR-25, miR-32, miR-99b*, miR-125a, miR-125b, miR-138, miR-140, miR-181a, miR-213, miR-221, miR-222, and miR-345 |
| Ischemic heart disease/ Myocardial infarction | miR-1, miR-30c, miR-133, miR-145, miR-208a/b, miR-499, miR-663b, miR-1291 (miR-126, miR-197, miR-223) |
| Heart failure | miR-29b, miR-122, miR-142-3p, miR-423-5p, miR-152, miR-155, miR-497 (miR-107, miR-125b, miR-126, miR-139, miR-142-5p, miR-497) |
| Stroke | miR-124, miR-145 (miR-210) |
| Coronary artery disease | miR-21, miR-27b, miR-130a, miR-134, miR-135a, miR-198, miR-210, miR-370 (miR-17, miR-92a, miR-126, miR-145m miR-155m miR-181a, miR-221, miR-222) |
| Diabetes | miR-9, miR-28-3p, miR-29a, miR-30d, miR-34a, miR-124a, miR-146a, miR-375, miR-503, 144 (miR-15a, miR-20b, miR-21, miR-24, miR-126, miR-191, miR-197, 223, miR-320, miR-486) |
| Hypertension | Hcmv-miR-UL112, Let-7e (miR-296-5p) |
| Chronic HCV infection | miR-155, miR-122, miR-125b, miR-146a, miR-21 |
| Liver injury | miR-122, miR-192 |
| Sepsis | miR-146a, miR223 |
| Arthritis | miR-125a-5p, miR-24, miR-26a, miR-9, miR-25, miR-98, miR-146a, miR-124a, miR-346, miR-223, miR-155 (miR-132, miR-146) |
| Systemic lupus erythematosus | (miR-200a/b/c, miR-205, miR-429, miR-192, miR-141, miR-429, miR-192 (urine or serum) |
| Chron disease | miR-199a-5p, miR-362-3p, miR-532-3p, miR-plus-E1271, miR-340* (miR-149*, miR-plus-F1065) |
| Ulcerative colitis | miR-28-5p, miR-151-5p, miR-199-5p, miR-340*, miR-plus-E1271, miR-103-2*, miR-362-3p, miR-532-3p (miR-505) |
| Asthma | miR-705, miR-575, let-7d, miR-173p, miR-423-5p, miR-611, miR-674, let-7f-1, miR-23b, miR-223, miR-142-3p, let-7c, miR-25, miR- |

TABLE 7-continued

Diagnostic miRNA Markers

| Disease/Condition | Biomarker* |
|---|---|
| | 15b, let-7g, and miR-542-5p, miR-370 (miR-325, miR-134, miR-198, miR-721, miR-515-3p, miR-680, miR-601, miR-206, miR-202, miR-671, miR-381, miR-630, miR-759, miR-564, miR-709, miR-513, miR-298) |
| Chronic pulmonary disease | miR-148a, miR-148b, miR-152 |
| Idiopathic pulmonary fibrosis | miR-199a-5p |
| Alzheimer's disease | (miR-137, miR-181c, miR-9, miR-29a/b) |
| Duchenne muscular dystrophy | miR-1, miR-133a, miR-206 |
| Multiple sclerosis | miR-633, miR-181c-5p (CSF), miR-17-5p, miR-193a, miR-326, miR-650, miR-155, miR-142-3p, miR-146a, miR-146b, miR-34a, miR-21, miR-23a, miR-199a, miR-27a, miR-142-5p, miR-193a, miR-15a, miR-200c, miR-130a, miR-223, miR-22, miR-320, miR-214, miR-629, miR-148a, miR-28, miR-195, miR-135a, miR-204, miR-660, miR-152, miR-30a-5p, miR-30a-3p, miR-365, miR-532, let-7c, miR-20b, miR-30d, miR-9, hsa-mir-18b, hsa-mir-493, hsa-mir-599, hsa-mir-96, hsa-mir-193, hsa-mir-328, hsa-mir-409-5p, hsa-mir-449b, hsa-mir-485-3p, hsa-mir-554 |
| | (miR-922 (CSF), miR-497, miR-1 and miR-126, miR-656, miR-184, miR-139, miR-23b, miR-487b, miR-181c, miR-340, miR-219, miR-338, miR-642, miR-181b, miR-18a, miR-190, miR-213, miR-330, miR-181d, miR-151, miR-140) |
| Preeclampsia | miR-210 (miR-152) |
| Gestational diabetes | (miR-29a, miR-132) |
| Platelet activity | miR-126, miR-197, miR-223, miR-24, miR-21 |
| Pregnancy/placenta-derived | miR-526a, miR-527, miR-520d-5p, miR-141, miR-149, miR-299-5p, miR-517a |
| Drug treatment for immunomodulation | miR-130a, miR-146b, miR-143, miR-145, miR-99b, miR-125a, miR-204, miR-424, miR-503 |
| Aging | (miR-151a-3p, miR-181a-5p, miR-1248) |

*miRNA markers in parentheses are downregulated

In some embodiments, the spacers are fixed on a plate by directly embossing the plate or injection molding of the plate.

In some embodiments, the materials of the plate and the spacers are selected from polystyrene, PMMA, PC, COC, COP, and another plastic.

In some embodiments, the inter-spacer distance is in the range of 1 um to 200 um.

In some embodiments, the inter-spacer distance is in the range of 200 um to 1000 um.

In some embodiments, the spacers regulating the layer of uniform thickness have a filling factor of at least 1%, wherein the filling factor is the ratio of the spacer area in contact with the layer of uniform thickness to the total plate area in contact with the layer of uniform thickness.

In some embodiments, for spacers regulating the layer of uniform thickness, the Young's modulus of the spacers times the filling factor of the spacers is equal to or larger than 10 MPa, wherein the filling factor is the ratio of the spacer area in contact with the layer of uniform thickness to the total plate area in contact with the layer of uniform thickness.

In some embodiments, for a flexible plate, the thickness of the flexible plate times the Young's modulus of the flexible plate is in the range 60 to 750 GPa-um.

In some embodiments, for a flexible plate, the fourth power of the inter-spacer distance (ISD) divided by the thickness of the flexible plate (h) and the Young's modulus (E) of the flexible plate, $ISD^4/(hE)$, is equal to or less than $10^6$ $um^3$/GPa.

In some embodiments, one or both plates comprises a location marker, either on a surface of or inside the plate, that provides information of a location of the plate.

In some embodiments, one or both plates comprises a scale marker, either on a surface of or inside the plate, that provides information of a lateral dimension of a structure of the sample and/or the plate.

In some embodiments, one or both plates comprises an imaging marker, either on surface of or inside the plate, that assists imaging of the sample.

In some embodiments, the spacers function as a location marker, a scale marker, an imaging marker, or any combination thereof.

In some embodiments, the average thickness of the layer of uniform thickness is about equal to a minimum dimension of the analyte in the sample.

In some embodiments, the inter-spacer distance is in the range of 1 um to 50 um.

In some embodiments, the inter-spacer distance is in the range of 50 um to 120 um.

In some embodiments, the inter-spacer distance is in the range of 120 um to 200 um.

In some embodiments, the inter-spacer distance is substantially periodic.

In some embodiments, the spacers are pillars with a cross-sectional shape selected from round, polygonal, circular, square, rectangular, oval, elliptical, and any combination of the same.

In some embodiments, the spacers have a pillar shape and have a substantially flat top surface, wherein, for each spacer, the ratio of the lateral dimension of the spacer to its height is at least 1.

In some embodiments, for each spacer, the ratio of the lateral dimension of the spacer to its height is at least 1.

In some embodiments, wherein a minimum lateral dimension of the spacer is less than or substantially equal to the minimum dimension of the analyte in the sample.

In some embodiments, a minimum lateral dimension of the spacer is in the range of 0.5 um to 100 um.

In some embodiments, a minimum lateral dimension of the spacer is in the range of 0.5 um to 10 um.

In some embodiments, the spacers have a density of at least 100/mm$^2$.

In some embodiments, the spacers have a density of at least 1000/mm$^2$.

In some embodiments, at least one of the plates is transparent.

In some embodiments, at least one of the plates is made from a flexible polymer.

In some embodiments, for a pressure that compresses the plates, the spacers are not compressible and/or, independently, only one of the plates is flexible.

In some embodiments, the flexible plate has a thickness in the range of 10 um to 200 um.

In some embodiments, the variation is less than 30%.

In some embodiments, the variation is less than 10%.

In some embodiments, the variation is less than 5%.

In some embodiments, the collection and cover plates are connected and are configured to be changed from the open configuration to the closed configuration by folding the plates.

In some embodiments, the collection and cover plates are connected by a hinge and are configured to be changed from the open configuration to the closed configuration by folding the plates along the hinge.

In some embodiments, the collection and cover plates are connected by a hinge that is a separate material to the plates, and are configured to be changed from the open configuration to the closed configuration by folding the plates along the hinge.

Aspects

Aspect 1. A method for determining the presence and the quantity of one or more intracellular biomarkers indicative of a disease in a sample containing at least one cell, comprising:

- contacting the sample containing at least one cell and an intracellular stain formulation for a targeted intracellular biomarker to form an intracellular reaction product within a closed Q-card if the targeted intracellular biomarker is present;
- imaging the intracellular reaction product with an imager to generate an image of the intracellular reaction product;
- analyzing the image to generate an analysis of the intracellular reaction product to determine the presence and the quantity of one or more intracellular biomarker; and
- generating at least one disease diagnosis by correlating the determined presence and the quantity of one or more intracellular biomarker measured in the method with a database of correlated biomarker and disease combinations.

Aspect 2. The method of Aspect 1, wherein the database of the correlated biomarker and disease combinations is based on an extracellular measured concentration of viral responsive biomarker and the diseased cell.

Aspect 3. The method of Aspect 1, wherein the intracellular stain formulation comprises an intracellular stain reagent containing an antibody probe molecule [e.g., AF488-anti-IL-4, and AF647-anti-IL6 antibodies] and/or oligonucleotide probe molecule [e.g., IL-6 Alexa488 60-mer oligo probe, SEQ ID NO: 1]; a buffer; and a cell permeabilizer.

Aspect 4. The method of Aspect 1, wherein the database of the correlated biomarker and disease combinations is based on an extracellular measured concentration of a viral biomarker and the diseased cell.

Aspect 5. The method of Aspect 1, wherein the intracellular stain formulation comprises an intracellular stain reagent containing a viral probe molecule [e.g., p24 protein or p24 mRNA]; a buffer; and a cell permeabilizer.

Aspect 6. The method of Aspect 1, wherein the intracellular stain formulation comprises a fluorescent-labeled oligo nucleotide probe.

Aspect 7. The method of Aspect 1, wherein at least one disease diagnosis is selected from: a blood cancer, an infectious disease, an autoimmune disease, a primary immunodeficiency (PID), a genetic disease, a benign urinary tract disease or condition, a urinary tract cancer, or a malignant disease.

Aspect 8. The method of Aspect 1, further comprising reporting the at least one disease diagnosis remotely with a communication device.

Aspect 9. The method of Aspect 1, wherein the intracellular stain formulation comprises an intracellular stain reagent containing a probe molecule; a buffer; and a cell permeabilizer.

Aspect 10. The method of Aspect 1, wherein the sample comprises a single cell.

Aspect 11. The method of Aspect 1, wherein the sample comprises whole blood.

Aspect 12. The method of Aspect 1, wherein at least one cell comprises a white blood cell, a red blood cell, a granulocyte, or a combination thereof.

Aspect 13. The method of Aspect 1, wherein contacting the sample with the formulation and the resulting chemical interaction with the biomarker is accomplished in a single step.

Aspect 14. The method of Aspect 1, wherein at least one of:

- contacting the sample with the stain formulation;
- the resulting chemical interaction or incubation of the stain formulation with the biomarker;
- imaging; or
- analyzing the image, is accomplished in 60 seconds or less.

Aspect 15. The method of Aspect 1, wherein contacting the sample with the formulation and the resulting chemical interaction with the biomarker is accomplished in a single step.

Aspect 16. The method of Aspect 1, wherein at least one of:

- contacting the sample with the stain formulation;
- the resulting chemical interaction or incubation of the stain formulation with the biomarker;
- imaging; or
- analyzing the image, is accomplished in 60 seconds or less.

Aspect 17. The method of Aspect 1, wherein the sample is a fresh crude biological sample selected from a needle biopsy, whole blood, urine, sputum, saliva, a swab sample (e.g., a pap smear), sweat, breath, breast milk, bile, or results from pathological process (such as blister or cyst fluid).

Aspect 18. The method of Aspect 1, wherein the presence of the targeted intracellular biomarker is indicative of the presence of at least one disease.

Aspect 19. The method of Aspect 1, wherein the presence and quantity of the targeted intracellular biomarker is more indicative than not of the presence of at least one disease.

Aspect 20. The method of Aspect 1, wherein the presence and quantity of the targeted intracellular biomarker is more indicative of the at least one disease and provides at least one disease diagnosis selected from the database of correlated biomarker and disease combinations.

Aspect 21. The method of Aspect 1, wherein the biomarker is indicative of at least one disease selected from an infectious disease, malignant disease, autoimmune disease, a metabolic disease, an inherited genetic disorder disease; or a combination thereof.

Aspect 22. The method of Aspect 1, wherein the intracellular biomarker is selected from a specific nucleic acid, a specific protein, or mixture thereof.

Aspect 23. A method for correlating a measured intracellular biomarker in a first cell with a measured diseased second cell or an organism having the diseased second cell, comprising:

contacting a sample containing at least one cell and an intracellular stain formulation to form an intracellular reaction product within a closed Q-card;

imaging the intracellular reaction product with an imager to generate an image of the intracellular reaction product;

analyzing the image to generate an analysis of the intracellular reaction product to determine the presence and the quantity of the measured intracellular biomarker; and generating at least one disease diagnosis by correlating the determined presence and the quantity of the measured intracellular biomarker with a database of correlated biomarkers and disease combinations.

The invention claimed is:

1. A method for analyzing a fresh whole-blood sample containing white blood cells using intra-cellular cytology, comprising:

(a) obtaining a sample holder comprising a first plate and a second plate, wherein the first plate and the second plate are movable relative to each other, and each of the first plate and the second plate has a surface for contacting the fresh whole-blood sample, and the sample holder comprises spacers located between the first plate and the second plate for regulating a spacing between the first plate and the second plate (b) depositing the fresh whole-blood sample on the surface of the first plate;

(c) contacting the fresh whole-blood sample on the surface of the first plate with an intracellular detection solution comprising a fluorescent-labeled oligonucleotide probe comprising SEQ ID NO: 1, a hybridization buffer, and a cell permeabilizer and producing permeabilized white blood cells, wherein the fluorescent-labeled oligonucleotide probe comprising SEQ ID NO: 1 is capable of being specifically hybridized to Interleukin-6 (IL-6) mRNA located inside of white blood cells of the fresh whole-blood sample;

(d) forming a layer containing the fluorescent-labeled oligonucleotide probe comprising SEQ ID NO: 1 and the permeabilized white blood cells between the surface of the first plate and the surface of the second plates by bringing the first plate and the second plate together to a closed configuration such that a thickness of the layer in the closed configuration is 10 microns or less than 10 microns;

(e) maintaining the layer in the closed configuration for not more than 120 seconds such that, inside of the layer, the fluorescent-labeled oligonucleotide probe comprising SEQ ID NO:1 is hybridized to the IL-6 mRNA inside of the permeabilized white blood cells and a fluorescent intracellular reaction product containing the fluorescent-labeled oligonucleotide probe comprising SEQ ID NO:1 and the IL-6 mRNA located inside of the permeabilized white blood cells is produced;

(f) after step (e), without washing away unbound fluorescent-labeled oligonucleotide probe from the layer in the closed configuration generating a fluorescence image of the fluorescent intracellular reaction product containing the fluorescent-labeled oligonucleotide probe comprising SEQ ID NO: 1 and the IL-6 mRNA located inside of the permeabilized white blood cells by imaging the layer in the closed configuration; and (g) determining the presence and quantity of the IL-6 mRNA located inside of the white blood cells in the fresh whole-blood sample by analyzing the fluorescence image of the fluorescent intracellular reaction product containing the fluorescent-labeled oligonucleotide probe comprising SEQ ID NO: 1 and the IL-6 mRNA located inside of the permeabilized white blood cells.

2. The method of claim 1, wherein the fluorescent-labeled oligonucleotide probe is a 60-mer Alexa488-labeled IL-6 oligonucleotide probe.

3. The method of claim 1, wherein the hybridization buffer comprises sodium phosphate buffer and formamide.

4. The method of claim 1, wherein the fresh whole-blood sample is undiluted whole blood.

5. The method of claim 1, wherein the white blood cells comprise granulocytes, monocytes, lymphocytes, or a combination thereof.

6. The method of claim 1, wherein the spacers are pillars fixed on one or both of the first plate and the second plate.

7. The method of claim 1, further comprising determining the presence and quantity of β2 microglobulin (B2M) mRNA inside of the white blood cell in the fresh whole-blood sample using the method recited in claim 1 wherein the fluorescent-labeled oligonucleotide probe comprising SEQ ID NO: 1 in the intracellular detection solution in step (c) is replaced by a fluorescent-labeled oligonucleotide probe that hybridizes to the B2M mRNA located inside of the white blood cells such that step (e) produces a fluorescent intracellular reaction product containing the fluorescent-labeled oligonucleotide probe that hybridizes to the B2M mRNA and the B2M mRNA located inside of the permeabilized white blood cells and step (f) generates a fluorescence image of the fluorescent intracellular reaction product containing the fluorescent-labeled oligonucleotide probe that hybridizes to the B2M mRNA and the B2M mRNA located inside of the permeabilized white blood cells, and wherein the fluorescence image of the fluorescent intracellular reaction product containing the fluorescent-labeled oligonucleotide probe that hybridizes to the B2M mRNA and the B2M mRNA located inside of the permeabilized white blood cells is used as an internal control for normalizing the quantity of the IL-6 mRNA located inside of the white blood cells in the fresh whole-blood sample.

8. The method of claim 7, wherein the fluorescent-labeled oligonucleotide probe that hybridizes to the B2M mRNA located inside of the white blood cells comprises SEQ ID NO: 2.

9. The method of claim 1, wherein the intracellular detection solution is coated and dried on the surface of the second plate before the fresh whole-blood sample is deposited on the surface of the first plate, and wherein said bringing the first plate and the second plate together to a closed configuration dissolves at least a portion of the coated and dried intracellular detection solution into the fresh whole-blood sample.

10. The method of claim 1, wherein said imaging the layer in the closed configuration is performed using a fluorescence microscope or a mobile communication device adapted for acquiring and analyzing images of cells.

11. The method of claim 1, wherein said analyzing the fluorescence image of the fluorescent intracellular reaction product containing the fluorescent-labeled oligonucleotide probe comprising SEQ ID NO: 1 and the IL-6 mRNA located inside of the permeabilized white blood cells identifies IL-6-positive white blood cells in the fresh whole-blood sample.

12. The method of claim 1, wherein the permeabilized white blood cells inside of the layer in the closed configuration do not substantially overlap one another.

* * * * *

SEQUENCE LISTING

<160> NUMBER OF SEQ ID NOS: 21

<210> SEQ ID NO 1
<211> LENGTH: 60
<212> TYPE: DNA
<213> ORGANISM: Artificial Sequence
<220> FEATURE:
<223> OTHER INFORMATION: synthetic oligo probe

<400> SEQUENCE: 1
tctgcaggaa ctggatcagg acttttgtac tcatctgcac agctctggct tgttcctcac 60

<210> SEQ ID NO 2
<211> LENGTH: 59
<212> TYPE: DNA
<213> ORGANISM: Artificial
<220> FEATURE:
<223> OTHER INFORMATION: synthetic oligo probe

<400> SEQUENCE: 2
atcttcaaac ctccatgatg ctgcttacat gtctcgatcc cacttaacta tcttgggct 59

<210> SEQ ID NO 3
<211> LENGTH: 60
<212> TYPE: DNA
<213> ORGANISM: Artificial
<220> FEATURE:
<223> OTHER INFORMATION: synthetic oligo probe

<400> SEQUENCE: 3
atggcggact tgaagaagtc gtgctgcttc atgtggtcgg ggtagcggct gaagcactgc 60

<210> SEQ ID NO 4
<211> LENGTH: 60
<212> TYPE: DNA
<213> ORGANISM: Artificial
<220> FEATURE:
<223> OTHER INFORMATION: Synthetic oligo

<400> SEQUENCE: 4
tagagcaggt ggattaaact tcaactctat ttgttggagt gttaacaatg cagtggcaag 60

<210> SEQ ID NO 5
<211> LENGTH: 60
<212> TYPE: DNA
<213> ORGANISM: Artificial
<220> FEATURE:
<223> OTHER INFORMATION: synthetic oligo

<400> SEQUENCE: 5
caactggttt tgtgctccaa agacaacgta tacaccaggt atttggttta tacgtggctt 60

<210> SEQ ID NO 6
<211> LENGTH: 60
<212> TYPE: DNA
<213> ORGANISM: Artificial
<220> FEATURE:
<223> OTHER INFORMATION: synthetic oligo

<400> SEQUENCE: 6
agtacaaaca cggtttaaac accgtgtaac tatgttagta gttgtactaa caactttgtt 60

<210> SEQ ID NO 7
<211> LENGTH: 60
<212> TYPE: DNA
<213> ORGANISM: Artificial
<220> FEATURE:
<223> OTHER INFORMATION: Synthetic oligo

<400> SEQUENCE: 7
ggtgattcct taaaacgttt agctagtcca atcagtagat gtaaaccacc taactgacta 60

<210> SEQ ID NO 8
<211> LENGTH: 60
<212> TYPE: DNA
<213> ORGANISM: Artificial
<220> FEATURE:
<223> OTHER INFORMATION: Synthetic oligo

<400> SEQUENCE: 8
ttgtcattaa gaccttcgga accttctcca acaacacctg tatggttaca acctatgtta 60

<210> SEQ ID NO 9
<211> LENGTH: 60
<212> TYPE: DNA
<213> ORGANISM: Artificial
<220> FEATURE:
<223> OTHER INFORMATION: Synthetic oligo

<400> SEQUENCE: 9
ttatactctg caagaagtag actaaagcat aaagatagag aaaaggggct tcaaggccag 60

<210> SEQ ID NO 10
<211> LENGTH: 60
<212> TYPE: DNA
<213> ORGANISM: Artificial
<220> FEATURE:
<223> OTHER INFORMATION: Synthetic oligo

<400> SEQUENCE: 10
tgaaggagta gcatccttga tttcaccttg cttcaaagtt acagttccaa ttgtgaagat 60

<210> SEQ ID NO 11
<211> LENGTH: 46
<212> TYPE: DNA
<213> ORGANISM: Artificial
<220> FEATURE:
<223> OTHER INFORMATION: Synthetic oligo

<400> SEQUENCE: 11
cctcttagta ccattggtcc cagagacatg tatagcatgg aaccaa 46

<210> SEQ ID NO 12
<211> LENGTH: 59
<212> TYPE: DNA
<213> ORGANISM: Artificial
<220> FEATURE:

<223> OTHER INFORMATION: Synthetic oligo

<400> SEQUENCE: 12
ttcgcactag aataaactct gaactcactt tccatccaac ttttgttgtt tttgtggta 59

<210> SEQ ID NO 13
<211> LENGTH: 60
<212> TYPE: DNA
<213> ORGANISM: Artificial
<220> FEATURE:
<223> OTHER INFORMATION: Synthetic oligo

<400> SEQUENCE: 13
ccaacctgaa gaagaatcac caggagtcaa ataacttcta tgtaaagcaa gtaaagtttg 60

<210> SEQ ID NO 14
<211> LENGTH: 59
<212> TYPE: DNA
<213> ORGANISM: Artificial
<220> FEATURE:
<223> OTHER INFORMATION: Synthetic oligo

<400> SEQUENCE: 14
cagcaccagc tgtccaacct gaagaagaat caccaggagt caaataactt ctatgtaaa 59

<210> SEQ ID NO 15
<211> LENGTH: 27
<212> TYPE: PRT
<213> ORGANISM: Artificial
<220> FEATURE:
<223> OTHER INFORMATION: synthetic peptide

<400> SEQUENCE: 15

```
Pro Pro Gly Lys Pro Gln Gly Pro Pro Pro Gln Gly Gly Asn Gln Pro
1               5                   10                  15

Gln Gly Pro Pro Pro Pro Pro Gly Lys Pro Gln
            20                  25
```

<210> SEQ ID NO 16
<211> LENGTH: 25
<212> TYPE: PRT
<213> ORGANISM: Artificial
<220> FEATURE:
<223> OTHER INFORMATION: Synthetic peptide

<400> SEQUENCE: 16

```
Gly Asn Pro Gln Gly Pro Ser Pro Gln Gly Gly Asn Lys Pro Gln Gly
1               5                   10                  15

Pro Pro Pro Pro Pro Gly Lys Pro Gln
            20                  25
```

<210> SEQ ID NO 17
<211> LENGTH: 27
<212> TYPE: PRT
<213> ORGANISM: Artificial
<220> FEATURE:
<223> OTHER INFORMATION: Synthetic peptide

<400> SEQUENCE: 17

```
Ser Pro Pro Gly Lys Pro Gln Gly Pro Pro Gln Gln Glu Gly Asn Lys
1               5                   10                  15

Pro Gln Gly Pro Pro Pro Pro Gly Lys Pro Gln
            20                  25
```

-continued

```
<210> SEQ ID NO 18
<211> LENGTH: 7
<212> TYPE: PRT
<213> ORGANISM: Artificial
<220> FEATURE:
<223> OTHER INFORMATION: Synthetic peptide

<400> SEQUENCE: 18

Gly Gly His Pro Pro Pro Pro
1               5


<210> SEQ ID NO 19
<211> LENGTH: 7
<212> TYPE: PRT
<213> ORGANISM: Artificial
<220> FEATURE:
<223> OTHER INFORMATION: synthetic peptide

<400> SEQUENCE: 19

Glu Ser Pro Ser Leu Ile Ala
1               5


<210> SEQ ID NO 20
<211> LENGTH: 15
<212> TYPE: PRT
<213> ORGANISM: Artificial
<220> FEATURE:
<223> OTHER INFORMATION: Synthetic peptide

<400> SEQUENCE: 20

Ser Lys Ile Thr His Arg Ile His Trp Glu Ser Ala Ser Leu Leu
1               5                   10                  15


<210> SEQ ID NO 21
<211> LENGTH: 11
<212> TYPE: PRT
<213> ORGANISM: Artificial
<220> FEATURE:
<223> OTHER INFORMATION: Synthetic peptide

<400> SEQUENCE: 21

Ala His Lys Ser Glu Val Ala His Arg Phe Lys
1               5                   10
```